US006339068B1

(12) United States Patent
Krieg et al.

(10) Patent No.: US 6,339,068 B1
(45) Date of Patent: Jan. 15, 2002

(54) VECTORS AND METHODS FOR IMMUNIZATION OR THERAPEUTIC PROTOCOLS

(75) Inventors: Arthur M. Krieg, Iowa City, IA (US); Heather L. Davis, Ottawa; Tong Wu, Hull, both of (CA); Joachim Schorr, Hilden (DE)

(73) Assignees: University of Iowa Research Foundation, Iowa City, IA (US); Loeb Health Research Institute at the Ottawa Hospital, Ottawa (CA); Coley Pharmaceutical GmbH, Langenfeld (DE)

( * ) Notice: Subject to any disclaimer, the term of this patent is extended or adjusted under 35 U.S.C. 154(b) by 0 days.

(21) Appl. No.: 09/082,649

(22) Filed: May 20, 1998

Related U.S. Application Data

(60) Provisional application No. 60/047,209, filed on May 20, 1997, and provisional application No. 60/047,233, filed on May 20, 1997.

(51) Int. Cl.$^7$ .................. A61K 48/00; C12N 15/00; C12N 15/88

(52) U.S. Cl. .................. 514/44; 424/93.2; 435/91.4; 435/91.41; 435/91.42; 435/320.1; 435/455

(58) Field of Search .................. 514/44; 424/93.21; 435/69.1, 320.1, 325, 455, 458, 91.4, 91.41, 91.42; 536/23.1

(56) References Cited

U.S. PATENT DOCUMENTS

| | | | |
|---|---|---|---|
| 3,906,092 A | 9/1975 | Hilleman et al. | 424/89 |
| 4,844,904 A | 7/1989 | Hamaguchi et al. | 424/450 |
| 4,863,740 A | 9/1989 | Kissel et al. | 424/450 |
| 4,975,282 A | 12/1990 | Cullis et al. | 424/450 |
| 5,000,959 A | 3/1991 | Iga et al. | 424/450 |
| 5,248,670 A | 9/1993 | Draper et al. | 514/44 |
| 5,580,859 A | 12/1996 | Felgner et al. | 514/44 |
| 5,585,479 A | 12/1996 | Hoke et al. | 536/24.5 |
| 5,589,466 A | 12/1996 | Felgner et al. | 514/44 |
| 5,663,153 A | 9/1997 | Hutcherson et al. | 514/44 |
| 5,679,647 A | 10/1997 | Carson et al. | 514/44 |
| 5,723,335 A | 3/1998 | Hutcherson et al. | 435/375 |
| 5,780,448 A | 7/1998 | Davis | 514/44 |
| 5,786,189 A | 7/1998 | Locht et al. | 435/455 |
| 5,849,719 A | 12/1998 | Carson et al. | 514/44 |

FOREIGN PATENT DOCUMENTS

| | | |
|---|---|---|
| EP | 0468520 A3 | 1/1992 |
| EP | 0302758 B1 | 3/1994 |
| EP | 0773295 | 5/1997 |
| WO | WO 90/11092 | 10/1990 |
| WO | WO 91/12811 | 9/1991 |
| WO | WO 92/03456 | 3/1992 |
| WO | WO 92/18522 | 10/1992 |
| WO | WO 92/21353 | 12/1992 |
| WO | WO 94/19945 | 9/1994 |
| WO | WO 95/05853 | 3/1995 |
| WO | WO 95/26204 | 10/1995 |
| WO | WO 96/02555 | 2/1996 |
| WO | WO 96/13277 | 5/1996 |
| WO | WO 96/14074 | 5/1996 |
| WO | WO 96/35782 | 11/1996 |
| WO | WO 97/28259 | 8/1997 |
| WO | WO 98/14210 | 4/1998 |
| WO | WO 98/52581 | 11/1998 |
| WO | WO 99/41368 A2 | 8/1999 |
| WO | WO 99/41368 A3 | 8/1999 |

OTHER PUBLICATIONS

Verma et al., Gene therapy promises, problems and prospects, Nature vol. 389, Sep. 18, 1997, pp. 239–242.*
Anderson, Human Gene therapy, Nature vol. 392, Apr. 30, 1998, pp. 25–30.*
McCluskie et al. (Molecular Medicine, 5, pp. 287–300), 1999.*
Cryz et al. (Vaccine, vol. 14, 7, Vaccine Delivery Systems, Reports of the Expert Panels, pp. 665–688), 1996.*
Sato et al., "Immunostimulatory DNA Sequences Necessary for Effective Intradermal Gene Immunization", *Science*, Sep. 19, 1996, vol. 273, pp. 352–354.
Klinman et al., "Contribution of CpG Motifs to the Immunogenicity of DNA Vaccines," *J. Immunol.*, Apr. 1997, vol. 158, pp. 3635–3639.
Cox GJM et al. Bovine herpesvirus 1: immune responses in mice and cattle injected with plasmid DNA. *J Virol* Sep. 1993; 67(9):5664–7.
Lipford GB et al. Immunostimulatory DNA: sequence–dependent production of potentially harmful or useful cytokines. *Eur J Immunol* Dec. 1997; 27(12):3420–6.
Morahan PS et al. Comparative analysis of modulators of nonspecific resistance against microbial infections. *Immunopharmacology of Infectious Diseases: Vaccine Adjuvants and Modulators of Nonspecific Resistance.* 1987. Alan R. Liss, pp 313–24.
Parker SE et al. Plasmid DNA gene therapy: studies with the human interleukin–2 gene in tumor cells in vitro and in the murine B16 melanoma model in vivo. *Cancer Gene Therapy* May–Jun. 1996; 3(3):175–85.

(List continued on next page.)

*Primary Examiner*—Dave T. Nguyen
(74) *Attorney, Agent, or Firm*—Wolf, Greenfield & Sacks, P. C.

(57) ABSTRACT

The present invention shows that DNA vaccine vectors can be improved by removal of CpG-N motifs and optional addition of CpG-S motifs. In addition, for high and long-lasting levels of expression, the optimized vector should include a promoter/enhancer that is not down-regulated by the cytokines induced by the immunostimulatory CpG motifs. Vectors and methods of use for immunostimulation are provided herein. The invention also provides improved gene therapy vectors by determining the CpG-N and CpG-S motifs present in the construct, removing stimulatory CpG (CpG-S) motifs and/or inserting neutralizing CpG (CpG-N) motifs, thereby producing a nucleic acid construct providing enhanced expression of the therapeutic polypeptide. Methods of use for such vectors are also included herein.

109 Claims, 15 Drawing Sheets

OTHER PUBLICATIONS

Ulmer JB et al. Heterologous protection against influenza by injection of DNA encoding a viral protein. *Science* Mar. 19, 1993; 259:1745–9.

Vogels MTE et al. Use of immune modulators in nonspecific therapy of bacterial infections. *Antimicrob Agents Chemother* Jan. 1992; 36(1):1–5.

Wang B et al. Gene inoculation generates immune responses against human immunodeficiency virus type I. *Proc Natl Acad Sci USA* May 1993; 90:4156–60.

Wloch MK et al. The influence of DNA sequence on the immunostimulatory properties of plasmid DNA vectors. *Human Gene Therapy* Jul. 1, 1998; 1439–47.

Karlin S et al., Why is CpG suppressed in the genomes of virtually all small eukaryotic viruses but not in those of large eukaryotic viruses? *J Virol.* May 1994; 68(5):2889–97.

Krieg AM et al., Sequence motifs in adenoviral DNA block immune activation by stimulatory CpG motifs. *Proc Natl Acad Sci U S A.* Oct. 13, 1998; 95(21):12631–6.

Schreiber E et al., Long–range activation of transcription by SV40 enhancer is affected by "inhibitory" or "permissive" DNA sequences between enhancer and promoter. *Somat Cell Mol Genet.* Nov. 1989; 15(6):591–603.

Adya N et al., Expansion of CREB's DNA recognition specificity by Tax results from interaction with Ala–Ala–Arg at positions 282–284 near the conserved DNA–binding domain of CREB. *Proc Natl Acad Sci USA* 91(12):5642–6, Jun. 7, 1994.

Allison AC et al., The development of an adjuvant formulation that elicits cell–mediated and humoral immune responses to virus subunit and other antigens. *Immunopharmacology of Infections Diseases: Vaccine Adjuvants and Modulators of Non–Specific Resistance,* pp. 191–201, 1987.

Angier N., Microbe DNA seen as alien by immune system, *New York Times,* Apr. 11, 1995.

Azad RF et al., Antiviral activity of a phosphorothioate oligonucleotide complementary to RNA of the human cytomegalovirus major immediate–early region. *Antimicrobial Agents and Chemotherapy,* 37:1945–1954, Sep., 1993.

Azuma I, Biochemical and immunological studies on cellular components of *tubercle bacilli. Kekkaku* 69(9):45–55, 1992.

Ballas ZK et al., Induction of NK activity in murine and human cells by CpG motifs in oligodeoxynucleotides and bacterial DNA. *J Immunol* 157(5):1840–5, 1996.

Bayever, E et al., Systemic administration of a phosphorothioate oligonucleotide with a sequence complementary to p53 for acute myelogenous leukemia and myelodysplastic syndrome: initial results of a phase I trial. *Antisense Res Dev* 3:383–390, 1993.

Bennett RM et al., DNA binding to human leukocytes. Evidence for a receptor–mediated association, internalization, and degradation of DNA. *J Clin Invest* 76(6):2182–90, 1985.

Berg DJ et al., Interleukin–10 is a central regulator of the response to LPS in murine models of endotoxic shock and the Shwartzman reaction but not endotoxin tolerance. *J Clin Invest* 96(5):2339–47, 1995.

Blanchard DK et al., Interferon–gamma induction by lipopolysaccharide: dependence on interleukin 2 and macrophages. *J Immunol* 136(3):963–70, 1986.

Blaxter ML et al., Genes expressed in *Brugia malayi* infective third stage larvae. *Molecular and Biochemical Parasitology* 77:77–93, 1996.

Boggs RT et al., Characterization and modulation of immune stimulation by modified oligonucleotides. *Antisense Nucleic Acid Drug Dev* 7(5):461–71, Oct. 1997.

Branda RF et al., Amplification of antibody production by phosphorothioate oligodeoxynucleotides. *J Lab Clin Med* 128(3):329–38, Sep. 1996.

Branda RF et al., immune stimulation by an antisense oligomer complementary to the rev gene of HIV–1. *Biochemical Pharmacology* 45(10):2037–2043, 1993.

Briskin M et al., Lipopolysaccharide–unresponsive mutant pre–B–cell lines blocked in NF–kappa B activation. *Mol Cell Biol* 10(1):422–5, Jan. 1990.

Burgess TL et al., The antiproliferative activity of c–myb and c–myc antisense oligonucleotides in smooth muscle cells is caused by a nonantisense mechanism. *Proc Natl Acad Sci USA* 92(9):4051–5, 1995.

Chace J et al., Regulation of differentiation in CD5+ and conventional B cells. *Clinical Immunology and Immunopathology* 68(3):327–332, 1993.

Chang YN et al., The palindromic series I repeats in the simian cytomegalovirus major immediate–early promoter behave as both strong basal enhancers and cyclic AMP response elements. *J Virol* 64(1):264–77, Jan. 1990.

Chu RS et al., CpG oligodeoxynucleotides act as adjuvants that switch on T helper 1 (Th1) immunity. *J Exp Med* 186(10):1623–31, Nov. 17, 1997.

Condon C et al., DNA–based immunization by in vivo transfection of dendritic cells. *Nat Med* 2(10):1122–8, 1996.

Corr M et al., Gene vaccination with naked plasmid DNA: mechanism of CTL priming. *J Exp Med* 184(4):1555–60, 1996.

Cowdery JS et al., Bacterial DNA induces NK cells to produce IFN–gamma in vivo and increases the toxicity of lipopolysaccharides. *J Immunol* 156(12):4570–5, Jun. 15, 1996.

Crosby SD et al., The early response gene NGFI–C encodes a zinc finger transcriptional activator and is a member of the GCGGGGGCG (GSG) element–binding protein family. *Mol Cell Biol* 2:3835–3841, 1991.

Crystal RG, Transfer of genes to humans: early lessons and obstacles to success. *Science* 270:404–410, 1995.

D'Andrea A et al., Interleukin 10 (IL–10) inhibits human lymphocyte interferon gamma–production by suppressing natural killer cell stimulatory factor/IL–12 synthesis in accessory cells. *J Exp Med* 178(3):1041–8, 1993.

Davis HL et al., CpG DNA is a potent enhancer of specific immunity in mice immunized with recombinant hepatitis B surface antigen. *J Immunol* 160(2):870–6, 1998.

Davis HL et al., Direct gene transfer into skeletal muscle in vivo: factors affecting efficiency of transfer and stability of expression. *Hum Gene Ther* 4(2):151–9, 1993.

Davis HL et al., DNA vaccine for hepatitis B: evidence for immunogenicity in chimpanzees and comparison with other vaccines. *Proc Natl Acad Sci USA* 93(14):7213–8, 1996.

Davis HL et al., DNA–based immunization induces continuous secretion of hepatitis B surface antigen and high levels of circulating antibody. *Hum Mol Genet* 2(11):1847–51, 1993.

Davis HL, Plasmid DNA expression systems for the purpose of immunization. *Curr Opin Biotechnol* 8(5):635–46, 1997.

Doe B et al., Induction of cytotoxic T lymphocytes by intramuscular immunization with plasmid DNA is facilitated by bone marrow–derived cells. *Proc Natl Acad Sci USA* 93:8578–8583, 1996.

Englisch U et al., Chemically modified oligonucleotides as probes and inhibitors, *Angew Chem Int Ed Engl* 30:613–629, 1991.

Erb KJ et al., Infection of mice with *Mycobacterium bovis–Bacillus* Calmette–Guerin (BCG) suppresses allergen–induced airway eosinophilia. *J Exp Med* 187(4):561–9, Feb. 16, 1998.

Etchart N et al., Class I–restricted CTL induction by mucosal immunization with naked DNA encoding measles virus haemagglutinin. *J Gen Virol* 78(7):1577–80, 1997.

Etlinger HM, Carrier sequence selection—one key to successful vaccines. *Immunology Today* 13(2):52–55, 1992.

Fox RI, Mechanism of action of hydroxychloroquine as an antirheumatic drug. *Chemical Abstracts,* 120:15, Abstract No. 182630 (Apr. 29, 1994).

Fynan EF et al., DNA vaccines: protective immunizations by parenteral, mucosal, and gene–gun inoculations. *Proc Natl Acad Sci USA* 90(24):11478–82, 1993.

Gramzinski RA et al., Immune response to a hepatitis B DNA vaccine in Aotus monkeys: a comparison of vaccine formulation, route, and method of administration. *Mol Med* 4(2):109–18, 1998.

Gura, T., Antisense Has Growing Pains. *Science* 270:575–576, 1995.

Hadden JW et al., Immunopharmacology: immunomodulation and immunotherapy. *JAMA* 268(20):2964–2969, 1992.

Hadden JW, Immunostimulants. *TIPS* 14:169–174, 1993.

Halpern MD et al., Bacterial DNA induces murine interferon–gamma production by stimulation of interleukin–12 and tumor necrosis factor–alpha. *Cell Immunol* 167(1):72–8, 1996.

Harms JS and Splitter GA, Interferon–gamma inhibits transgene expression driven by SV40 or CMV promoters but augments expression driven by the mammalian MHC I promoter. *Hum Gene Ther* 6(10):1291–7, 1995.

Hatzfeld J et al., Release of early human hematopoietic progenitors from quiescence by antisense transforming growth factor β1 or Rb oligonucleotides. *J Exp Med* 174:925–929, 1991.

Highfield PE, Sepsis: the more, the murkier. *Biotechnology* 12:828, Aug. 12, 1994.

Hoeffler JP et al., Identification of multiple nuclear factors that interact with cyclic adenosine 3',5'-monophosphate response element–binding protein and activating transcription factor–2 by protein–protein interactions. *Mol Endocrinol* 5(2):256–66, Feb. 1991.

Iguchi–Ariga SM and Shaffner W, CpG methylation of the cAMP–responsive enhancer/promoter sequence TGACGTCA abolishes specific factor binding as well as transcriptional activation. *Genes Dev* 3(5):612–9, May 1989.

International Search Report, PCT/US98/10408, WO 98/52581, Sep. 2, 1998.

Ishikawa R et al., IFN induction and associated changes in splenic leukocyte distribution. *J Immunol* 150(9):3713–27, May 1, 1993.

Iversen P et al., Pharmacokinetics of an antisense phosphorothioate oligodeoxynucleotide against rev from human immunodeficiency virus type 1 in the adult male rate following single injections and continuous infusion. *Antisense Res Dev* 4:43–52, 1994.

Jakway JP et al., Growth regulation of the B lymphoma cell line WEHI–231 by anti–immunoglobulin, lipopolysaccharide, and other bacterial products. *J Immunol* 137(7):2225–31, Oct. 1, 1986.

Jaroszewski JW and Cohen JS, Cellular uptake of antisense oligonucleotides. *Adv Drug Delivery Rev* 6(3):235–50, 1991.

Kimura Y et al., Binding of oligoguanylate to scavenger receptors is required for oligonucleotides to augment NK cell activity and induce IFN. *J Biochem* 116(5):991–994, 1994.

Kline JN et al., CpG motif oligonucleotides are effective in prevention of eosinophilic inflammation in a murine model of asthma. *J Invest Med* 44(7):380A, 1996.

Kline JN et al., CpG oligonucleotides can reverse as well as prevent Th2–mediated inflammation in a murine model of asthma. *J Invest Med* 45(7):298A, 1997.

Kline JN et al., Immune redirection by CpG oligonucleotides. Conversion of a Th2 response to a Th1 response in a murine model of asthma. *J Invest Med* 45(3):282A, 1997.

Klinman DM et al., Contribution of CpG motifs to the immunogenicity of DNA vaccines. *J Immunol* 158:3635, 1997.

Klinman DM et al., CpG motifs present in bacteria DNA rapidly induce lymphocytes to secrete interleukin 6, interleukin 12, and interferon gamma. *Proc Natl Acad Sci USA* 93(7):2879–83, 1996.

Krieg AM et al., A role for endogenous retroviral sequences in the regulation of lymphocyte activation. *J Immunol* 143:2448–2451, 1989.

Krieg AM et al., CpG DNA: A pathogenic factor in systemic lupus erythematosus? *J Clin Immunol* 15(6):284–292, 1995.

Krieg AM et al., CpG motifs in bacterial DNA trigger direct B–cell activation. *Nature* 374:546–9, 1995.

Krieg AM et al., Leukocyte stimulation by oligodeoxynucleotides. *Applied Antisense Oligonucleotide Technology* 431–448, 1998.

Krieg AM et al., Modification of antisense phosphodiester oligodeoxynucleotides by a 5' cholesteryl moiety increases cellular association and improves efficacy. *Proc Natl Acad Sci USA* 90:1048–1052, 1993.

Krieg AM et al., Oligodeoxynucleotide modifications determine the magnitude of B cell stimulation by CpG motifs. *Antisense Nucleic Acid Drug Dev* 6(2):133–9, Summer 1996.

Krieg AM et al., Phosphorothioate oligodeoxynucleotides: antisense or anti–protein? *Antisense Res Dev* 5:241, 1995.

Krieg AM et al., The role of CpG dinucleotides in DNA vaccines. *Trends in Microbiology* 6:23–27, Jan. 1998.

Krieg AM et al., Uptake of oligodeoxyribonucleotides by lymphoid cells is heterogeneous and inducible. *Antisense Res Dev* 1(2):161–71, Summer 1991.

Krieg AM, An innate immune defense mechanism based on the recognition of CpG motifs in microbial DNA. *J Lab Clin Med* 128(2):128–33, 1996.

Kuramoto E et al., Oligonucleotide sequences required for natural killer cell activation. *Jpn J Cancer Res* 83:1128–1131, Nov. 1992.

Leclerc C et al., The preferential induction of a Th1 immune response by DNA–based immunization is mediated by the immunostimulatory effect of plasmid DNA. *Cell Immunol* 179(2):97–106, 1997.

Leonard GA et al., Conformation of guanine 8–oxoadenine base pairs in the crystal structure of d(CGCGAATT(O8A)GCG). *Biochemistry* 31(36):8415–8420, 1992.

Lipford GB et al., CpG–containing synthetic oligonucleotides promote B and cytotoxic T cell responses to protein antigen: a new class of vaccine adjuvants. *Eur J Immunol* 27(9):2340–4, 1997.

Liu MA et al., Immunization of non–human primates with DNA vaccines. *Vaccine* 15(8):909–12, 1997.

Macfarlane DE and Manzel L, Antagonism of immunostimulatory CpG–oligodeoxynucleotides by quinacrine, chloroquine, and structurally related compounds. *J Immunol* 160(3):1122–31, Feb. 1, 1998.

Mannino RJ et al., Lipid matrix–based vaccines for mucosal and systemic immunization. *Vaccine Design: The Subunit and Adjuvant Approach,* Chapter 15, pp. 363–387, 1995.

Mastrangelo MJ et al., Gene therapy for human cancer. *Seminars in Oncology* 23(1):4–21, 1996.

Matson S and Krieg AM, Nonspecific suppression of [$^3$H] thymidine incorporation by "control" oligonucleotides. *Antisense Res Dev* 2(4):325–30, Winter 1992.

McIntyre KW et al., A sense phosphorothioate oligonucleotide directed to the initiation codon of transcription factor NF–kappa B p65 causes sequence–specific immune stimulation. *Antisense Res Dev* 3(4):309–22, Winter 1993.

Messina JP et al., Stimulation of in vitro murine lymphocyte proliferation by bacterial DNA. *J Immunol* 147(6):1759–1764, Sep. 15, 1991.

Messina JP et al., The influence of DNA structure on the in vitro stimulation of murine lymphocytes by natural and synthetic polynucleotide antigens. *Cell Immunol* 147:148–157, 1993.

Mojcik CF et al., Administration of a phosphorothioate oligonucleotide antisense murine endogenous retroviral MCF env causes immune effects in vivo in a sequence–specific manner. *Clinical Immunology and Immunopathology* 67(2):130–136, 1993.

Mottram JC et al., A novel CDC2–related protein kinase from *Leishmania mexicana,* LmmCRK1, is post–translationally regulated during the life cycle. *J Biol Chem* 268(28):21044–21052, Oct. 1993.

*New England BIOLABS 1988–1989 Catalog.*

Nyce JW and Metzger WJ, DNA antisense therapy for asthma in an animal model. *Nature* 385:721–725, Feb. 20, 1997.

Pisetsky DS and Reich C, Stimulation of in vitro proliferation of murine lymphocytes by synthetic oligodeoxynucleotides. *Mol Biol Rep* 18(3):217–221, 1993.

Pisetsky DS and Reich CF, Stimulation of murine lymphocyte proliferation by a phosphorothioate oligonucleotide with antisense activity for herpes simplex virus. *Life Science* 54:101–107, 1994.

Pisetsky DS, Immunologic consequences of nucleic acid therapy. *Antisense Res Dev* 5:219–225, 1995.

Pisetsky DS, The immunologic properties of DNA. *J Immunol* 156(2):421–423, 1996.

Prince AM et al., Successful nucleic acid based immunization of newborn chimpanzees against hepatitis B virus. *Vaccine* 15(8):916–9, 1997.

Raz E et al., Intradermal gene immunization: the possible role of DNA uptake in the induction of cellular immunity to viruses. *Proc Natl Acad Sci USA* 91(20):9519–23, 1994.

Raz E et al., Preferential induction of a Th1 immune response and inhibition of specific IgE antibody formation by plasmid DNA immunization. *Proc Natl Acad Sci USA* 93(10):5141–5, May 14, 1996.

Roman M et al., Immunostimulatory DNA sequences function as T helper–1 promoting adjuvants. *Nat Med* 3(8):849–54, Aug. 1997.

Sato Y et al., Immunostimulatory DNA sequences necessary for effective intradermal gene immunization. *Science* 273(5273):352, Jul. 19, 1996.

Schnell N et al., Identification and characterization of a *Saccharomyces cerevisiae* gene (PAR1) conferring resistance to iron chelators. *Eur J Biochem* 200:487–493, 1991.

Schwartz DA et al., CpG motifs in bacterial DNA cause inflammation in the lower respiratory tract. *J Clin Invest* 100(1):68–73, Jul. 1, 1997.

Schwartz DA et al., Endotoxin responsiveness and grain dust–induced inflammation in the lower respiratory tract. *Am J Physiol* 267(5 Pt 1):L609–17, 1994.

Schwartz DA et al., The role of endotoxin in grain dust–induced lung disease. *Am J Respir Crit Care Med* 152(2):603–8, 1995.

Shirakawa T et al., The inverse association between tuberculin responses and atopic disorder. *Science* 275(5296):77–9, Jan. 3, 1997.

Sparwasser T et al., Macrophages sense pathogens via DNA motifs: induction of tumor necrosis factor–α–mediated shock. *Eur J Immunol* 27(7):1671–9, Jul. 1997.

Stein CA et al., Oligonucleotides as inhibitors of gene expression: a review. *Cancer Res* 48:2659–2668, 1988.

Stull RA et al., Antigene, ribozyme, and aptamer nucleic acid drugs: progress and prospects. *Pharmaceutical Res* 12(4):465–483, 1995.

Subramanian PS et al., Theoretical considerations on the "spine of hydration" in the minor groove of d(CGCGAATTCGCG)·d(GCGCTTAAGCGC): Monte Carlo computer simulation. *Proc Natl Acad Sci USA* 85:1836–1840, 1988.

Tanaka T et al., An antisense oligonucleotide complementary to a sequence in Iγ2b increases γ2b germline transcripts, stimulates B cell DNA synthesis, and inhibits immunoglobulin secretion. *J Exp Med* 175:597–607, 1992.

Tang D–C et al., Genetic immunization is a simple method for eliciting an immune response. *Nature* 356(6365):152–4, 1992.

Thorne PS, Experimental grain dust atmospheres generated by wet and dry aerosolization techniques. *Am J Ind Med* 25(1):109–12, 1994.

Tokunaga T et al., A synthetic single–stranded DNA, poly (dG,dC), induces interferon α/β and –γ, augments natural killer activity, and suppresses tumor growth. *Jpn J Cancer Res* 79:682–686, Jun. 1988.

Tokunaga T et al., Synthetic oligonucleotides with particular base sequences form the cDNA encoding proteins of *Mycobacterium bovis* BCG induce interferons and activate natural killer cells. *Microbiol Immunol* 36(1):55–66, 1992.

Tomasi M et al., Strong mucosal adjuvanticity of cholera toxin within lipid particles of a new multiple emulsion delivery system for oral immunization. *Eur J Immunol* 27:2720–2725, 1997.

Uhlmann E et al., Antisense oligonucleotides: a new therapeutic principle. *Chem Rev* 90:543–584, 1990.

Wagner RW, Gene inhibition using antisense oligodeoxynucleotides. *Nature* 372:333–335, 1994.

Wallace RB et al., Oligonucleotide probes for the screening of recombinant DNA libraries. *Methods in Enzymology* 152:432–442, 1987.

Weiner GJ et al., Immunostimulatory oligodeoxynucleotides containing the CpG motif are effective as immune adjuvants in tumor antigen immunization. *Proc Natl Acad Sci USA* 94(20):10833–7, 1997.

Weiss R, Upping the antisense ante: Scientists bet on profits from reverse genetics. *Science* 139:108–109, 1991.

Whalen RG, DNA vaccines for emerging infection diseases: what if? *Emerging Infectious Disease* 2(3):168–175, 1996.

Wu GY et al., Receptor–mediated gene delivery and expression in vivo. *J Biol Chem* 263:14621–14624, 1988.

Wu–Pong S, Oligonucleotides: opportunities for drug therapy and research. *Pharmaceutical Technology* 18:102–114, 1994.

Xiang ZQ et al., The effect of interferon–gamma on genetic immunization. *Vaccine* 15(8):896–8, 1997.

Yamamoto S et al., DNA from bacteria, but not from vertebrates, induces interferons, activates natural killer cells and inhibits tumor growth. *Microbiol Immunol* 36(9):983–97, 1992.

Yamamoto S et al., In vitro augmentation of natural killer cell activity and production of interferon–alpha/beta and—gamma with deoxyribonucleic acid fraction from *Mycobacterium bovis* BCG. *Jpn J Cancer Res* 79:866–73, Jul. 1988.

Yamamoto S et al., Unique palindromic sequences in synthetic oligonucleotides are required to induce INF and augment INF–mediated natural killer activity. *J Immunol* 148(12):4072–4076, Jun. 15, 1992.

Yamamoto S, Mode of action of oligonucleotide fraction extracted from *Mycobacterium bovis* BCG. *Kekkaku* 69(9):29–32, 1994.

Yamamoto T et al., Ability of oligonucleotides with certain palindromes to induce interferon production and augment natural killer cell activity is associated with their base length. *Antisense Res Dev* 4:119–123, 1994.

Yamamoto T et al., Lipofection of synthetic oligodeoxyribonucleotide having a palindromic sequence AACGTT to murine splenocytes enhances interferon production and natural killer activity. *Microbiol Immunol* 38(10):831–836, 1994.

Yamamoto T et al., Synthetic oligonucleotides with certain palindromes stimulate interferon production of human peripheral blood lymphocytes in vitro. *Jpn J Cancer Res* 85:775–779, 1994.

Yaswen P et al., Effects of sequence of thioated oligonucleotides on cultured human mammary epithelial cells. *Antisense Res Dev* 3(1):67–77, 1993.

Yi, A–K et al., IFN–$\gamma$ promotes IL–6 and IgM secretion in response to CpG motifs in bacterial DNA and oligonucleotides. *J Immunol* 156(2):558–564, 1996.

Yi, A–K et al., Rapid immune activation by CpG motifs in bacterial DNA. *J Immunol* 157(12):5394–5402, 1996.

Zhao Q et al., Comparison of cellular binding and uptake of antisense phosphodiester, phosphorothioate, and mixed phosphorothioate and methylphosphonate oligonucleotides. *Antisense Res Dev* 3(1):53–66, Spring 1993.

Zhao Q et al., Stage–specific oligonucleotide uptake in murine bone marrow B–cell precursors. *Blood* 84(11):3660–6, Dec. 1, 1994.

* cited by examiner

Synthetic Oligonucleotides
↓ 5´-phosphorylation

↓ Annealing

5´ AAATTCGAAAGTACTGGACCTGTTAACA 3´
3´ TTTAAGCTTTCATGACCTGGACAATTGTGC 5´

SEQUENCE LISTING

```
<160> NUMBER OF SEQ ID NOS:  85

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
tccatgtcgt tcctgtcgtt                                              20

<210> SEQ ID NO 2
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 2
tcctgacgtt cctgacgtt                                               19

<210> SEQ ID NO 3
<211> LENGTH: 24
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (0)...(0)
<223> OTHER INFORMATION: Has a phosphorothioate backbone.

<400> SEQUENCE: 3
tcgtcgtttt gtcgttttgt cgtt                                         24

<210> SEQ ID NO 4
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 4
ccgtggatat ccgatgtacg ggccagatat                                   30

<210> SEQ ID NO 5
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 5
agtcgcggcc gcaatttcga taagccagta ag                                32
```

<210> SEQ ID NO 6
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 6
attctcgagt ctagactaga gctcgctgat cagcc                              35

<210> SEQ ID NO 7
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 7
attaggcctt ccccagcatg cctgctatt                                     29

<210> SEQ ID NO 8
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 8
tataggccct attttaaacg cgccctgtag cggcgca                            37

<210> SEQ ID NO 9
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 9
ctatggcgcc ttgggcccaa tttttgttaa atcagctc                           38

<210> SEQ ID NO 10
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 10
aaattcgaaa gtactggacc tgttaaca                                      28

<210> SEQ ID NO 11
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 11
cgtgttaaca ggtccagtac tttcgaattt                                    30

<210> SEQ ID NO 12
<211> LENGTH: 44
<212> TYPE: DNA
<213> ORGANISM: Artificial Sequence
<220> FEATURE:
<223> OTHER INFORMATION: synthetic oligonucleotide

```
<400> SEQUENCE: 12
gactccatga cgttcctgac gtttccatga cgttcctgac gttg                    44

<210> SEQ ID NO 13
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 13
gtccaacgtc aggaacgtca tggaaacgtc aggaacgtca tgga                    44

<210> SEQ ID NO 14
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 14
gacttcgtgt cgttcttctg tcgtctttag cgcttctcct gcgtgcgtcc cttg         54

<210> SEQ ID NO 15
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 15
gactcgtcgt tttgtcgttt tgtcgtttcg tcgttttgtc gttttgtcgt tg           52

<210> SEQ ID NO 16
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 16
gccctagtac tgttaacttt aaagggccc                                     29

<210> SEQ ID NO 17
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 17
ggcgggccct ttaaagttaa cagtactag                                     29

<210> SEQ ID NO 18
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 18
gccctggcgg ggataaggcg gggatttggc gggggataag gcggggaa                48

<210> SEQ ID NO 19
<211> LENGTH: 45
```

-continued

```
<212> TYPE: DNA
<213> ORGANISM: Artificial Sequence
<220> FEATURE:
<223> OTHER INFORMATION: synthetic oligonucleotide

<400> SEQUENCE: 19
ggcccccgcc ttatccccgc caaatccccg ccttatcccc gccag            45

<210> SEQ ID NO 20
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 20
gccctatttt aaattcgaaa gtactggacc tgttaaca                    38

<210> SEQ ID NO 21
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 21
cgtgttaaca ggtccagtac tttcgaattt aaaatag                     37

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
cgcgcgcgcg cgcgcgcgcg                                        20

<210> SEQ ID NO 23
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 23
gtctctagac agccactggt aacaggatt                              29

<210> SEQ ID NO 24
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 24
gtcgttgtgt cgtcaagtca gcgtaatgc                              29

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 25
```
tcgtttctgt aatgaaggag 20

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
aaggcagttc cataggatgg 20

<210> SEQ ID NO 27
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 27
tcgatctgcg attccaactc gtccaacatc aatac 35

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
tggtgagaat ggcaaaagtt 20

<210> SEQ ID NO 29
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 29
cattattcat tcgtgattgc g 21

<210> SEQ ID NO 30
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 30
acgtctcagg aacactgcca gcgc 24

<210> SEQ ID NO 31
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 31
agggatcgca gtggtgagta 20

<210> SEQ ID NO 32
<211> LENGTH: 21
<212> TYPE: DNA
<213> ORGANISM: Artificial Sequence -continued

```
<220> FEATURE:
<223> OTHER INFORMATION: synthetic oligonucleotide

<400> SEQUENCE: 32
tataaaatgc ttgatggtcg g                                          21

<210> SEQ ID NO 33
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 33
gggaagaggc ataaattctg tcagccagtt tagtc                           35

<210> SEQ ID NO 34
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 34
tggcttccca tacaagcgat                                            20

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
tacattatcg cgagcccatt                                            20

<210> SEQ ID NO 36
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 36
tggcctcgac gtttcccgt                                             19

<210> SEQ ID NO 37
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 37
atcgaattca gggcctcgtg atacgccta                                  29

<210> SEQ ID NO 38
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 38
tgacttgacg acacaacgac agctcatgac caaaatccc                       39
```

<210> SEQ ID NO 39
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 39
ctccttcatt acagaaacga cttttcaaa aatatggta                    39

<210> SEQ ID NO 40
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 40
ccatcctatg gaactgcctt ggtgagtttt ctccttc                     37

<210> SEQ ID NO 41
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 41
gagttggaat cgcagatcga taccaggatc ttgc                        34

<210> SEQ ID NO 42
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 42
aacttttgcc attctcacca gattcagtcg tcactca                     37

<210> SEQ ID NO 43
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 43
cgcaatcacg aatgaataat ggtttggttg atgcgagtg                   39

<210> SEQ ID NO 44
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 44
tggcagtgtt cctgagacgt ttgcattcga ttcctgtt                    38

<210> SEQ ID NO 45
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 45
tactcaccac tgcgatccct ggaaaaacag cattccag                38

<210> SEQ ID NO 46
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 46
ccgaccatca agcattttat acgtactcct gatgatgca                39

<210> SEQ ID NO 47
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 47
cagaatttat gcctcttccc accatcaagc attttatac                39

<210> SEQ ID NO 48
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 48
atcgcttgta tgggaagcca gatgcgccag agttgttt                38

<210> SEQ ID NO 49
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 49
aatgggctcg cgataatgta gggcaatcag gtgcgac                37

<210> SEQ ID NO 50
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 50
acgggaaacg tcgaggccac gattaaattc caacatgg                38

<210> SEQ ID NO 51
<211> LENGTH: 20
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (0)...(0)
<223> OTHER INFORMATION: Has a phosphorothioate backbone.

<400> SEQUENCE: 51
tccatgacgt tcctgacgtt                20

<210> SEQ ID NO 52
<211> LENGTH: 20
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (0)...(0)
<223> OTHER INFORMATION: Has a phosphorothioate backbone.

<400> SEQUENCE: 52
ggggtcaacg ttgaggggggg                                         20

<210> SEQ ID NO 53
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 53
tccaggactt tcctcaggtt                                          20

<210> SEQ ID NO 54
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 54
tccaggactt ctctcaggtt                                          20

<210> SEQ ID NO 55
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 55
cccccccccc cccccccccc                                          20

<210> SEQ ID NO 56
<211> LENGTH: 20
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (0)...(0)
<223> OTHER INFORMATION: Has phosphodiester  backbone.

<400> SEQUENCE: 56
tccatgacgt tcctgacgtt                                          20

<210> SEQ ID NO 57
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 57
ggcggcggcg gcggcggcgg                                          20

```
<210> SEQ ID NO 58
<211> LENGTH: 20
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (0)...(0)
<223> OTHER INFORMATION: Backbone is phosphorothioate--phosphodiester
      chimera

<400> SEQUENCE: 58
tccatgacgt tcctgacgtt                                                 20

<210> SEQ ID NO 59
<211> LENGTH: 20
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (0)...(0)
<223> OTHER INFORMATION: Has SOS-ODN backbone with two S-linkages
      at the 5' end, five S-linkages at the 3' end, and O-linkages
      in between.

<400> SEQUENCE: 59
ggggtcaacg ttgagggggg                                                 20

<210> SEQ ID NO 60
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 60
tctcccagcg tgcgccatat                                                 20

<210> SEQ ID NO 61
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 61
ggggtctgtg cttttggggg g                                               21

<210> SEQ ID NO 62
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 62 tcagggtgg ggggaacctt                                                  20

<210> SEQ ID NO 63
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 63
```
ggggttgacg ttttggggggg    20

<210> SEQ ID NO 64
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 64
tctagcgttt ttagcgttcc    20

<210> SEQ ID NO 65
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 65
tcgtcgttgt cgttgtcgtt    20

<210> SEQ ID NO 66
<211> LENGTH: 24
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (0)...(0)
<223> OTHER INFORMATION: Backbone is a phosphorothioate--phosphodiester
      chimera.

<400> SEQUENCE: 66
tcgtcgtttt gtcgttttgt cgtt    24

<210> SEQ ID NO 67
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 67
tcgtcgttgt cgttttgtcg tt    22

<210> SEQ ID NO 68
<211> LENGTH: 20
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (0)...(0)
<223> OTHER INFORMATION: Has a phosphodiester backbone.

<400> SEQUENCE: 68
tccatgacgt tcctgatgct    20

<210> SEQ ID NO 69
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 69

```
gcgttttttt ttgcg                                                    15

<210> SEQ ID NO 70
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 70
tccatgagct tcctgatgct                                               20

<210> SEQ ID NO 71
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 71
tccatgtcgt tcctgatgct                                               20

<210> SEQ ID NO 72
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 72
tccatgtcgt tcctgatgcg                                               20

<210> SEQ ID NO 73
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 73
tccatgtcgt tccgcgcgcg                                               20

<210> SEQ ID NO 74
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 74
tccatgtcgt tcctgccgct                                               20

<210> SEQ ID NO 75
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 75
gcggcgggcg gcgcgcgccc                                               20

<210> SEQ ID NO 76
<211> LENGTH: 20
<212> TYPE: DNA
<213> ORGANISM: Artificial Sequence
```

```
<220> FEATURE:
<223> OTHER INFORMATION: synthetic oligonucleotide

<400> SEQUENCE: 76
gcgcgcgcgc gcgcgcgcgc                                              20

<210> SEQ ID NO 77
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 77
ccggccggcc ggccggccgg                                              20

<210> SEQ ID NO 78
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 78
tccatgccgt tcctgccgtt                                              20

<210> SEQ ID NO 79
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 79
tccatgacgt tcctgatgct                                              20

<210> SEQ ID NO 80
<211> LENGTH: 1360
<212> TYPE: DNA
<213> ORGANISM: Artificial Sequence
<220> FEATURE:
<223> OTHER INFORMATION: plasmid DNA wild-type Kanamycin resistance gene

<400> SEQUENCE: 80
aagggcctcg tgatacgcct attttttatag gttaatgtca tgggggggg ggggaaagcc    60 acgttgtgtc tcaaaatctc tgatgttaca ttgcacaaga taaaaatata tcatcatgaa   120
caataaaact gtctgcttac ataaacagta atacaagggg tgttatgagc catattcaac   180
gggaaacgtc gaggccgcga ttaaattcca acatggatgc tgatttatat gggtataaat   240
gggctcgcga taatgtcggg caatcaggtg cgacaatcta tcgcttgtat gggaagcccg   300
atgcgccaga gttgtttctg aaacatggca aggtagcgt tgccaatgat gttacagatg   360
agatggtcag actaaactgg ctgacggaat ttatgcctct tccgaccatc aagcatttta   420
tccgtactcc tgatgatgca tggttactca ccactgcgat ccccggaaaa acagcattcc   480
aggtattaga agaatatcct gattcaggtg aaaatattgt tgatgcgctg gcagtgttcc   540
tgcgccggtt gcattcgatt cctgtttgta attgtccttt taacagcgat cgcgtatttc   600
gtctcgctca ggcgcaatca cgaatgaata cggtttggt tgatgcgagt gattttgatg   660
acgagcgtaa tggctggcct gttgaacaag tctggaaaga atgcataaa cttttgccat   720 tctcaccgga ttcagtcgtc actcatggtg atttctcact tgataacctt attttttgacg   780
```

```
agggggaaatt aataggttgt attgatgttg gacgagtcgg aatcgcagac cgataccagg    840
atcttgccat cctatggaac tgcctcggtg agttttctcc ttcattacag aaacggcttt    900
ttcaaaaata tggtattgat aatcctgata tgaataaatt gcagtttcat ttgatgctcg    960
atgagttttt ctaatcagaa ttggttaatt ggttgtaaca ctggcagagc attacgctga   1020
cttgacggga cggcgcaagc tcatgaccaa aatcccttaa cgtgagtttt cgttccactg   1080
agcgtcagac cccgtagaaa agatcaaagg atcttcttga gatcctttt ttctgcgcgt    1140 aatctgctgc ttgcaaacaa aaaaaccacc gctaccagcg gtggtttgtt tgccggatca   1200
agagctacca actcttttc cgaaggtaac tggcttcagc agagcgcaga taccaaatac    1260
tgttcttcta gtgtagccgt agttaggcca ccacttcaag aactctgtag caccgcctac   1320
atacctcgct ctgctaatcc tgttaccagt ggctgctgcc                          1360
```

<210> SEQ ID NO 81
<211> LENGTH: 1360
<212> TYPE: DNA
<213> ORGANISM: Artificial Sequence
<220> FEATURE:
<223> OTHER INFORMATION: plasmid DNA mutant Kanamycin resistance gene

<400> SEQUENCE: 81

```
aagggcctcg tgatacgcct atttttatag gttaatgtca tgggggggggg ggggaaagcc    60 acgttgtgtc tcaaaatctc tgatgttaca ttgcacaaga taaaaatata tcatcatgaa   120
caataaaact gtctgcttac ataaacagta atacaagggg tgttatgagc catattcaac   180
gggaaacgtc gaggccacga ttaaattcca acatggatgc tgatttatat gggtataaat   240
gggctcgcga taatgtaggg caatcaggtg cgacaatcta tcgcttgtat gggaagccag   300
atgcgccaga gttgtttctg aaacatggca aaggtagcgt tgccaatgat gttacagatg   360
agatggtcag actaaactgg ctgacagaat ttatgcctct tcccaccatc aagcatttta   420
tacgtactcc tgatgatgca tggttactca ccactgcgat ccctggaaaa acagcattcc   480
aggtattaga agaatatcct gattcaggtg aaaatattgt tgatgcgctg gcagtgttcc   540
tgagacgttt gcattcgatt cctgtttgta attgtccttt taacagcgat cgcgtatttc   600
gtctcgctca ggcgcaatca cgaatgaata atggtttggt tgatgcgagt gattttgatg   660
acgagcgtaa tggctggcct gttgaacaag tctggaaaga atgcataaa cttttgccat    720 tctcaccaga ttcagtcgtc actcatggtg atttctcact tgataacctt attttttgacg   780 agggggaaatt aataggttgt attgatgttg gacgagttgg aatcgcagat cgataccagg    840
atcttgccat cctatggaac tgccttggtg agttttctcc ttcattacag aaacgacttt     900
ttcaaaaata tggtattgat aatcctgata tgaataaatt gcagtttcat ttgatgctcg    960
atgagttttt ctaatcagaa ttggttaatt ggttgtaaca ctggcagagc attacgctga   1020
cttgacgaca caacgacagc tcatgaccaa aatcccttaa cgtgagtttt cgttccactg   1080
agcgtcagac cccgtagaaa agatcaaagg atcttcttga gatcctttt ttctgcgcgt    1140 aatctgctgc ttgcaaacaa aaaaaccacc gctaccagcg gtggtttgtt tgccggatca   1200
agagctacca actcttttc cgaaggtaac tggcttcagc agagcgcaga taccaaatac    1260
tgttcttcta gtgtagccgt agttaggcca ccacttcaag aactctgtag caccgcctac   1320
atacctcgct ctgctaatcc tgttaccagt ggctgctgcc                          1360
```

<210> SEQ ID NO 82
<211> LENGTH: 269

<212> TYPE: PRT
<213> ORGANISM: Artificial Sequence
<220> FEATURE:
<223> OTHER INFORMATION: mutant Kanamycin resistance gene

<400> SEQUENCE: 82

Met Ser His Ile Gln Arg Glu Thr Ser Arg Pro Arg Leu Asn Ser Asn
1               5                   10                  15
Met Asp Ala Asp Leu Tyr Gly Tyr Lys Trp Ala Arg Asp Asn Val Gly
            20                  25                  30
Gln Ser Gly Ala Thr Ile Tyr Arg Leu Tyr Gly Lys Pro Asp Ala Pro
        35                  40                  45
Glu Leu Phe Leu Lys His Gly Lys Gly Ser Val Ala Asn Asp Val Thr
    50                  55                  60
Asp Glu Met Val Arg Leu Asn Trp Leu Thr Glu Phe Met Pro Leu Pro
65                  70                  75                  80
Thr Ile Lys His Phe Ile Arg Thr Pro Asp Asp Ala Trp Leu Leu Thr
                85                  90                  95
Thr Ala Ile Pro Gly Lys Thr Ala Phe Gln Val Leu Glu Glu Tyr Pro
            100                 105                 110
Asp Ser Gly Glu Asn Ile Val Asp Ala Leu Ala Val Phe Leu Arg Arg
        115                 120                 125
Leu His Ser Ile Pro Val Cys Asn Cys Pro Phe Asn Ser Asp Arg Val
    130                 135                 140
Phe Arg Leu Ala Gln Ala Gln Ser Arg Met Asn Asn Gly Leu Val Asp
145                 150                 155                 160
Ala Ser Asp Phe Asp Asp Glu Arg Asn Gly Trp Pro Val Glu Gln Val
                165                 170                 175
Trp Lys Glu Met His Lys Leu Leu Pro Phe Ser Pro Asp Ser Val Val
            180                 185                 190
Thr His Gly Asp Phe Ser Leu Asp Asn Leu Ile Phe Asp Glu Gly Lys
        195                 200                 205
Leu Ile Gly Cys Ile Asp Val Gly Arg Val Gly Ile Ala Asp Arg Tyr
    210                 215                 220
Gln Asp Leu Ala Ile Leu Trp Asn Cys Leu Gly Glu Phe Ser Pro Ser
225                 230                 235                 240
Leu Gln Lys Arg Leu Phe Gln Lys Tyr Gly Ile Asp Asn Pro Asp Met
                245                 250                 255
Asn Lys Leu Gln Phe His Leu Met Leu Asp Glu Phe Phe
            260                 265

<210> SEQ ID NO 83
<211> LENGTH: 3987
<212> TYPE: DNA
<213> ORGANISM: Artificial Sequence
<220> FEATURE:
<223> OTHER INFORMATION: plasmid pUK21-A2

<400> SEQUENCE: 83
gaattcgagc tcccgggtac catggcatgc atcgatagat ctcgagtcta gactagagct      60
cgctgatcag cctcgactgt gccttctagt tgccagccat ctgttgtttg cccctcccccc    120 gtgccttcct tgaccctgga aggtgccact cccactgtcc tttcctaata aaatgaggaa     180
attgcatcgc attgtctgag taggtgtcat tctattctgg gggtggggt ggggcaggac      240 agcaagggggg aggattggga agacaatagc aggcatgctg ggaaggcct cggactagtg     300 gcgtaatcat ggtcatagct gtttcctgtg tgaaattgtt atccgctcac aattccacac    360

-continued

```
aacatacgag ccgcggaagc ataaagtgta aagcctgggg tgcctaatga gtgagctaac     420
tcacattaat tgcgttgcgc tcactgcccg ctttccagtc gggaaacctg tcgtgccagc     480
tgcattaatg aatcggccaa cgcgcgggga gaggcggttt gcgtattggg cgctcttccg     540
cttcctcgct cactgactcg ctgcgctcgg tcgttcggct gcggcgagcg gtatcagctc     600
actcaaaggc ggtaatacgg ttatccacag aatcagggga taacgcagga agaacatgt     660 gagcaaaagg ccagcaaaag gccaggaacc gtaaaaaggc cgcgttgctg gcgttttttcc    720 ataggctccg cccccctgac gagcatcaca aaaatcgacg ctcaagtcag aggtggcgaa     780
acccgacagg actataaaga taccaggcgt ttccccctgg aagctccctc gtgcgctctc     840
ctgttccgac cctgccgctt accggatacc tgtccgcctt tctcccttcg ggaagcgtgg     900
cgctttctca tagctcacgc tgtaggtatc tcagttcggt gtaggtcgtt cgctccaagc     960
tgggctgtgt gcacgaaccc cccgttcagc ccgaccgctg cgccttatcc ggtaactatc    1020
gtcttgagtc aacccggta agacacgact tatcgccact ggcagcagcc actggtaaca    1080
ggattagcag agcgaggtat gtaggcggtg ctacagagtt cttgaagtgg tggcctaact    1140
acggctacac tagaagaaca gtatttggta tctgcgctct gctgaagcca gttaccttcg    1200
gaaaaagagt tggtagctct tgatccggca acaaaccac cgctggtagc ggtggttttt    1260
ttgtttgcaa gcagcagatt acgcgcagaa aaaaggatc tcaagaagat cctttgatct    1320
tttctacggg gtctgacgct cagtggaacg aaaactcacg ttaagggatt ttggtcatga    1380
gcttgcgccg tcccgtcaag tcagcgtaat gctctgccag tgttacaacc aattaaccaa    1440
ttctgattag aaaaactcat cgagcatcaa atgaaactgc aatttattca tatcaggatt    1500
atcaatacca tatttttgaa aaagccgttt ctgtaatgaa ggagaaaact caccgaggca    1560
gttccatagg atggcaagat cctggtatcg gtctgcgatt ccgactcgtc caacatcaat    1620
acaacctatt aatttcccct cgtcaaaaat aaggttatca agtgagaaat caccatgagt    1680
gacgactgaa tccggtgaga atggcaaaag tttatgcatt tctttccaga cttgttcaac    1740
aggccagcca ttacgctcgt catcaaaatc actcgcatca accaaaccgt tattcattcg    1800
tgattgcgcc tgagcgagac gaaatacgcg atcgctgtta aaaggacaat acaaacagg    1860 aatcgaatgc aaccggcgca ggaacactgc cagcgcatca acaatatttt cacctgaatc    1920
aggatattct tctaatacct ggaatgctgt ttttccgggg atcgcagtgg tgagtaacca    1980
tgcatcatca ggagtacgga taaatgcttg atggtcgga gaggcataa attccgtcag    2040 ccagtttagt ctgaccatct catctgtaac atcattggca acgctacctt tgccatgttt    2100
cagaaacaac tctggcgcat cgggcttccc atacaagcga tagattgtcg cacctgattg    2160
cccgacatta tcgcgagccc atttataccc atataaatca gcatccatgt tggaatttaa    2220
tcgcggcctc gacgtttccc gttgaatatg gctcataaca cccttgtat tactgtttat    2280 gtaagcagac agttttattg ttcatgatga tatattttta tcttgtgcaa tgtaacatca    2340
gagattttga gacacaacgt ggctttcccc cccccccca tgacattaac ctataaaaat    2400
aggcgtatca cgaggccctt tcgtctcgcg cgtttcggtg atgacggtga aaacctctga    2460
cacatgcagc tcccggagac ggtcacagct tgtctgtaag cggatgccgg gagcagacaa    2520
gcccgtcagg gcgcgtcagc gggtgttggc gggtgtcggg gctggcttaa ctatgcggca    2580
tcagagcaga ttgtactgag agtgcaccat aaaattgtaa acgttaatat tttgttaaaa    2640
ttcgcgttaa attttgtta aatcagctca ttttttaacc aatagaccga atcggcaaa     2700
```

-continued

```
atcccttata aatcaaaaga atagcccgag atagagttga gtgttgttcc agtttggaac    2760
aagagtccac tattaaagaa cgtggactcc aacgtcaaag ggcgaaaaac cgtctatcag    2820
ggcgatggcc cacccgatt tagagcttga cggggaaagc cggcgaacgt ggcgagaaag     2880
gaagggaaga agcgaaagg agcgggcgct aaggcgctgg caagtgtagc ggtcacgctg     2940
cgcgtaacca ccacacccgc cgcgcttaat gcgccgctac agggcgcgta ctatggttgc    3000
tttgacgtat gcggtgtgaa ataccgcaca gatgcgtaag gagaaaatac cgcatcaggc    3060
gccattcgcc attcaggctg cgcaactgtt gggaagggcg atcggtgcgg gcctcttcgc    3120
tattacgcca gctggcgaaa gggggatgtg ctgcaaggcg attaagttgg gtaacgccag    3180
ggttttccca gtcacgacgt tgtaaaacga cggccagtga attgtaatac gactcactat    3240
agggcgaatt gggatcgat ccactagttc tagatccgat gtacgggcca gatatacgcg     3300
ttgacattga ttattgacta gttattaata gtaatcaatt acgggtcat tagttcatag     3360 cccatatatg gagttccgcg ttacataact tacggtaaat ggcccgcctg gctgaccgcc    3420
caacgacccc cgcccattga cgtcaataat gacgtatgtt cccatagtaa cgccaatagg    3480
gactttccat tgacgtcaat gggtggagta tttacggtaa actgcccact tggcagtaca    3540
tcaagtgtat catatgccaa gtacgccccc tattgacgtc aatgacggta aatggcccgc    3600
ctggcattat gcccagtaca tgaccttatg ggactttcct acttggcagt acatctacgt    3660
attagtcatc gctattacca tggtgatgcg gttttggcag tacatcaatg ggcgtggata    3720
gcggtttgac tcacggggat ttccaagtct ccaccccatt gacgtcaatg ggagtttgtt    3780
ttggcaccaa aatcaacggg actttccaaa atgtcgtaac aactccgccc cattgacgca    3840
aatgggcggt aggcgtgtac ggtgggaggt ctatataagc agagctctct ggctaactag    3900
agaacccact gcttactggc ttatcgaaat tgcggccgcc acggcgatat cggatccata    3960
tgacgtcgac gcgtctgcag aagcttc                                       3987
```

<210> SEQ ID NO 84
<211> LENGTH: 3987
<212> TYPE: DNA
<213> ORGANISM: Artificial Sequence
<220> FEATURE:
<223> OTHER INFORMATION: plasmid pGT

<400> SEQUENCE: 84

```
gaattcgagc tcccgggtac catggcatgc atcgatagat ctcgagtcta gactagagct      60
cgctgatcag cctcgactgt gccttctagt tgccagccat ctgttgtttg cccctccccc     120
gtgccttcct tgaccctgga agtgccact cccactgtcc tttcctaata aaatgaggaa      180
attgcatcgc attgtctgag taggtgtcat tctattctgg gggtgggt ggggcaggac       240 agcaaggggg aggattggga agacaatagc aggcatgctg gggaaggcct cggactagtg     300
ccggaatcat ggtcatagct gtttcctgtg tgaaattgtt atccgctcac aattccacac     360
aacatccggg ccgcggaagc ataaagtgta agcctgggg tgcctaatga gtgagctaac      420
tcacattaat tccgttccgc tcactgcccg ctttccagtc gggaaacctg ccgtgccagc     480
tgcattaatg aatcggccaa cgcgcgggga gagccggttt ccgtattggc cgctcttccg     540
cttcctcgct cactgactcg ctgcgctcgg tcgttcggct gcggcgagcg gtatcagctc     600
actcaaaggc ggtaatacgg ttatccacag aatcagggga taacgcagga aagaacatgt     660
gagcaaaagg ccagcaaaag gccaggaacc gtaaaaaggc cgcgttgctg gcgttttttcc    720 ataggctccg cccccctgac gagcatcaca aaaatcgacg ctcaagtcag aggtggcgaa    780
```

-continued

```
acccgacagg actataaaga taccaggcgt ttcccctgg aagctccctc gtgcgctctc    840
ctgttccgac cctgccgctt accggatacc tgtccgcctt tctcccttcg ggaagcgtgg    900
cgctttctca tagctcacgc tgtaggtatc tcagttcggt gtaggtcgtt cgctccaagc    960
tgggctgtgt gcacgaaccc cccgttcagc ccgaccgctg cgccttatcc ggtaactatc   1020
gtcttgagtc caacccggta agacacgact tatcgccact ggcagcagcc actggtaaca   1080
ggattagcag agcgaggtat gtaggcggtg ctacagagtt cttgaagtgg tggcctaact   1140
acggctacac tagaagaaca gtatttggta tctgcgctct gctgaagcca gttaccttcg   1200
gaaaaagagt tggtagctct tgatccggca acaaaccac cgctggtagc ggtggttttt    1260
ttgtttgcaa gcagcagatt acgcgcagaa aaaaggatc tcaagaagat cctttgatct    1320
tttctacggg gtctgacgct cagtggaacg aaaactcacg ttaagggatt ttggtcatga   1380
gcttgcgccg tcccgtcaag tcaccggaat gctctgccag tgttacaacc aattaaccaa   1440
ttctgattag aaaaactcat ccagcatcaa atgaaactgc aatttattca tatcaggatt   1500
atcaatacca tatttttgaa aaagccgttt ctgtaatgaa ggagaaaact caccgaggca   1560
gttccatagg atggcaagat cctggtatcg gtctgcaatt ccgactcggc aacatcaat   1620
acaacctatt aatttcccct catcaaaaat aaggttatca agtgagaaat caccatgagt   1680
aactactgaa tccggtgaga atggcaaaag tttatgcatt tctttccaga cttgttcaac   1740
aggccagcca ttacgctcat catcaaaatc ggaagcatca accaaaccgt tattcattcg   1800
ggattgagcc tgagccagac ggaatacgcg gtcgctgtta aaaggacaat tacaaacagg   1860
aatggaatgc aaccggcgga ggaacactgc cagagcatca acaatatttt cacctgaatc   1920
aggatattct tctaatacct ggaatgctgt ttttccgggg atagcagtgg tgagtaacca   1980
tgcatcatca ggagtacgga taaaatgctt gatggtcgga agaggcataa attccgtcag   2040
ccagtttagt ctgaccatct catctgtaac atcattggca acgctacctt tgccatgttt   2100
cagaaacaac tccggcgcgt cgggcttccc atacaagcgg tagattgtag cacctgattg   2160
cccgacatta tcgcgagccc atttatcccc atataaatca gcatccatgt tggaatttaa   2220
tcgcggcctg gaggtttccc gttgaatatg gctcataaca ccccttgtat tactgtttat   2280
gtaagcagac agttttattg ttcatgatga tatattttta tcttgtgcaa tgtaacatca   2340
gagattttga gacacaccgg ggctttcccc ccccccccca tgacattaac ctataaaaat   2400
agccgtatcc cgaggccctt ccgtctcgcg cgttccggtg atgccggtga aaacctctga   2460
cacatgcagc tcccggagac ggtcacagct tgtctgtaag cggatgccgg gagcagacaa   2520
gcccgtcagg gcgcgtcagc gggtgttggc gggtgtcggg gctggcttaa ctatgcggca   2580
tcagagcaga ttgtactgag agtgcaccat aaaattgtaa ccgttaatat tttgttaaaa   2640
ttcgcgttaa attttttgtta aatcagctca ttttttaacc aatagaccga atcggcaaa   2700
atcccttata aatcaaaaga atagcccgag atagagttga gtgttgttcc agtttggaac   2760
aagagtccac tattaaagac cgtggactcc accgtcaaag gccgaaaaac cgtctatcag   2820
gccgatggcc cacccgatt tagagcttga cggggaaagc cggcgcgcgt gccgagaaag   2880
gaagggaaga aaccgaaagg agcggccgct aagccgctgg caagtgtagc ggtcccgctg   2940
cgcgtaacca ccacacccgc cgcgcttaat ccgccgctac agggcgcgta ctatggttgc   3000
tttgccgtat gcggtgtgaa ataccgcaca gatccgtaag gagaaatac cgcatcagcc   3060
gccatccgcc attcaggctc cgcaactgtt gggaaggccg atcggtgcgg gcctctccgc   3120
```

-continued

```
tattccgcca gctgccgaaa gggggatgtg ctgcaagccg attaagttgg gtaccgccag    3180
ggttttccca gtcacggcgg tgtaaaccga cggccagtga attgtaatcc gactcactat    3240
aggccgaatt ggggaccgat ccactagttc tagatccgat gtacgggcca gatatacgcg    3300
ttgacattga ttattgacta gttattaata gtaatcaatt acgggtcat tagttcatag    3360 cccatatatg gagttccgcg ttacataact tacggtaaat ggcccgcctg gctgaccgcc    3420
caacgacccc cgcccattga cgtcaataat gacgtatgtt cccatagtaa cgccaatagg    3480
gactttccat tgacgtcaat gggtggagta tttacggtaa actgcccact tggcagtaca    3540
tcaagtgtat catatgccaa gtacgccccc tattgacgtc aatgacggta aatggcccgc    3600
ctggcattat gcccagtaca tgaccttatg ggactttcct acttggcagt acatctacgt    3660
attagtcatc gctattacca tggtgatgcg gttttggcag tacatcaatg ggcgtggata    3720
gcggtttgac tcacggggat ttccaagtct ccaccccatt gacgtcaatg ggagtttgtt    3780
ttggcaccaa aatcaacggg actttccaaa atgtcgtaac aactccgccc cattgacgca    3840
aatgggcggt aggcgtgtac ggtgggaggt ctatataagc agagctctct ggctaactag    3900
agaacccact gcttactggc ttatcgaaat tgcggccgcc acggcgatat cggatccata    3960
tgacgtcgac gcgtctgcag aagcttc                                        3987
```

<210> SEQ ID NO 85
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 85

```
tttaagcttt catgacctgg acaattgtgc                                       30
```

VECTORS AND METHODS FOR IMMUNIZATION OR THERAPEUTIC PROTOCOLS

RELATED APPLICATIONS

This application claims priority to US provisional patent application 60/047,209 filed May 20, 1997 and U.S. provisional patent application 60/047,233, filed May 20, 1997.

TECHNICAL FIELD

This invention relates generally to immune responses and more particularly to vectors containing immunostimulatory CpG motifs and/or a reduced number of neutralizing motifs and methods of use for immunization purposes as well as vectors containing neutralizing motifs and/or a reduced number of immunostimulatory CpG motifs and methods of use for gene therapy protocols.

BACKGROUND

Bacterial DNA, but not vertebrate DNA, has direct immunostimulatory effects on peripheral blood mononuclear cells (PBMC) in vitro (Messina et aL, *J. Immunol.* 147: 1759–1764, 1991; Tokanuga et al., *JNCI.* 72: 955, 1994). These effects include proliferation of almost all (>95%) B cells and increased immunoglobulin (Ig) secretion (Krieg et al., *Nature.* 374: 546–549, 1995). In addition to its direct effects on B cells, CpG DNA also directly activates monocytes, macrophages, and dendritic cells to secrete predominantly Th 1 cytokines, including high levels of IL-12 (Klinman, D., et al. *Proc. Natl. Acad. Sci. USA.* 93: 2879–2883 (1996); Halpern et al, 1996; Cowdery et al., *J. Immunol.* 156: 4570–4575 (1996). These cytokines stimulate natural killer (NK) cells to secrete γinterferon (IFN-γ) and to have increased lytic activity (Klinman et al., 1996, supra; Cowdery et al., 1996, supra; Yamamoto et al., *J. Immunol.* 148: 4072–4076 (1992); Ballas et al., *J. Immunol.* 157: 1840–1845 (1996)). These stimulatory effects have been found to be due to the presence of unmethylated CpG dinucleotides in a particular sequence context (CpG-S motifs) (Krieg et al., 1995, supra). Activation may also be triggered by addition of synthetic oligodeoxynucleotides (ODN) that contain CpG-S motifs (Tokunaga et al., *Jpn. J Cancer Res.* 79: 682–686 1988; Yi et al., *J. Immunol.* 156: 558–564, 1996; Davis et al., *J Immunol.* 160: 870–876, 1998).

Unmethylated CpG dinucleotides are present at the expected frequency in bacterial DNA but are under-represented and methylated in vertebrate DNA (Bird, *Trends in Genetics.* 3: 342–347, 1987). Thus, vertebrate DNA essentially does not contain CpG stimulatory (CpG-S) motifs and it appears likely that the rapid innnune activation in response to CpG-S DNA may have evolved as one component of the innate immune defense mechanisms that recognize structural patterns specific to microbial molecules.

Viruses have evolved a broad range of sophisticated strategies for avoiding host immune defenses. For example, nearly all DNA viruses and retroviruses appear to have escaped the defense mechanism of the mammalian immune system to respond to immunostimulatory CpG motifs. In most cases this has been accomplished through reducing their genomic content of CpG dinucleotides by 50–94% from that expected based on random base usage (Karlin et al., *J Virol.* 68: 2889–2897, 1994). CpG suppression is absent from bacteriophage, indicating that it is not an inevitable result of having a small genome. Statistical analysis indicates that the CpG suppression in lentiviruses is an evolutionary adaptation to replication in a eukaryotic host (Shaper et al., *Nucl. Acids Res.* 18: 5793–5797, 1990).

Nearly all DNA viruses and retroviruses appear to have evolved to avoid this defense mechanism through reducing their genomic content of CpG dinucleotides by 50–94% from that expected based on random base usage. CpG suppression is absent from bacteriophage, indicating that it is not an inevitable result of having a small genome. Statistical analysis indicates that the CpG suppression in lentiviruses is an evolutionary adaptation to replication in a eukaryotic host. Adenoviruses, however, are an exception to this rule as they have the expected level of genomic CpG dinucleotides. Different groups of adenovirae can have quite different clinical characteristics. Serotype 2 and 5 adenoviruses (Subgenus C) are endemic causes of upper respiratory infections and are notable for their ability to establish persistent infections in lymphocytes. These adenoviral serotypes are frequently modified by deletion of early genes for use in gene therapy applications, where a major clinical problem has been the frequent inflammatory immune responses to the viral particles. Serotype 12 adenovirus (subgenus A) does not establish latency, but can be oncogenic.

Despite high levels of unmethylated CpG dinucleotides, serotype 2 adenoviral DNA surprisingly is nonstimulatory and can actually inhibit activation by bacterial DNA. The arrangement and flanking bases of the CpG dinucleotides are responsible for this difference. Even though type 2 adenoviral DNA contains six times the expected frequency of CpG dinucleotides, it has CpG-S motifs at only one quarter of the frequency predicted by chance. Instead, most CpG motifs are found in clusters of direct repeats or with a C on the 5' side or a G on the 3' side. It appears that such CpG motifs are immune-neutralizing (CpG-N) in that they block the Th1-type immune activation by CpG-S motifs in vitro. Likewise, when CpG-N ODN and CpG-S are administered with antigen, the antigen-specific immune response is blunted compared to that with CpG-S alone. When CpG-N ODN alone is administered in vivo with an antigen, Th2-like antigen-specific immune responses are induced.

B cell activation by CpG-S DNA is T cell independent and antigen non-specific. However, B cell activation by low concentrations of CpG DNA has strong synergy with signals delivered through the B cell antigen receptor for both B cell proliferation and Ig secretion (Krieg et al., 1995, supra). This strong synergy between the B cell signaling pathways triggered through the B cell antigen receptor and by CpG-S DNA promotes antigen specific immune responses. The strong direct effects (T cell independent) of CpG-S DNA on B cells, as well as the induction of cytokines which could have indirect effects on B-cells via T-help pathways, suggests utility of CpG-S DNA as a vaccine adjuvant. This could be applied either to classical antigen-based vaccines or to DNA vaccines. CpG-S ODN have potent Th-1 like adjuvant effects with protein antigens (Chu et al., *J Exp. Med.* 186: 1623–1631 1997; Lipford et al., *Eur. J. Immunol.* 27: 2340–2344, 1997; Roman et al., *Nature Med.* 3: 849–854, 1997; Weiner et al., *Proc. Natl. Acad. Sci. USA.* 94: 10833, 1997; Davis et al., 1998, supra, Moldoveanu et al., A Novel Adjuvant for Systemic and Mucosal Immunization with Influenza Virus. *Vaccine* (in press) 1998).

SUMMARY OF THE INVENTION

The present invention is based on the discovery that removal of neutralizing motifs (e.g., CpG-N or poly G) from a vector used for immunization purposes, results in an antigen-specific immunostimulatory effect greater than with the starting vector. Further, when neutralizing motifs (e.g., CpG-N or poly G) are removed from the vector and stimulatory CpG-S motifs are inserted into the vector, the vector has even more enhanced immunostimulatory efficacy.

In a first embodiment, the invention provides a method for enhancing the immunostimulatory effect of an antigen encoded by nucleic acid contained in a nucleic acid construct including determining the CpG-N and CpG-S motifs present in the construct and removing neutralizing CpG (CpG-N) motifs and optionally inserting stimulatory CpG (CpG-S) motifs in the construct, thereby producing a nucleic acid construct having enhanced immunostimulatory efficacy. Preferably, the CpG-S motifs in the construct include a motif having the formula 5' $X_1CGX_2$ 3' wherein at least one nucleotide separates consecutive CpGs, $X_1$ is adenine, guanine, or thymine and $X_2$ is cytosine, thymine, or adenine.

In another embodiment, the invention provides a method for stimulating a protective or therapeutic immune response in a subject. The method includes administering to the subject an effective amount of a nucleic acid construct produced by determining the CpG-N and CpG-S motifs present in the construct and removing neutralizing CpG (CpG-N) motifs and optionally inserting stimulatory CpG (CpG-S) motifs in the construct, thereby producing a nucleic acid construct having enhanced immunostimulatory efficacy and stimulating a protective or therapeutic immune response in the subject. Preferably, the nucleic acid construct contains a promoter that functions in eukaryotic cells and a nucleic acid sequence that encodes an antigen to which the immune response is direct toward. Alternatively, an antigen can be admininstered simulataneously (e.g., admixture) with the nucleic acid construct.

In another embodiment, the invention provides a method for enhancing the expression of a therapeutic polypeptide in vivo wherein the polypeptide is encoded by a nucleic acid contained in a nucleic acid construct. The method includes determining the CpG-N and CpG-S motifs present in the construct, optionally removing stimulatory CpG (CpG-S) motifs and/or inserting neutralizing CpG (CpG-N) motifs, thereby producing a nucleic acid construct providing enhanced expression of the therapeutic polypeptide.

In yet another embodiment, the invention provides a method for enhancing the expression of a therapeutic polypeptide in vivo. The method includes administering to a subject a nucleic acid construct, wherein the construct is produced by determining the CpG-N and CpG-S motifs present in the construct and optionally removing stimulatory CpG (CpG-S) motifs and/or inserting neutralizing CpG (CpG-N) motifs, thereby enhancing expression of the therapeutic polypeptide in the subject.

BRIEF DESCRIPTION OF THE DRAWINGS

FIG. 4A and 4B are a schematic diagrams of the construction of pMAS.

DETAILED DESCRIPTION OF THE INVENTION

Figure 1A:
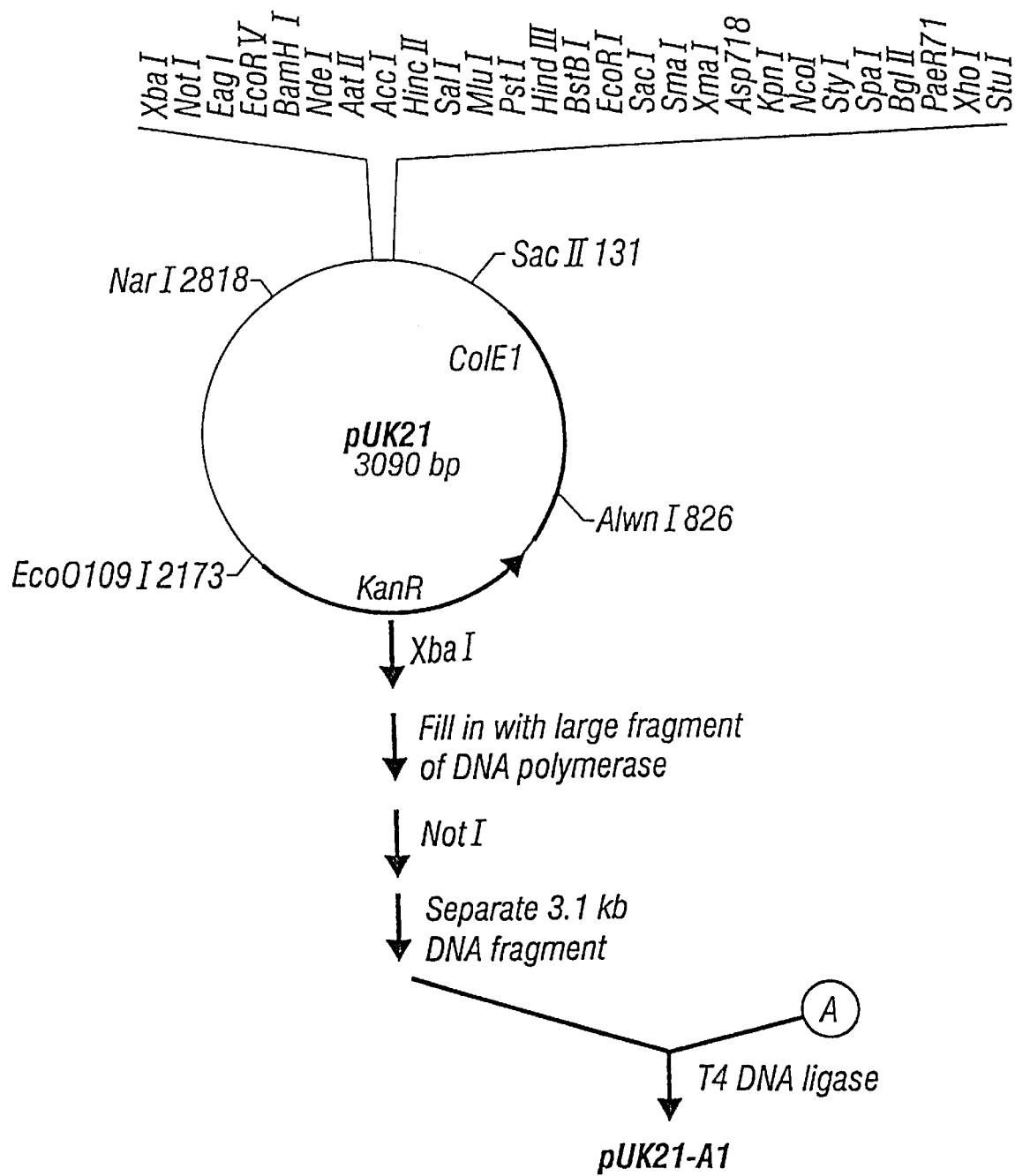
FIG. 1A and 1B are a schematic diagrams of the construction of pUK21-A1.

The present invention provides vectors for immunization or therapeutic purposes based on the presence or absence of CpG dinucleotide immunomodulating motifs. For immunization purposes, inunostimulatoxy motifs (CpG-S) are desirable while immunoinhibitory CpG motifs (CpG-N) are undesirable, whereas for gene therapy purposes, CpG-N are desirable and CpG-S are undesirable. Plasmid DNA expression cassettes were designed using CpG-S and CpG-N motifs. In the case of DNA vaccines, removal of CpG-N motifs and addition of CpG-S motifs should allow induction of a more potent and appropriately directed immune response. The opposite approach with gene therapy vectors, namely the removal of CpG-S motifs and addition of CpG-N motifs, allows longer lasting therapeutic effects by abrogating immune responses against the expressed protein.

DNA vaccines

DNA vaccines have been found to induce potent humoral and cell-mediated immune responses. These are frequently Th1-like, especially when the DNA is administered by intramuscular injection (Davis, H. L. (1998) Gene-based Vaccines. In: Advanced Gene Delivery: From Concepts to Pharmaceutical Products (Ed. A. Rolland), Harwood Academic Publishers (in press); Donnelly et al., Life Sciences 60:163, 1997; Donnelly et al., Ann Rev. Immunol. 15:617, 1997; Sato et al., Science 273:352, 1996). Most DNA vaccines comprise antigen-expressing plasmid DNA vectors. Since such plasmids are produced in bacteria and then purified, they usually contain several unmethylated immunostimulatory CpG-S motifs. There is now convincing evidence that the presence of such motifs is essential for the induction of immune responses with DNA vaccines (see Krieg et al., Trends Microbiology. 6: 23–27, 1998). For example, it has been shown that removal or methylation of potent CpG-S sequences from plasmid DNA vectors reduced or abolished the in vitro production of Th1 cytokines (e.g., IL-12, IFN-α, IFN-γ) from monocytes and the in vivo antibody and CTL response against an encoded antigen (β-galactosidase) (Sato et al., 1996, supra; Klimnan et al., J. Immunol 158: 3635–3639 (1997). Potent responses could be restored by cloning CpG-S motifs back into the vectors (Sato et al., 1996, supra) or by coadministering CpG-S ODN (Klinan et al., 1997, supra). The humoral response in monkeys to a DNA vaccine can also be augmented by the addition of E. coli DNA (Gramzinski et al., Molec. Med. 4: 109–119, 1998). It has also been shown that the strong Th1 cytokine pattern induced by DNA vaccines can be obtained with a protein vaccine by the coadministration of empty plasmid vectors (Leclerc et al., Cell Immunology. 170: 97–106, 1997).

The present invention shows that DNA vaccine vectors can be improved by removal of CpG-N motifs and further improved by the addition of CpG-S motifs. In addition, for high and long-lasting levels of expression, the optimized vector should preferably include a promoter/enhancer, which is not down-regulated by the cytokines induced by the immunostimulatory CpG motifs.

It has been shown that the presence of unmethylated CpG motifs in the DNA vaccines is essential for the induction of immune responses against the antigen, which is expressed only in very small quantities (Sato et al., 1996, Klinman et al., 1997, supra). As such, the DNA vaccine provides its own adjuvant in the form of CpG DNA. Since single-stranded but not double-stranded DNA can induce immunostimulation in vitro, the CpG adjuvant effect of DNA vaccines in vivo is likely due to oligonucleotides resulting from plasmid degradation by nucleases. Only a small portion of the plasmid DNA injected into a muscle actually enters a cell and is expressed; the majority of the plasmid is degraded in the extracellular space.

The present invention provides DNA vaccine vectors further improved by removal of undesirable immunoinhibitory CpG motifs and addition of appropriate CpG immunostimulatory sequences in the appropriate number and spacing. The correct choice of immunostimulatory CpG motifs could allow one to preferentially augment humoral or CTL responses, or to preferentially induce certain cytokines.

The optimized plasmid cassettes of the invention are ready to receive genes encoding any particular antigen or group of antigens or antigenic epitopes. One of skill in the art can create cassettes to preferentially induce certain types of immunity, and the choice of which cassette to use would depend on the disease to be immunized against.

The exact immunostimulatory CpG motif(s) to be added will depend on the ultimate purpose of the vector. If it is to be used for prophylactic vaccination, preferable motifs stimulate humoral and/or cell-mediated immunity, depending on what would be most protective for the disease in question. It the DNA vaccine is for therapeutic purposes, such as for the treatment of a chronic viral infection, then motifs which preferentially induce cell-mediated immunity and/or a particular cytokine profile is added to the cassette.

The choice of motifs also depends on the species to be immunized as different motifs are optimal in different species. Thus, there would be one set of cassettes for humans as well as cassettes for different companion and food-source animals which receive veterinary vaccination. There is a very strong correlation between certain in vitro immunostimulatory effects and in vivo adjuvant effect of specific CpG motifs. For example, the strength of the humoral response correlates very well (r>0.9) with the in vitro induction of TNF-$\alpha$, IL-6, IL-12 and B-cell proliferation. On the other hand, the strength of the cytotoxic T-cell response correlates well with in vitro induction of IFN-$\gamma$.

Since the entire purpose of DNA vaccines is to enhance immune responses, which necessarily includes cytokines, the preferred promoter is not down-regulated by cytokines. For example, the CMV immediate-early promoter/enhancer, which is used in almost all DNA vaccines today, is turned off by IFN-$\alpha$ and IFN-$\gamma$ (Gribaudo et al., Virology. 197: 303–311, 1993; Harms & Splitter, *Human Gene Ther*. 6: 1291–1297, 1995; Xiang et al., Vaccine, 15: 896–898, 1997). Another example is the down-regulation of a hepatitis B viral promoter in the liver of HBsAg-expressing transgenic mice by IFN-$\gamma$ and TNF-$\alpha$ (Guidotti et al., *Proc. Natl. Acad. Sci. USA*. 91: 3764–3768, 1994).

Nevertheless, such viral promoters may still be used for DNA vaccines as they are very strong, they work in several cell types, and despite the possibility of promoter turn-off, the duration of expression with these promoters has been shown to be sufficient for use in DNA vaccines (Davis et al., *Human Molec. Genetics*. 2: 1847–1851, 1993). The use of CpG-optimized DNA vaccine vectors could improve immune responses to antigen expressed for a limited duration, as with these viral promoters. When a strong viral promoter is desired, down-regulation of expression may be avoidable by choosing CpG-S motfis that do not induce the cytokine(s) that affect the promoter (Harms and Splitter, 1995 supra).

Other preferable promoters for use as described herein are eukaryotic promoters. Such promoters can be cell- or tissue-specific. Preferred cells/tissues for high antigen expression are those which can act as professional antigen presenting cells (APC) (e.g. macrophages, dendritic cells), since these have been shown to be the only cell types that can induce immune responses following DNA-based immunization (Ulmer et al., 1996; Corr et al., *J Exp. Med.*, 184, 1555–1560, 1996; Doe et al., *Proc. Natl. Acad. Sci. USA*, 93, 8578–8583, 1996; Iwasaki et al., *J. Immunol.*, 159: 11–141998). Examples of such a promoter are the mammalian MHC I or MHC II promoters.

The invention also includes the use of a promoter whose expression is up-regulated by cytokines. An example of this is the mammalian MHC I promoter that has the additional advantage of expressing in APC, which as discussed above is highly desirable. This promoter has also been shown to have enhanced expression with IFN-$\gamma$ (Harms & Splitter, 1995, supra).

After intramuscular injection of DNA vaccines, muscle fibers may be efficiently transfected and produce a relatively large amount of antigen that may be secreted or otherwise released (e.g., by cytolytic attack on the antigen-expressing muscle fibers) (D)avis et al., *Current Opinions Biotech*. 8: 635–640, 1997). Even though antigen-expressing muscle fibers do not appear to induce immune responses from the point of view of antigen presentation, B-cells must meet circulating antigen to be activated, it is possible that antibody responses are augmented by antigen secreted or otherwise released from other cell types (e.g., myofibers, keratinocytes). This may be particularly true for conformational B-cell epitopes, which would not be conserved by peptides presented on APC. For this purpose, expression in muscle tissue is particularly desirable since myofibers are post-mitotic and the vector will not be lost through cell-division, thus antigen expression can continue until the antigen-expressing cell is destroyed by an immune repsonse against it. Thus, when strong humoral responses are desired, other preferred promoters are strong muscle-specific promoters such as the human muscle-specific creatine kinase promoter (Bartlett et al., 1996) and the rabbit $\beta$-cardiac myosin heavy chain (full-length or truncated to 781 bp) plus the rat myosin light chain 1/3 enhancer.

In the case of DNA vaccines with muscle- or other non-APC tissue-specific promoters, it may be preferable to administer it in conjunction with a DNA vaccine encoding the same antigen but under the control of a promoter that will work strongly in APC (e.g., viral promoter or tissue specific for APC). In this way, optimal immune responses can be obtained by having good antigen presentation as well as sufficient antigen load to stimulate B-cells. A hybrid construct, such as the $\beta$-actin promoter with the CMV enhancer (Niwa et al, Gene. 108: 193–199, 1991) is also desirable to circumvent some of the problems of strictly viral promoters.

While DNA vaccine vectors may include a signal sequence to direct secretion, humoral and cell-mediated responses are possible even when the antigen is not secreted. For example, it has been found in mice immunized with hepatitis B surface antigen (HBsAg)-expressing DNA that the appearance of anti-HBs antibodies is delayed for a few weeks if the HBsAg is not secreted (Michel et a., 1995). As well, antibodies are induced in rabbits following IM immunization with DNA containing the gene for cottontail rabbit papilloma virus major capsid protein (L1), which has a nuclear localization signal (Donnelly et al., 1996). In these cases, the B-cells may not be fully activated until the expressed antigen is released from transfected muscle (or other) cells upon lysis by antigen-specific CTL.

Preferably, the CpG-S motifs in the construct include a motif having the formula:

5'$X_1$CG$X_2$3' wherein at least one nucleotide separates consecutive CpGs, $X_1$ is adenine, guanine, or thymine and $X_2$ is cytosine, thymine, or adenine. Exemplary CpG-S oligonucleotide motifs include GACGTT, AGCGTT, AACGCT, GTCGTT and AACGAT. Another oligonucleotide useful in the construct contains TCAACGTT. Further exemplary oligonucleotides of the invention contain GTCG(T/C)T, TGACGTT, TGTCG(T/C)T, TCCATGTCGTTCCTGTCGTT (SEQ ID NO:1), TCCTGACGTTCCTGACGTT (SEQ ID NO:2) and TCGTCGTTTTGTCGTTTTGTCGTT (SEQ ID NO:3).

Preferably CpG-N motifs contain direct repeats of CpG dinucleotides, CCG trinucleotides, CGG trinucleotides, CCGG tetranucleotides, CGCG tetranucleotides or a combination of any of these motifs. In addition, the neutralizing motifs of the invention may include oligos that contain a sequence motif that is a poly-G motif, which may contain at least about four Gs in a row or two G trimers, for example (Yaswen et al., *Antisense Research and Development* 3:67, 1993; Burgess et al., *PNAS* 92:4051, 1995).

In the present invention, the nucleic acid construct is preferably an expression vector. The term "expression vector" refers to a plasmid, virus or other vehicle known in the art that has been manipulated by insertion or incorporation of genetic coding sequences. Polynucleotide sequence which encode polypeptides can be operatively linked to expression control sequences.

"Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The term "control sequences" is intended to include, at a minimum, components whose presence can influence expression, and can also include additional components whose presence is advantageous, for example, leader sequences and fusion partner sequences. Expression control sequences can include a promoter.

The nucleic acid construct of the invention may include any of a number of suitable transcription and translation elements, including constitutive and inducible promoters, transcription enhancer elements, transcription terminators, etc. may be used in the expression vector (see e.g., Bitter et al., 1987, Methods in Enzymology 153:516–544). When cloning in mammalian cell systems, promoters derived from the genome of mammalian cells (e.g., metallothionein promoter) or from mammalian viruses (e.g. the retrovirus long terminal repeat; the adenoviral late promoter; the vaccinia virus 7.5K promoter) may be used. Promoters produced by recombinant DNA or synthetic techniques may also be used to provide for transcription of the inserted polypeptide coding sequence.

Mammalian cell systems which utilize recombinant viruses or viral elements to direct expression may be engineered. For example, when using adenovirus expression vectors, the polypeptide coding sequence may be ligated to an adenovirus transcription/translation control complex, e.g., the late promoter and tripartite leader sequence. Alternatively, the vaccinia virus 7.5K promoter may be used. (e.g., see, Mackett et al., 1982, *Proc. Natl. Acad. Sci. USA* 79: 7415–7419; Mackett et al., 1984, *J. Virol.* 49: 857–864; Panicali et al., 1982, *Proc. Natl. Acad. Sci. USA* 79: 4927–4931). Of particular interest are vectors based on bovine papilloma virus which have the ability to replicate as extrachromosomal elements (Sarver, et al., 1981, *Mol. Cell. Biol.* 1: 486). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the gene of interest in host cells (Cone & Mulligan, 1984, *Proc. Natl. Acad. Sci. USA* 81:6349–6353). High level expression may also be achieved using inducible promoters, including, but not limited to, the metallothionine IIA promoter and heat shock promoters.

The polypeptide that acts as an antigen in the methods described herein refers to an immunogenic polypeptide antigen, group of antigens or peptides encoding particular epitopes. A polynucleotide encoding such antigen(s) is inserted into the nucleic acid construct as described herein. For example, a nucleic acid sequence encoding an antigenic polypeptide derived from a virus, such as Hepatitis B virus (HBV) (e.g. HBV surface antigen), an antigen derived from a parasite, from a tumor, or a bacterial antigen, is cloned into the nucleic acid construct described herein. Virtually any antigen, groups of antigens, or antigenic epitopes, can be used in the construct. Other antigens, such as peptides that mimic nonpeptide antigens, such as polysaccharides, are included in the invention.

Gene transfer into eukaryotic cells can be carried out by direct (in vivo) or indirect (in vitro or ex vivo) means (Miller et al., A. D. *Nature*. 357: 455–460, 1992). The DNA vector can also be transferred in various forms and formulations. For example, pure plasmid DNA in an aqueous solution (also called "naked" DNA) can be delivered by direct gene transfer. Plasmid DNA can also be formulated with cationic and neutral lipids (liposomes) (Gregoriadis et al, 1996), microencapsulated (Mathiowitz et al., 1997), or encochleated (Mannino and Gould Fogerite, 1995) for either direct or indirect delivery. The DNA sequences can also be contained within a viral (e.g., adenoviral, retroviral, herpesvius, pox virus) vector, which can be used for either direct or indirect delivery.

DNA vaccines will preferably be administered by direct (in vivo) gene transfer. Naked DNA can be give by intramuscular (Davis et al., 1993), intradermal (Raz et al., 1994; Condon et al., 1996; Gramzinski et al., 1998), subcutaneous, intravenous (Yokoyama et al., 1996; Liu et al., 1997), intraaterial (Nabel et al., 1993) or buccal injection (Etchart et al., 1997; Hinkula et al., 1997). Plasmid DNA may be coated onto gold particles and introduced biolistically with a "gene-gun" into the epidermis if the skin or the oral or vaginal mucosae (Fynan et al *Proc. Natl. Acad. Sci. USA* 90:11478, 1993; Tang et al, *Nature* 356:152, 1992; Fuller, et al, *J. Med. Primatol.* 25:236, 1996; Keller et al., *Cancer Gene Ther.*, 3:186, 1996). DNA vaccine vectors may also be used in conjunction with various delivery systems. Liposomes have been used to deliver DNA vaccines by intramuscular injection (Gregoriadis et al, *FEBS Lett*.402:107, 1997) or into the respiratory system by non-invasive means such as intranasal inhalation (Fynan et al., supra). Other potential delivery systems include microencapsulation (Jones et al., 1998; Mathiowitz et al., 1997) or cochleates (Mannino et al., 1995, Lipid matrix-based vaccines for mucosal and systemic immunization. Vaccine Designs: The Subunit and Adjuvant Approach, M. F. Powell and M. J. Newman, eds., Pleum Press, New York, 363–387), which can be used for parenteral, intranasal (e.g., nasal spray) or oral (e.g., liquid, gelatin capsule, solid in food) delivery. DNA vaccines can also be injected directly into tumors or directly into lymphoid tissues (e.g., Peyer's patches in the gut wall). It is also possible to formulate the vector to target delivery to certain cell types, for example to APC. Targeting to APC such as dendritic cells is possible through attachment of a mannose moiety (dendritic cells have a high density of mannose receptors) or a ligand for one of the other receptors found preferentially on APC. There is no limitation as to the route that the DNA vaccine is delivered, nor the manner in which it is formulated as long as the cells that are transfected can express antigen in such a way that an immune response is induced.

It some cases it may be desirable to carry out ex-vivo gene transfer, in which case a number a methods are possible including physical methods such as micro injection, electroportion or calcium phosphate precipitation, or facilitated transfer methods such as liposomes or dendrimers, or through the use of viral vectors. In this case, the transfected cells would be subsequently administered to the subject so that the antigen they expressed could induce an immune response.

Nucleotide sequences in the nucleic acid construct can be intentionally manipulated to produce CpG-S sequences or to reduce the number of CpG-N sequences for immunization vectors. For example, site-directed mutagenesis can be utilized to produce a desired CpG motif. Alternatively, a particular CpG motif can be synthesized and inserted into the nucleic acid construct. Further, one of skill in the art can produce double-stranded CpG oligos that have self-complementary ends that can be ligated together to form long chains or concatemers that can be ligated into a plasmid, for example. It will be apparent that the number of CpG motifs or CpG-containing oligos that can be concatenated will depend on the length of the individual oligos and can be readily determined by those of skill in the art without undue experimentation. After formation of concatemers, multiple oligos can be cloned into a vector for use in the methods of the invention.

In one embodiment, the invention provides a method for stimulating a protective immune response in a subject. The method includes administering to the subject an immunomostimulatory effective amount of a nucleic acid construct produced by removing neutralizing CpG (CpG-N) motifs and optionally inserting stimulatory CpG (CpG-S) motifs, thereby producing a nucleic acid construct having enhanced immunostimulatory efficacy and stimulating a protective immune response in the subject. The construct typically further includes regulatory sequences for expression of DNA in eukaryotic cells and nucleic acid sequences encoding at least one polypeptide.

It is envisioned that methods of the present invention can be used to prevent or treat bacterial, viral, parasitic or other disease states, including tumors, in a subject. The subject can be a human or may be a non-human such as a pig, cow, sheep, horse, dog, cat, fish, chicken, for example. Generally, the terms "treating," "treatment," and the like are used herein to mean obtaining a desired pharmacologic and/or physiologic effect. The effect may be prophylactic in terms of completely or partially preventing a particular infection or disease (e.g. bacterial, viral or parasitic disease or cancer) or sign or symptom thereof, and/or may be therapeutic in terms of a partial or complete cure for an infection or disease and/or adverse effect attributable to the infection or disease. "Treating" as used herein covers any treatment of (e.g. complete or partial), or prevention of, an infection or disease in a non-human, such as a mammal, or more particularly a human, and includes:

(a) preventing the disease from occurring in a subject that may be at risk of becoming infected by a pathogen or that may be predisposed to a disease (e.g., cancer) but has not yet been diagnosed as having it;

(b) inhibiting the infection or disease, i.e., arresting its development; or (c) relieving or ameliorating the infection or disease, i.e., cause regression of the infection or disease.

Delivery of polynucleotides can be achieved using a plasmid vector as described herein, that can be administered as "naked DNA" (i.e., in an aqueous solution), formulated with a delivery system (e.g., liposome, cochelates, microencapsulated), or coated onto gold particles. Delivery of polynucleotides can also be achieved using recombinant expression vectors such as a chimeric virus. Thus the invention includes a nucleic acid construct as described herein as a pharmaceutical composition useful for allowing transfection of some cells with the DNA vector such that antigen will be expressed and induce a protective (to prevent infection) or a therapeutic (to ameliorate symptoms attributable to infection or disease) immune response. The pharmaceutical compositions according to the invention are prepared by bringing the construct according to the present invention into a form suitable for administration to a subject using solvents, carriers, delivery systems, excipients, and additives or auxiliaries. Frequently used solvents include sterile water and saline (buffered or not). A frequently used carrier includes gold particles, which are delivered biolistically (i.e., under gas pressure). Other frequently used carriers or delivery systems include cationic liposomes, cochleates and microcapsules, which may be given as a liquid, solution, enclosed within a delivery capsule or incorporated into food.

The pharmaceutical compositions are preferably prepared and administered in dose units. Liquid dose units would be injectable solutions or nasal sprays or liquids to be instilled (e.g., into the vagina) or swallowed or applied onto the skin (e.g., with allergy tines, with tattoo needles or with a dermal patch). Solid dose units would be DNA-coated gold particles, creams applied to the skin or formulations incorporated into food or capsules or embedded under the skin or mucosae or pressed into the skin (e.g., with allergy tines). Different doses will be required depending on the activity of the compound, form and formulation, manner of administration, and age or size of patient (i.e., pediatric versus adult), purpose (prophylactic vs therapeutic). Doses will be given at appropriate intervals, separated by weeks or months, depending on the application. Under certain circumstances higher or lower, or more frequent or less frequent doses may be appropriate. The administration of a dose at a single time point may be carried out as a single administration or a multiple administration (e.g., several sites with gene-gun or for intradermal injection or different routes). Whether the pharmaceutical composition is delivered locally or systemically, it will induce systemic immune responses. By "therapeutically effective dose" is meant the quantity of a vector or construct according to the invention necessary to induce an immune response that can prevent, cure, or at least partially arrest the symptoms of the disease and its complications. Amounts effective for this will of course depend on the mode of administration, the age of the patient (pediatric versus adult) and the disease state of the patient. Animal models may be used to determine effective doses for the induction of particular immune responses and in some cases for the prevention or treatment of particular diseases.

The term "effective amount" of a nucleic acid molecule refers to the amount necessary or sufficient to realize a desired biologic effect. For example, an effective amount of a nucleic acid construct containing at least one unmethylated CpG for treating a disorder could be that amount necessary to induce an immune response of sufficient magnitude to eliminate a tumor, cancer, or bacterial, parasitic, viral or flngal infection. An effective amount for use as a vaccine could be that amount useful for priming and boosting a protective immune response in a subject. The effective amount for any particular application can vary depending on such factors as the disease or condition being treated, the particular nucleic acid being administered (e.g. the number of unmethylated CpG motifs (-S or -N) or their location in the nucleic acid), the size of the subject, or the severity of the disease or condition. One of ordinary skill in the art can empirically determine the effective amount of a particular oligonucleotide without necessitating undue experimentation. An effective amount for use as a prophylactic vaccine is that amount useful for priming and boosting a protective immune response in a subject.

In one embodiment, the invention provides a nucleic acid construct containing CpG motifs as described herein as a pharmaceutical composition useful for inducing an immune response to a bacterial, parasitic, fingal, viral infection, or the like, or to a tumor in a subject, comprising an immunologically effective amount of nucleic acid construct of the invention in a pharmaceutically acceptable carrier. "Administering" the pharmaceutical composition of the present invention may be accomplished by any means known to the skilled artisan. By "subject" is meant any aninal, preferably a mammal, most preferably a human. The term "immunogenically effective amount," as used in describing the invention, is meant to denote that amount of nucleic acid construct which is necessary to induce, in an animal, the production of a protective immune response to the bacteria, fungus, virus, tumor, or antigen in general.

In addition to the diluent or carrier, such compositions can include adjuvants or additional nucleic acid constructs that express adjuvants such as cytokines or co-stimulatory molecules. Adjuvants include CpG motifs such as those described in co-pending application Ser. No. 09/030,701.

The method of the invention also includes slow release nucleic acid delivery systems such as microencapsulation of the nucleic acid constructs or incorporation of the nucleic acid constructs into liposomes. Such particulate delivery systems may be taken up by the liver and spleen and are easily phagocytosed by macrophages. These delivery systems also allow co-entrapment of other immunomodulatory molecules, or nucleic acid constructs encoding other immunomodulatory molecules, along with the antigen-encoding nucleic acid construct, so that modulating molecules may be delivered to the site of antigen synthesis and antigen processing, allowing modulation of the immune system towards protective responses.

Many different techniques exist for the timing of the immunizations when a multiple immunization regimen is utilized. It is possible to use the antigenic preparation of the invention more than once to increase the levels and diversity of expression of the immune response of the immunized animal. Typically, if multiple immunizations are given, they will be spaced about four or more weeks apart. As discussed, subjects in which an immune response to a pathogen or cancer is desirable include humans, dogs, cattle, horses, deer, nice, goats, pigs, chickens, fish, and sheep.

Examples of infectious virus to which stimulation of a protective immune response is desirable include: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g. influenza viruses); Bungaviridae (e.g., Hantaan viruses, bunga viruses, phleboviruses and Nairo viruses); Arena viridae (hemorrhagic fever viruses); Reoviridae (erg., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxviridae (variola viruses, vaccinia viruses, pox viruses); and Iridoviridae (e.g. African swine fever virus); and unclassified viruses (e.g., the etiological agents of Spongiform encephalopathies, the agent of delta hepatities (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria to which stimulation of a protective immune response is desirable include: *Helicobacter pyloris, Borellia burgdorferi, Legionella pneumophilia*, Mycobacteria sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), Streptococcus (viridans group), *Streptococcus faecalis, Streptococcus bovis*, Streptococcus (anaerobic sps.), *Streptococcus pneumoniae*, pathogenic *Campylobacter*sp., Enterococcus sp., *Haemophilus influenzae, Bacillus antracis, corynebacterium diphtheriae*, corynebacterium sp., *Erysipelothrix rhusiopathiae, Clostridium perfringers, Clostridium tetani, Enterobacter aerogenes, Klebsiella pneumoniae, Pasturella multocida*, Bacteroides sp., *Fusobacterium nucleatum, Streptobacillus moniliformis, Treponema pallidium, Treponema pertenue*, Leptospira, and *Actinomyces israelii*.

Examples of infectious fungi to which stimulation of a protective immune response is desirable include: *Cryptococcus neoformans, Histoplasma capsulatum, Coccidioides immitis, Blastomyces dermatitidis,Chlamydia trachomatis, Candida albicans*. Other infectious organisms (i.e., protists) include: *Plasmodium falciparum* and *Toxoplasma gondii*.

An "immunostimulatory nucleic acid molecule" or oligonucleotide as used herein refers to a nucleic acid molecule, which contains an unmethylated cytosine, guanine dinucleotide sequence (i.e. "CpG DNA" or DNA containing a cytosine followed by guanosine and linked by a phosphate bond) and stimulates (e.g. has a mitogenic effect on, or induces or increases cytokine expression by) a vertebrate lymphocyte. An immunostimulatory nucleic acid molecule can be double-stranded or single-stranded. Generally, double-stranded molecules are more stable in vivo, while single-stranded molecules may have increased immune activity.

Unmethylated immunostimulatory CpG motifs, either within a nucleic acid construct or an oligonucleotide, directly activate lymphocytes and co-stimulate antigen-specific responses. As such, they are fundamentally different form aluminum precipitates (alum), currently the only adjuvant licensed for human use, which is thought to act largely through adsorbing the antigen thereby maintaining it available to immune cells for a longer period. Further, alum cannot be added to all types of antigens (e.g. live attenuated pathogens, some multivalent vaccines), and it induces primarily Th2 type immune responses, namely humoral inmmunity but rarely CTL. For many pathogens, a humoral response alone is insufficient for protection, and for some pathogens can even be detrimental.

In addition, an immunostimulatory oligonucleotide in the nucleic acid construct of the invention can be administered prior to, along with or after administration of a chemotherapy or other immunotherapy to increase the responsiveness of malignant cells to subsequent chemotherapy or immunotherapy or to speed the recovery of the bone marrow through induction of restorative cytokines such as GM-CSF. CpG nucleic acids also increase natural killer cell lytic activity and antibody dependent cellular cytotoxicity (ADCC). Induction of NK activity and ADCC may likewise be beneficial in cancer immunotherapy, alone or in conjunction with other treatments.

Gene Therapy

Plasmid or vector DNA may also be useful for certain gene therapy applications. In most such cases, an immune response against the encoded gene product would not be desirable. Thus, the optimal plasmid DNA cassette for gene therapy purposes will have all possible immunostimulatory (CpG-S) motifs removed and several immunoinhibitory (CpG-N) motifs added in. An exemplary vector for gene therapy purposes is described in the Examples.

Despite comparable levels of unmethylated CpG dinucleotides, DNA from serotype 12 adenovirus is immune stimulatory, but serotype 2 is nonstimulatory and can even inhibit activation by bacterial DNA. In type 12 genomes, the distribution of CpG-flanking bases is similar to that predicted by chance. However, in type 2 adenoviral DNA the immune stimulatory CpG-S motifs are outnumbered by a 15 to 30 fold excess of CpG dinucleotides in clusters of direct repeats or with a C on the 5' side or a G on the 3' side. Synthetic oligodeoxynucleotides containing these putative neutralizing (CpG-N) motifs block immune activation by CpG-S motifs in vitro and in vivo. Eliminating 52 of the 134 CpG-N motifs present in a DNA vaccine markedly enhanced its Th1-like function in vivo, which was further increased by addition of CpG-S motifs. Thus, depending on the CpG motif, prokaryotic DNA can be either immune-stimulatory or neutralizing. These results have important implications for understanding microbial pathogenesis and molecular evolution, and for the clinical development of DNA vaccines and gene therapy vectors.

Gene therapy, like DNA-based immunization, involves introduction of new genes into cells of the body, where they will be expressed to make a desired protein. However, in contrast to DNA vaccines, an immune response against the expressed gene product is not desired for gene therapy purposes. Rather, prolonged expression of the gene product is desired to augment or replace the function of a defective gene, and thus immune responses against the gene product are definitely undesirable.

Plasmid DNA expression vectors are also used for gene therapy approaches. They may be preferable to viral vectors (ie., recombinant adenovirus or retrovirus), which themselves are immunogenic (Newman, K. D., et al., *J Clin. Invest.*, 96:2955–2965, 1995; Zabner, J., et al., *J Clin. Invest.*, 97:1504–1511, 1996). Immune responses directed against such vectors may interfere with successful gene transfer if the same vector is used more than once. Double-stranded DNA is poorly immunogenic (Pisetsky, D. S. *Antisense Res. Devel.* 5: 219–225, 1995; Pisetsky, D. S. *J Immunol*. 156: 421–423, 1996), and thus from this perspective, repeated use is not a problem with plasmid DNA.

Nevertheless, even when gene transfer is carried out with plasrnid DNA vectors, expression of the introduced gene is often short-lived and this appears to be due to immune responses against the expressed protein (Miller, A. D. *Nature*. 357: 455–460, 1992; Lasic, D. D., and Templeton, N. S. *Advanced Drug Delivery Review*. 20: 221–266, 1996). It is not a surprise that expression of a foreign protein, as is the case with gene replacement strategies, induces immune responses. Nevertheless, it is likely that the presence of CpG-S motifs aggravates this situation. The finding that removal of CpG-S motifs from DNA vaccines can abolish their efficacy suggests that such a strategy may prove useful for creating gene therapy vectors where immune responses against the encoded protein are undesirable. Furthermore, the more recent discovery of CpG-N motifs opens up the possibility of actually abrogating unwanted immune responses through incorporating such motifs into gene delivery vectors. In particular, the Th-2 bias of CpG-N motifs may prevent induction of cytotoxic T-cells, which are likely the primary mechanism for destruction of transfected cells.

In another embodiment, the invention provides a method for enhancing the expression of a therapeutic polypeptide in vivo wherein the polypeptide is contained in a nucleic acid construct. The construct is produced by removing stimulatory CpG (CpG-S) motifs and optionally inserting neutralizing CpG (CpG-N) motifs, thereby producing a nucleic acid construct providing enhanced expression of the therapeutic polypeptide. Alternatively, the invention envisions using the construct for delivery of antisense polynucleotides or ribozymes.

Typical CpG-S motifs that are removed from the construct include a motif having the formula:

$5'\ X_1CGX_23'$ wherein at least one nucleotide separates consecutive CpGs, $X_1$ is adenine, guanine, or thymine and $X_2$ is cytosine, thymine, or adenine. Exemplary CpG-S oligonucleotide motifs include GACGTT, AGCGTT, AACGCT, GTCGTT and AACGAT. Another oligonucleotide useful in the construct contains TCAACGTT. Further exemplary oligonucleotides of the invention contain GTCG(T/C)T, TGACGTT, TGTCG(T/C)T, TCCATGTCGTTCCTGTCGTT (SEQ ID NO:1), TCCTGACGTTCCTGACGTT (SEQ ID NO:2) and TCGTCGTTTTGTCGTTTTGTCGTT (SEQ ID NO:3). These motifs can be removed by site-directed mutagenesis, for example.

Preferably CpG-N motifs contain direct repeats of CpG dinucleotides, CCG trinucleotides, CGG trinucleotides, CCGG tetranucleotides, CGCG tetranucleotides or a combination of any of these motifs. In addition, the neutralizing motifs of the invention may include oligos that contain a sequence motif that is a poly-G motif, which may contain at least about four Gs in a row or two G trimers, for example (Yaswen et al., *Antisense Research and Development* 3:67, 1993; Burgess et al., *PNAS* 92:4051, 1995).

The present invention provides gene therapy vectors and methods of use. Such therapy would achieve its therapeutic effect by introduction of a specific sense or antisense polynucleotide into cells or tissues affected by a genetic or other disease. It is also possible to introduce genetic sequences into a different cell or tissue than that affected by the disease, with the aim that the gene product will have direct or indirect impact on the diseases cells or tissues. Delivery of polynucleotides can be achieved using a plasmid vector as described herein (in "naked" or formulated form) or a recombinant expression vector (e.g., a chimeric vector).

For long-term, high-yield production of recombinant proteins, stable expression is preferred. Rather than using expression vectors which contain viral origins of replication, host cells can be transformed with a heterologous cDNA controlled by appropriate expression control elements (e.g., promoter, enhancer, sequences, transcription terminators, polyadenylation sites, etc.), and a selectable marker. The selectable marker in a recombinant plasmid or vector confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., 1977, Cell 11: 223), hypoxanthine-guanine phospho-ribosyltransferase (Szybalska & Szybalski, 1962, *Proc. Natl. Acad. Sci. USA*. 48: 2026), and adenine phosphoribosyltransferase (Lowy, et al., 1980, Cell 22: 817) genes can be employed in tk-, hgprt⁻ or aprt⁻ cells respectively. Also, antimetabolite resistance can be used as the basis of selection for dhfr, which confers resistance to methotrexate (Wigler, et al., 1980, *Natl. Acad. Sci. USA* 77: 3567; O'Hare, et al., 1981, *Proc. Natl. Acad. Sci. USA* 78: 1527); gpt, which confers resistance to mycophenolic acid (Mulligan & Berg, 1981, *Proc. Natl. Acad. Sci. USA* 78: 2072; neo, which confers resistance to the aminoglycoside G-418 (Colberre-Garapin, et al., 1981, *J. Mol. Biol.* 150: 1); and hygro, which confers resistance to hygromycin (Santerre, et al., 1984, Gene 30: 147) genes. Recently, additional selectable genes have been described, namely trpB, which allows cells to utilize indole in place of tryptophan; hisD, which allows cells to utilize histinol in place of histidine (Hartman & Mulligan, 1988, *Proc. Natl Acad. Sci. USA* 85: 8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) can be utilized. A number of additional retroviral vectors can incorporate multiple genes. All of these vectors can transfer or incorporate a gene for a selectable marker so that transduced cells can be identified and generated.

Therapeutic peptides or polypeptides are typically included in the vector for gene therapy. For example, immunomodulatory agents and other biological response modifiers can be administered for incorporation by a cell. The term "biological response modifiers" is meant to encompass substances which are involved in modifying the immune response. Examples of immune response modifiers include such compounds as lymphokines. Lymphokines include tumor necrosis factor, interleukins (e.g., IL-2, -4, -6, -10 and -12), lymphotoxin, macrophage activating factor, migration inhibition factor, colony stimulating factor, and alpha-interferon, beta-interferon, and gamma-interferon and their subtypes. Also included are polynucleotides which encode metabolic enzymes and proteins, including Factor VIII or Factor IX. Other therapeutic polypeptides include the cystic fibrosis transmembrane conductance regulator (e.g., to treat cystic fibrosis); structural or soluble muscle proteins such as dystrophin (e.g., to treat muscular dystrophies); or hormones. In addition, suicide or tumor repressor genes can be utilized in a gene therapy vector described herein.

In addition, antisense polynucleotides can be incorporated into the nucleic acid construct of the invention. Antisense polynucleotides in context of the present invention includes both short sequences of DNA known as oligonucleotides of usually 10–50 bases in length as well as longer sequences of DNA that may exceed the length of the target gene sequence itself. Antisense polynucleotides useful for the present invention are complementary to specific regions of a corresponding target mRNA. Hybridization of antisense polynucleotides to their target transcripts can be highly specific as a result of complementary base pairing.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl Genet*. 1: 273 (1982)); the TK promoter of Herpes virus (McKnight, *Cell* 31: 355 (1982); the SV40 early promoter (Benoist et al., *Nature* 290: 304 (1981); the Rous sarcoma virus promoter (Gorman et al., *Proc. Nat'l Acad. Sci. USA* 79: 6777 (1982); and the cytomegalovirus promoter (Foecking et al., Gene 45: 101 (1980)) (See also discussion above for suitable promoters).

Alternatively, a prokaryotic promoter, such as the bacteriophage T3 RNA polymerase promoter, can be used to control fusion gene expression if the prokaryotic promoter is regulated by a eukaryotic promoter. Zhou et al., *Mol. Cell. Biol*. 10: 4529 (1990); Kaufinan et al., *Nucl. Acids Res*. 19: 4485 (1991).

It is desirable to avoid promoters that work well in APC since that could induce an immune response. Thus, ubiquitous viral promoters, such as CMV, should be avoided. Promoters specific for the cell type requiring the gene therapy are desirable in many instances. For example, with cystic fibrosis, it would be best to have a promoter specific for the lung epithelium. In a situation where a particular cell type is used as a platform to produce therapeutic proteins destined for another site (for either direct or indirect action), then the chosen promoter should work well in the "factory" site. Muscle is a good example for this, as it is post-mitotic, it could produce therapeutic proteins for years on end as long as there is no immune response against the protein-expressing muscle fibers . Therefore, use of strong muscle promoters as described in the previous section are particularly applicable here. Except for treating a muscle disease per se, use of muscle is typically only suitable where there is a secreted protein so that it can circulate and function elsewhere (e.g., hormones, growth factors, clotting factors).

Administration of gene therapy vectors to a subject, either as a plasmid or as part of a viral vector can be affected by many different routes. Plasmid DNA can be "naked" or formulated with cationic and neutral lipids (liposomes), microencapsulated, or encochleated for either direct or indirect delivery. The DNA sequences can also be contained within a viral (e.g., adenoviral, retroviral, herpesvius, pox virus) vector, which can be used for either direct or indirect delivery. Delivery routes include but are not limited to intramuscular, intradermal (Sato, Y. et al., *Science* 273: 352–354, 1996), intravenous, intra-arterial, intrathecal, intrahepatic, inhalation, intravaginal instillation (Bagarazzi et al., *J Med. Primatol.* 26:27, 1997), intrarectal, intratumor or intraperitoneal.

As much as 4.4 mg/kg/d of antisense polynucleotide has been administered intravenously to a patient over a course of time without signs of toxicity. Martin, 1998, "Early clinical trials with GDM91, a systemic oligodeoxynucleotide", In: Applied Oligonucleotide Technology, C. A. Stein and A. M. Krieg, (Eds.), John Wiley and Sons, Inc., New York, N.Y.). Also see Sterling, "Systemic Antisense Treatment Reported," *Genetic Engineering News* 12: 1, 28 (1992).

Delivery of polynucleotides can be achieved using a plasmid vector as described herein, that can be administered as "naked DNA" (i.e., in an aqueous solution), formulated with a delivery system (e.g., liposome, cochelates, microencapsulated). Delivery of polynucleotides can also be achieved using recombinant expression vectors such as a chimeric virus. Thus the invention includes a nucleic acid construct as described herein as a pharnaceutical composition useful for allowing transfection of some cells with the DNA vector such that a therapeutic polypeptide will be expressed and have a therapeutic effect (to ameliorate symptoms attributable to infection or disease). The pharmaceutical compositions according to the invention are prepared by bringing the construct according to the present invention into a form suitable for administration to a subject using solvents, carriers, delivery systems, excipients, and additives or auxiliaries. Frequently used solvents include sterile water and saline (buffered or not). One carrier includes gold particles, which are delivered biolistically (ie., under gas pressure). Other frequently used carriers or delivery systems include cationic liposomes, cochleates and microcapsules, which may be given as a liquid solution, enclosed within a delivery capsule or incorporated into food.

An alternative formulation for the administration of gene therapy vectors involves liposomes. Liposome encapsulation provides an alternative formulation for the administration of polynucleotides and expression vectors. Liposomes are microscopic vesicles that consist of one or more lipid bilayers surrounding aqueous compartments. See, generally, Bakker-Woudenberg et al, *Eur. J. Clin. Microbiol. Infect. Dis.* 12 (Suppl. 1): S61 (1993), and Kim, Drugs 46: 618 (1993). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 $\mu$m to greater than 10 $\mu$m. See, for example, Machy et al., LIPOSOMES IN CELL BIOLOGY AND PHARMACOLOGY (John Libbey 1987), and Ostro et al., American J. Hosp. Phann. 46: 1576 (1989).

After intravenous administration, conventional liposomes are preferentially phagocytosed into the reticuloendothelial system. However, the reticuloendothelial system can be circumvented by several methods including saturation with large doses of liposome particles, or selective macrophage inactivation by pharmacological means. Claassen et al., *Biochim. Biophys. Acta* 802: 428 (1984). In addition, incorporation of glycolipid- or polyethelene glycol-derivatised phospholipids into liposome membranes has been shown to result in a significantly reduced uptake by the reticuloendothelial system. Allen et al., *Biochim. Biophys. Acta* 1068: 133 (1991); Allen et al., *Biochim. Biohys. Acta* 1150: 9 (1993). These Stealth® liposomes have an increased circulation time and an improved targeting to tumors in animals. (Woodle et al., *Proc. Amer. Assoc. Cancer Res.* 33: 2672 1992). Human clinical trials are in progress, including Phase III clinical trials against Kaposi's sarcoma. (Gregoriadis et al., *Drugs* 45: 15, 1993).

Expression vectors can be encapsulated within liposomes using standard techniques. A variety of different liposome compositions and methods for synthesis are known to those of skill in the art. See, for example, U.S. Pat. No. 4,844,904, U.S. Pat. No. 5,000,959, U.S. Pat. No. 4,863,740, U.S. Pat. No. 5,589,466, U.S. Pat. No. 5,580,859, and U.S. Pat. No. 4,975,282, all of which are hereby incorporated by reference.

Liposomes can be prepared for targeting to particular cells or organs by varying phospholipid composition or by inserting receptors or ligands into the liposomes. For instance, antibodies specific to tumor associated antigens may be incorporated into liposomes, together with gene therapy vectors, to target the liposome more effectively to the tumor cells. See, for example, Zelphati et al., *Antisense Research and Development* 3: 323–338 (1993), describing the use "immunoliposomes" containing vectors for human therapy.

In general, the dosage of administered liposome-encapsulated vectors will vary depending upon such factors as the patient's age, weight, height, sex, general medical condition and previous medical history. Dose ranges for particular formulations can be determined by using a suitable animal model.

In addition to antisense, ribozymes can be utilized with the gene therapy vectors described herein. Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, Nature, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target MRNA species. Consequently, hammerhead-type ribozymes are preferable to tetrahymena-type ribozymes for inactivating a specific MRNA species and 18-based recognition sequences are preferable to shorter recognition sequences.

All references cited herein are hereby incorporated by reference in their entirety. The following examples are intended to illustrate but not limit the invention. While they are typical of those that might be used, other procedures known to those skilled in the art may alternatively be used.

EXAMPLE 1

Cloning of CpG Optimized Plasmid DNA Vectors

Plasmids and other reagents

The cloning vector pUK21, which contains one ColE1 replication region, kanamycin resistance gene and polylinker, was provided by Martin Schleef of Qiagen Inc. (Qiagen, Hilden, Germany). The expression vector pcDNA3 was purchased from Invitrogen Corp. (Carlsbad, USA). *E. coli* strain DH5α was used as the bacterial host.

Pwo DNA polymerase, T4 DNA ligase, dNTP and ATP were purchased from Boerhinger Mannheim (Mannheim, Germany). T4 DNA polymerase, large fragment of DNA polymerase I (klenow), T4 DNA polynucleotide kinase, CIP (calf intestinal alkaline phosphatase) and restriction enzymes were purchased from New England BioLabs (Beverly, USA) and GIBCO BRL (Gaithersburg, USA). General laboratory chemicals were from Sigma Chemical Corp. (St. Louis, USA).

Recombinant DNA techniques

Unless specified otherwise, all recombinant DNA methods were as described by Sambrook et al. (1989). Plasmid DNA was prepared with Qiagen Plasmid Kits (Qiagen Inc). DNA purification was carried out by separating DNA fragments on an agarose gel and extracting with QIAquick Gel Extraction Kit (Qiagen Inc). Double-stranded DNA sequencing was performed with ABI PRISM automatic sequencing system (Perkin Elmer Corp., Norwalk, USA). Oligonucleotides for primers were synthesized with a DNA synthesizer, model Oligo 1000, manufactured by Beckman Instrument Inc.(Palo Alto, USA). PCR was performed with the Perkin Elmer PCR system 2400.

PCR conditions

Cycling conditions for each PCR began with a 2-min denaturation at 94° C., followed by 25 cycles of denaturation at 94° C. for 15 sec, annealing at 55° C. for 30 sec, elongation at 72° C. for 45 sec (adjusted according to the size of DNA fragment), and completed with a 7-min incubation at 72° C. High-fidelity Pwo polymerase was used when fragments were created for cloning and site-directed mutagenesis.

Construction of basic expression vector

The pUK21 vector was used as the starting material to construct a basic expression vector, which was subsequently used for construction of either a CpG-optimized DNA vaccine vectors or a CpG-optimized gene therapy vectors. DNA sequences required for gene expression in eukaryotic cells were obtained by PCR using the expression vector pcDNA3 as a template.

Figure 1B:
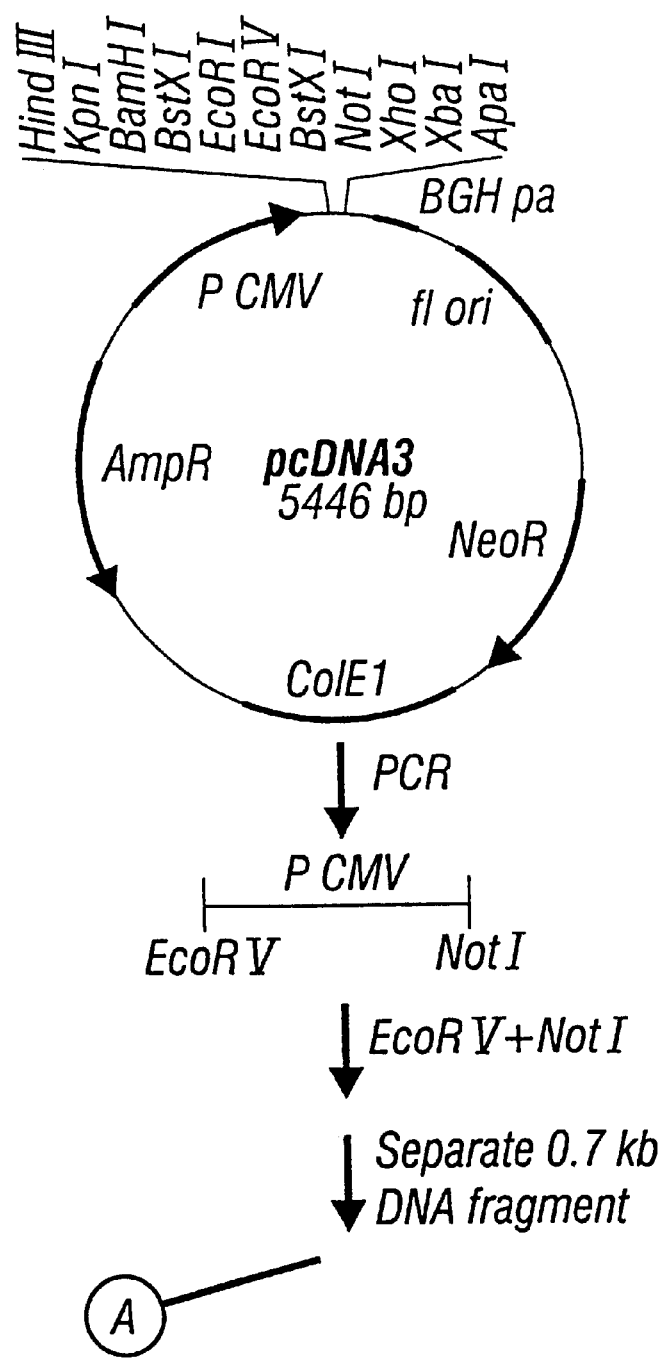

(i) Insertion of the CMV (human cytomegalovirus) major intermediate early promoter/enhancer region The CMV promoter (from pcDNA3 position 209 to 863) was amplified by PCR using 30 ng pcDNA3 as a template. The forward PCR primer 5' CGT CGA TAT CCG ATG TAC GGG CCA GAT AT 3' (SEQ ID NO:4) introduced an EcoRV site, and the reverse PCR primer 5' AGT CGCGGCCGC AAT TTC GAT AAG CCA GTA AG 3 ' (SEQ ID NO:5) introduced a NotI site. After digestion with EcoRV and NotI, a 0.7 kb PCR fragment containing the CMV promoter was purified and inserted into the pUK21 polylinker between XbaI and NotI sites. The XbaI sticky end of pUK21 was filled in with the large fragment of T4 DNA polymerase after digestion to create a blunt end. The inserted CMV promoter was confirmed by sequencing. The resulting plasmid was pUK21-A1 (FIGS. 1A and 1B).

(ii) Insertion of the BGH polyA (bovine growth hormone polyadenylation signal)

Figure 2A:
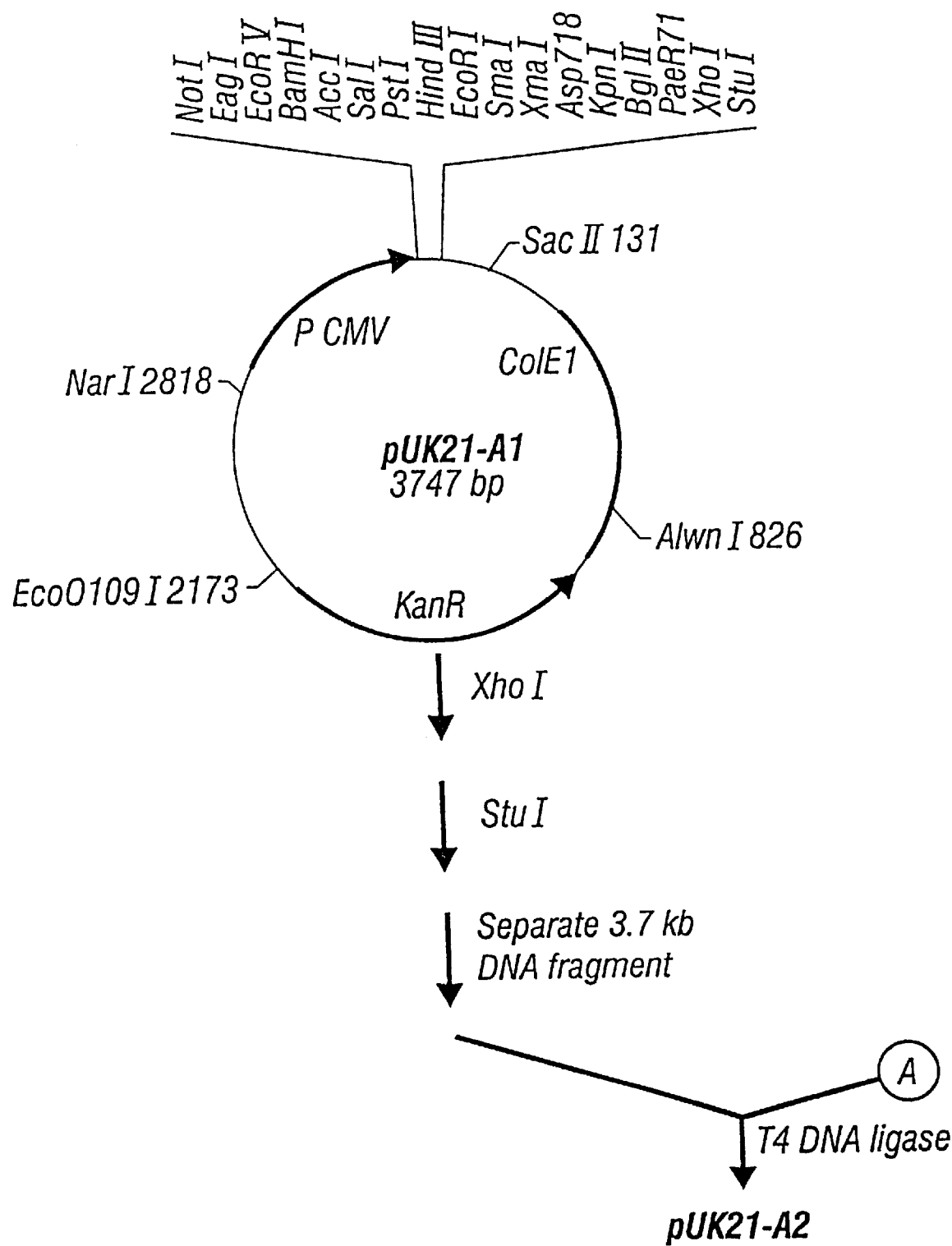
FIG. 2A and 2B are a schematic diagrams of the construction of pUK21-A2.
Figure 2B:
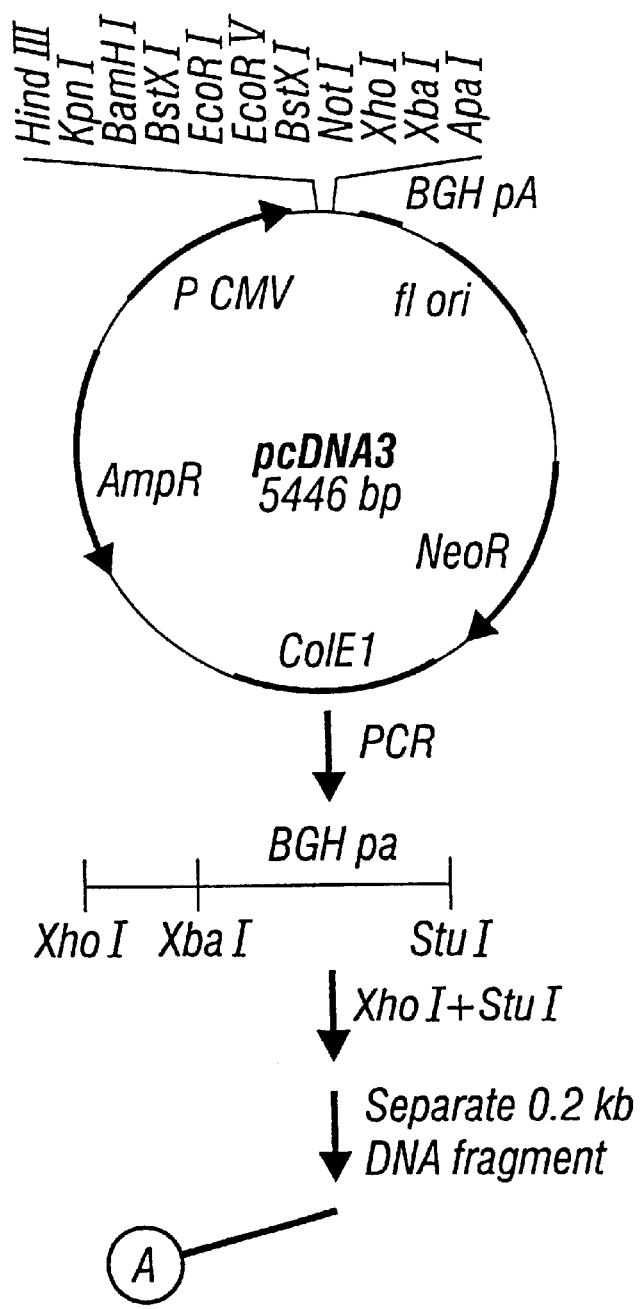

BGH polyA (from pcDNA3 position 1018 to 1249) was amplified by PCR using pcDNA3 as template. The forward PCR primer 5' ATT CTC GAG TCT AGA CTA GAG CTC GCT GAT CAG CC 3' (SEQ ID NO:6) introduced XhoI and XbaI sites, and the reverse PCR primer 5' ATT AGG CCT TCC CCA GCA TGC CTG CTA TT 3' (SEQ ID NO:7) introduced a StuI site. After digestion with xhoI and StuI, the 0.2 kb PCR fragment containing the BGH polyA was purified, and ligated with the 3.7 kbXhoI-StuI fragment of pUK21-A1. The inserted BGH polyA was confirmed by sequencing. The resulting plasmid was pUK21-A2 (FIG. 2A and 2B).

Note: Ligation of the EcoRV and xbaI-fill-in blunt ends in the pUK21-A1 construct recreated an XbaI site, but this site is resistant to cleavage due to Dam methylation present in most laboratory strains of *E. coli*, such as DH5α, so the extra XbaI site introduced by the forward PCR primer in the pUK21-A2 construct is available as a cloning site.

CpG optimized DNA vaccine vector

The CpG-optimized DNA vaccine vectors were made from the basic expression vector (pUK21-A2) in several steps:

Site-directed mutagenesis for removal of CpG-N motifs, with care being taken to maintain the integrity of the open reading frame. Where necessary, the mutated sequence was chosen to encode the same amino acids as the original sequence.

Removal of unnecessary sequences (e.g., f1 ori).

Addition of suitable polylinker sequence to allow easy incorporation of CpG-S motifs.

Addition of CpG-S motifs which would be chosen to enhance a particular immune response (humoral, cell-mediated, high levels of a particular cytokine etc.).

The pUK2 1-A2 vector was used as the starting material for construction of an optimized DNA vaccine vector. Site-directed mutagenesis was carried out to mutate those CpG-N sequences that were easy to mutate. As described below, 22 point-mutations were made to change a total of 15 CpG-N motifs to alternative non-CpG sequences. For 16 of these point mutations that were in coding regions, the new sequences encoded the same amino acids as before through alternative codon usage. The mutated sequences were all in the kanamycin resistance gene or immediately adjacent regions. At present, we did not mutate any CpG-N motifs in regions with indispensable functions such as the ColEl, BGH poly A or polylinker regions, or the promoter region (in this case CMV), however this should be possible.

(i) Insertion of the f1 origin of replication region

Figure 3A:
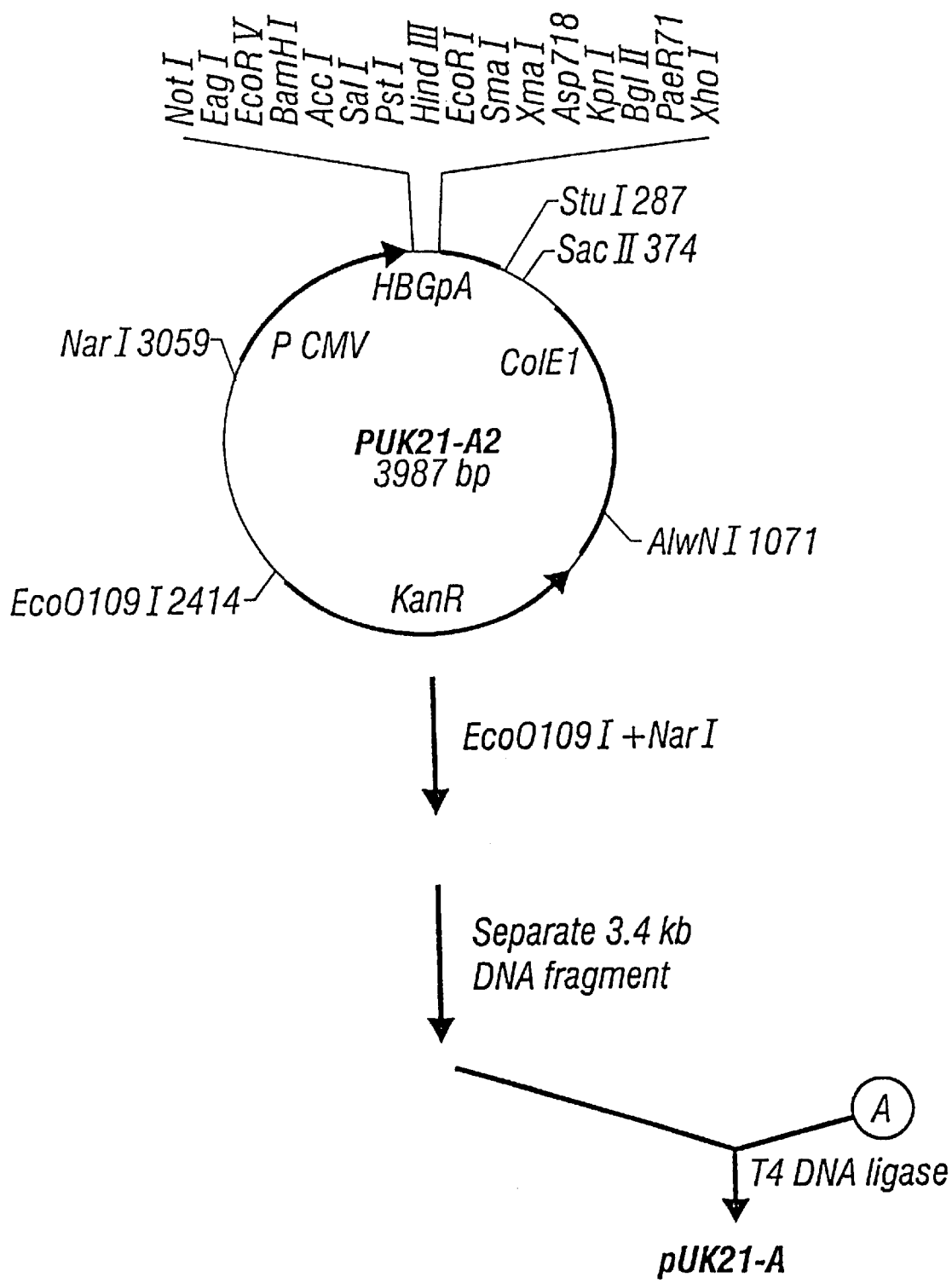
FIG. 3A and 3B are a schematic diagrams of the construction of pUK21-A.
Figure 3B:
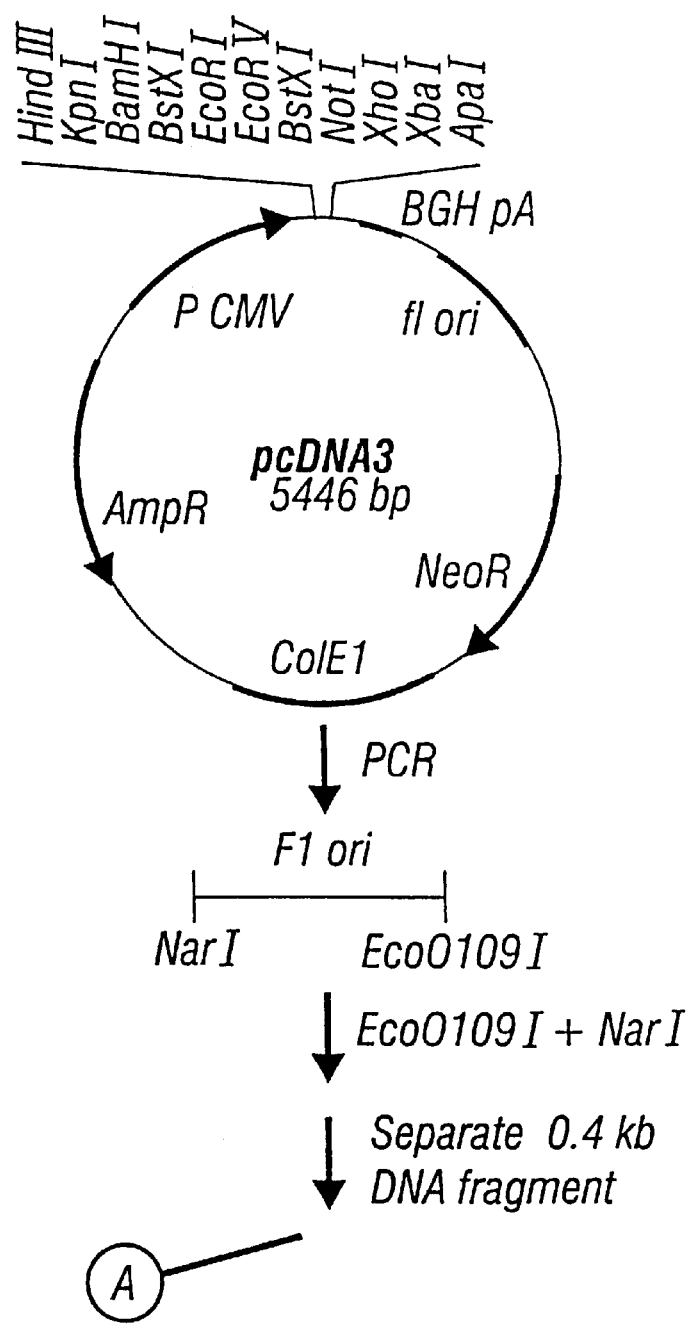

The f1 origin and two unique restriction enzyme sites (DraI and ApaI) were introduced into pUK21-A2 for later vector construction. f1 origin (from pcDNA3 position 1313 to 1729) was amplified by PCR using pcDNA3 as template. The forward PCR primer 5' TAT AGG CCC TAT TTT AAA CGC GCC CTG TAG CGG CGC A 3' (SEQ ID NO:8) introduced EcoO109I and DraI sites, and the reverse PCR primer 5' CTA TGG CGC CTT GGG CCC AAT TTT TGT TAA ATC AGC TC 3' (SEQ ID NO:9) introduced NarI and ApaI site. After digestion with NarI and EcoO109I, the 0.4 kb PCR fragment containing the f1 origin was purified and ligated with the 3.3 kb NarI-EcoO109I fragment of pUK21 -A2, resulting in pUK21-A (FIG. 3A and 3B).

(ii) Site-directed Mutagenesis to Remove Immunoinhibitory Sequences

Sixteen silent-mutations within the kanamycin resistance gene and another six point-mutations within a non-essential DNA region were designed in order to eliminate immunoinhibitory CpG-N sequences. At this time, mutations were not made to CpG-N motifs contained in regions of pUK21-A that had essential functions.

Site-directed mutagenesis was performed by overlap extension PCR as described by Ge et al. (1997). The 1.3 kb AlwNI-EcoO109I fragment of pUK21-A contained all 22 nucleotides to be mutated and was regenerated by overlap extension PCR using mutagenic primers. All the primers used for mutagenesis are listed in Table 1, and the nucleotide sequence of this AlwNI-EcoO109I fragment is listed in Table 2 (Note: the nucleotide numbering scheme is the same as the backbone vector pUK21).

The mutagenesis was carried out as follows: In the first round of overlap extension PCR, the pairs of primers: Mu-0F/Mu-(4+5)R Mu-(4+5)F/Mu-9R, Mu-9F/Mu-13R and Mu-13F/Mu-0R were used to introduce four point-mutations at positions 1351, 1363, 1717 and 1882. The PCR-generated EcoRI/AIwNI-EcoO109I/XbaI fragment was inserted into the pcDNA3 polylinker between the EcoR I and XbaI sites. The mutated MspI at position 1717 was used to identify the pcDNA3-insert containing the appropriate mutant DNA fragment.

In the second round of overlap extension PCR, the pcDNA3-insert from the first-round was used as a PCR template, the pairs of primers: Mu-0F/Mu-2R, Mu-2F/Mu-7R, Mu-7F/Mu-10R and Mu-10F/Mu-0R were used to introduce three point-mutations at positions 1285, 1549 and 1759. The PCR-generated EcoRI/AlwN-EcoO109I/XbaI fragment was inserted into the pcDNA3 polylinker between the EcoRI and XbaI sites. The SnaBI site created by mutation at position 1759 was used to identify the pcDNA3-insert containing the appropriate mutant DNA fragment.

In the third round of overlap extension PCR, the pcDNA3-insert from the second-round was used as a template, the pairs of primers: Mu-0F/Mu-3R, Mu-3F/Mu-8R, Mu-8F/Mu-14R and Mu-14F/Mu-0R were used to introduce five point-mutations at positions 1315, 1633, 1636, 1638 and 1924. The PCR-generated EcoRI/AlwNI-EcoO109I/XbaI fragment was inserted into the pcDNA3 polylinker between the EcoRI and XbaI sites. The mutated MspI site at position 1636 was used to identify the pcDNA3-insert containing the appropriate DNA mutant fragment.

In the last round of overlap extension PCR, the pcDNA3-insert from the third-round was used as a template, the pairs of primers: Mu-0F/Mu-1R, Mu-IF/Mu-6R, Mu-6F/Mu-(11+12)R, Mu-(11+12)F/Mu-15R and Mu-15F/Mu-0R were used to introduce 10-point mutations at positions 1144, 1145, 1148, 1149, 1152, 1153, 1453, 1777, 1795 and 1984. After digestion with the EcoO109I and AlwNI, the PCR-generated 1.3 kb fragment was inserted into pUK21-A to replace the corresponding part, resulting in pUK21-B. All the 22 point-mutations were confirmed by sequencing, and the PCR-generated AlwNI-EcoO109I fragment was free from PCR errors.

(iii) Replacement of the f1 origin with unique restriction enzyme sites

Figure 4A:
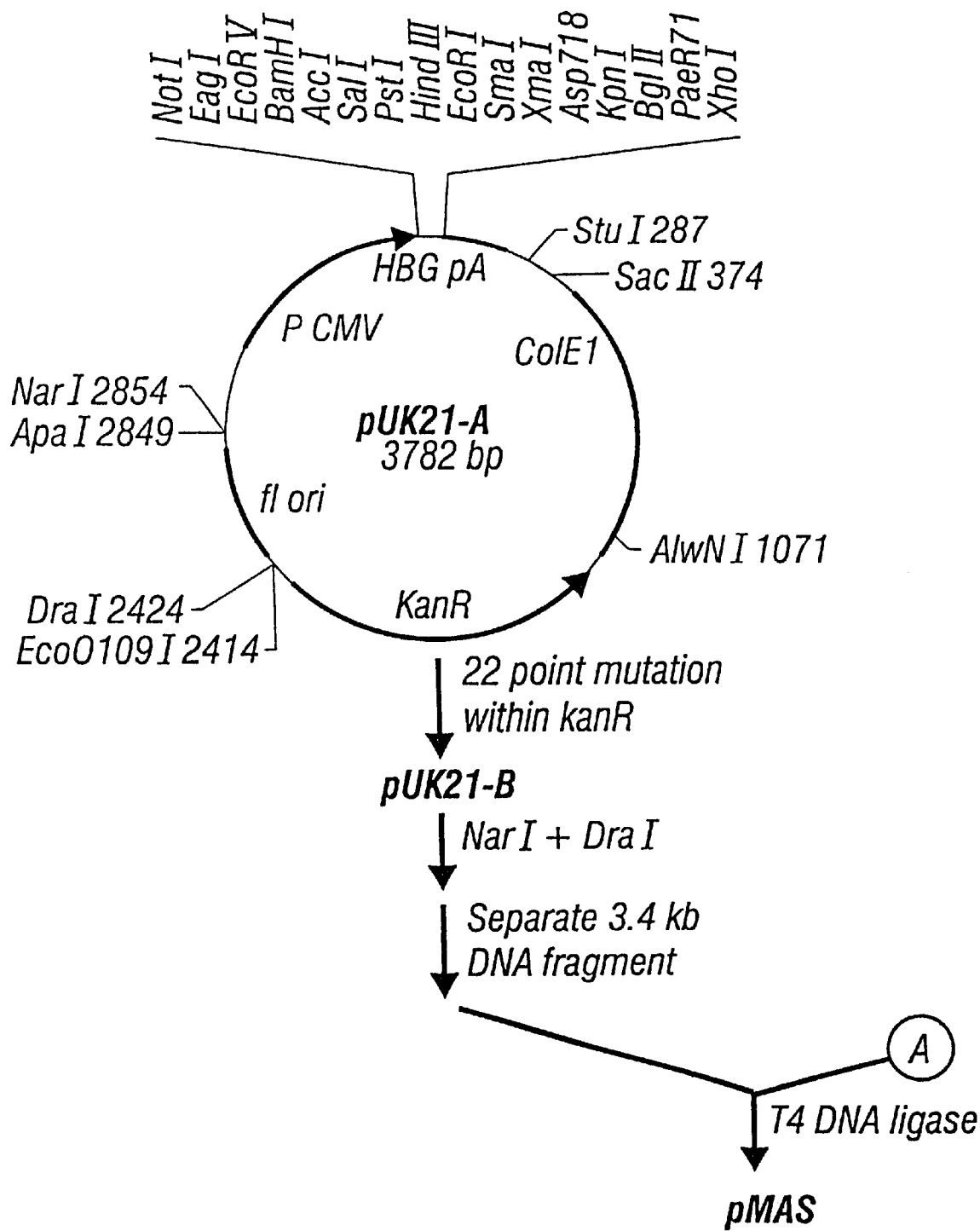
Figure 5:
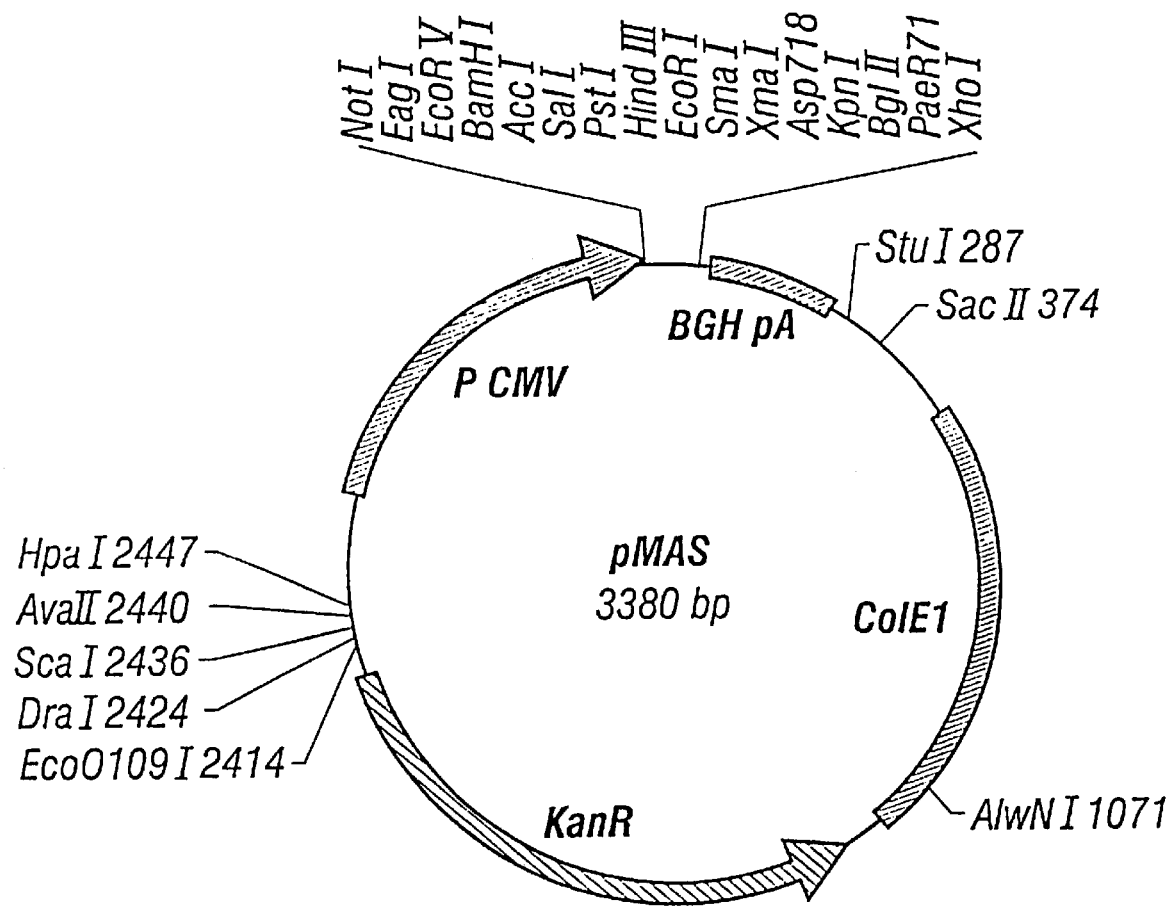
FIG. 5 is a diagram of DNA vector pMAS. The following features are contained within pMAS. CMV promoter which drives expression of inserted genes in eukaryotic cells. BGH polyA for polyadenylation of transcribed mRNAs. ColE1 origin of replication for high copy number growth in E. coli. Kanamycin resistance gene for selection in E. coli. Polylinker for gene cloning. Unique restriction enzyme sites DraI-BstRI-ScaI-AvaII-HpaII for inserting immune stimulatory sequences.

Oligonucleotides 5' AAA TTC GAA AGT ACT GGA GTT AAC A 3' (SEQ ID NO:10) and its complementary strand 5' CGT GTT AAC AGG TCC AGT ACT TTC GAA TTT 3' (SEQ ID NO:1 11) were synthesized, and 5'-phosphorylated. Annealing of these two phosphorylated oligos resulted in 28 base pair double-stranded DNA containing three unique restriction enzyme sites (ScaI, AvaII, HpaI), one sticky end and one blunt end. Replacing the 0.4 kb NarI-DraI fragment of pUK21-B with this double-stranded DNA fragment resulted in the universal vector pMAS for DNA vaccine development (FIGS. 4A and 4B and 5).

(iv) Insertion of immunostimulatory motifs into the vector pMAS

The vector is now ready for cloning CpG-S motifs. The exact motif which would be added to the vector would depend on its ultimate application, including the species it is to be used in and whether a strong humoral and/or a cell-mediated response was preferred. The following description gives an example of how a varying number of a given motif could be added to the vector.

Insertion of murine-specific CpO-S motifs was carnied out by first synthesizing the oligonucleotide 5' GAC TCC ATG ACG TTC CTG ACG TTT CCA TGA CGT TCC TGA CGT TG 3' (SEQ ID NO: 12) which contains four CpG-S motifs (underlined), and its complementary sequence 5' GTC CAA CGT CAG GAA CGT CAT GGA AAC GTC AGG AAC GTC ATG GA 3' (SEQ ID NO:13). This sequence is based on the CpG-S motifs contained in oligo #1826, which has potent stimulatory effects on murine cells in vitro and is a potent adjuvant for protein vaccines in vivo. After 5'-phosphorylation, annealing was performed to create a 44 bp double-stranded DNA fragment with AvaII-cut sticky ends. Self-ligation of this 44 bp DNA fragment resulted in a mixture of larger DNA fragments containing different copy numbers of the stimulatory motif These DNA fragments with different numbers of mouse CpG-S motifs were inserted into the AvaII site of pMAS, which was first dephosphorylated with CIP to prevent self-ligation. The resulting recombinant plasmids maintained one AvaII site due to the design of the synthetic oligonucleotide sequence allowing the cloning process to be repeated until the desired number of CpG-S motifs were inserted. Sixteen and 50 mouse CpG-S motifs were inserted into the AvaHi site of pMAS, creating pMCG-16 and pMCG-50 respectively. The DNA fragment containing 50 CpG-S motifs was excised from pMCG-50, and inserted into HpaI-AvaII-ScaI-DraI linker of pMCG-50, creating pMCG-100. The same procedure was followed to create pMCG-200 (Table 3). Two different sequences containing human-specific CpG-S motifs were cloned in different numbers into pMAS to create two series of vectors, pHCG and pHIS, following the same strategies as described above.

The pHCG series of vectors contain multiple copies of the following sequence 5' GAC TTC GTG TCG TTC TTC TGT CGT CTT TA TTC TCC TGC GTG CGT CCC TTG 3' (SEQ ID NO:14) (CpG-S motifs are underlined). This sequence incorporates various CpG-S motifs that had previously been found to have potent stimulatory effects on human cells in vitro. The vector pHCG-30, pHCG-50, pHCG-100 and pHCG-200 contain 30, 50, 100 and 200 human CpG-S motifs respectively (Table 3).

The pHIS series of vectors contain multiple copies of the following sequence: 5' GAC TCG TCG TTT TGT CGT TTT GTC GTT TCG TCG TTT TGT CGT TTT GTC GTT G 3' (SEQ ID NO: 15) (CPG-S motifs are underlined). This sequence is based on the CpG-S motifs in oligo #2006, which has potent stimulatory effects on human cells in vitro The vector pHIS-40, pHIS-64, pHIS-1 28 and pHIS-1 92 contain 40, 64, 128 and 192 human CpG motifs respectively (Table 3).

(v) Cloning of the hepatitis B surface antigen gene

To create a DNA vaccine, the S gene (subtype ayw) encoding the hepatitis B surface antigen (HBsAg) was amplified by PCR and cloned into the polylinker of pUK21-A2 using the EcoRV and Pst I restriction enzyme sites. The S gene was analyzed by sequencing, and then subdloned into the same restriction enzyme sites of the pMCG and pHCG series of vectors (Table 4).

The S gene (subtype adw2) encoding the hepatitis B surface antigen (HBsAg) was cloned into the pHIS series of vectors following the same strategy as described above (Table 4).

CpG optimized gene therapy vector

The optimized gene therapy vectors were constructed from the basic expression vector (pUK21-A2) in several steps.

(i) Site-directed mutagenesis for removal of CpG immunostimulatory sequences within pUK21-A2

Only point-mutations, which would not interfere with the replication and function of the expression vector, pUK21-A2, were designed. Seventy-five point-mutations, including 55 nucleotides within non-essential regions and 20 silent-mutations within the kanamycin resistance gene, were carried out following the same strategy as described previously in (ii) Site-directed mutagenesis to remove immunoinhibitoiy sequences. The point mutations eliminated 64 CpG stimulatory motifs resulting in the vector pGT (Table 5).

ii) Insertion of unique restriction enzyme sites into pGT

Oligonucleotides 5' GCC CTA GTA CTG TTA ACT TTA AAG GGC CC 3' (SEQ ID NO:16) and its complementary strand 5' GGC GGG CCC TTT AAA GTT AAC AGT ACT AG 3' (SEQ ID NO: 17) were synthesized, and 5'-phosphorylated. Annealing of these two phosphorylated oligos resulted in a 26 bp double-stranded DNA fragment containing four unique restriction enzyme sites (ScaI, HpaI, DraI and ApaI) and two EcoO109I-cut sticky ends. Insertion of this 26 bp DNA fragment into pGT created the vector pGTU.

iii) Insertion of immunoinhibitory motifs into the vector pGTU

Human CpG-N motifs were cloned into the pGTU following the same strategies as described previously in (iv) Insertion of immunostimulatory motifs into the vector pMAS. The oligonucleotide 5' GCC CTG GCG GGG ATA AGG CGG CGA TTT CGC GGG GGA TAA GGC GGG GAA 3' (SEQ ID NO:18) and its complementary strand 5' GGC CCC CGC CTT ATC CCC GCC AAA TCC CCG CCT TAT CCC CGC CAG 3' (SEQ ID NO:19) (four CpG motifs are underlined) were synthesized and phosphorylated. Annealing of these two oligonucleotides created a double-stranded DNA fragment, which was self-ligated first and then cloned into the EcoO109I site of the vector pGTU. The recombinant plasmids will be screened by restriction enzyme digestion and the vectors with the desired number of CpG inhibitory motifs will be sequenced and tested.

Immunization of Mice and Assay of Immune Responses

Female BALB/c mice aged 6–8 weeks (Charles River, Montreal) were immunized with DNA vaccines of HBsAg-encoding DNA (see vectors described above) by intramuscular injection into the tibialis anterior (TA) muscle. The plasmid DNA was produced in *E. coli* and purified using Qiagen endotoxin-free DNA purification mega columns (Qiagen GmbH, Chatsworth, Calif.). DNA was precipitated and redissolved in endotoxin-free PBS (Sigma, St. Louis MO) at a concentration of 0.01, 0.1 or 1 mg/ml. Total doses of 1, 10 or 100 μg were delivered by injection of 50 μl bilaterally into the TA muscles, as previously described (Davis et al., 1993b).

In some cases, 10 or 100 μg of CpG ODN was added to the DNA vaccine (pCMV-S, Davis et al., 1993b). The sequences and backbones of the ODN used are outlined in Table 6.

Mice were bled via the retro-orbital plexus at various times after immunization and recovered plasma was assayed for presence of anti-HBs antibodies (total IgG or IgG1 and IgG2a isotypes) by end-point dilution ELISA assay, as previously described (Davis et al., 1993a).

For assay of CTL activity, mice were killed and their spleens removed. Splenocytes were restimulated in vitro with HBsAg-expressing cells and CTL activity was evaluated by chromium release assay as previously described (Davis et al., 1998).

EXAMPLE 2

1. In vitro Effects of CpG-N Motifs

Nearly all DNA viruses and retroviruses have 50–94% fewer CpG dinucleotides than would be expected based on random base usage. This would appear to be an evolutionary adaptation to avoid the vertebrate defense mechanisms related to recognition of CpG-S motifs. CpG suppression is absent from bacteriophage, indicating that it is not an inevitable result of having a small genome. Statistical analysis indicates that the CpG suppression in lentiviruses is an evolutionary adaptation to replication in a eukaryotic host. Adenoviruses, however, are an exception to this rule as they have the expected level of genomic CpG dinucleotides. Different groups of adenovirae can have quite different clinical characteristics.

Unlike the genome of almost all DNA viruses and retroviruses, some adenoviral genomes do not show suppression of CpG dinucleotides (Karlin et al., 1994; Sun et al., 1997). Analysis of different adenoviral genomes (types 2, 5, 12, and 40) reveals surprising variability among each other and compared to human and *E. coli* in the flanking bases around CpG dinucleotides (Table 7).

Adenoviral strains 2 and 5 belong to the same family but strain 12 is quite distinct from them. Purified type 12 adenoviral DNA induced cytokine secretion from human PBMC to a degree similar to that seen with bacterial DNA (EC DNA) (Table 8). In contrast, DNA from types 2 and 5 adenoviruses induced little or no production of cytokines (Tables 3, 4). Remarkably, not only did type 2 and 5 adenoviral DNA fail to induce TNF-α or IFN-γ secretion, it actively inhibited the induction of this secretion by EC DNA (Table 9). In contrast, type 12 adenoviral DNA had no discernible inhibitory effects. These data suggested that type 2 and 5 adenoviral DNA contains sequence motifs that inhibit the cytokine responses to the stimulatory motifs present.

The bases flanking CpG motifs determine whether a CpG dinucleotide will cause immune stimulation, and may also determine the type of cytokines secreted. The fact that type 2 and 5 adenoviral DNA was not only nonstimulatory but actually inhibitory of CpG DNA, suggested that certain nonstimulatory CpG motifs may even be able to block the stimulatory motifs and that the inhibitory motifs should be over-represented in the genomes of adenovirus type 2 and 5 compared to type 12 (or to human DNA). By analysis of these genomes, it was possible to identify sequences that could block the effects of known CpG-S sequences on in vitro B cell proliferation (Table 10) and cytokine secretion (Table 11).

Sequences which were found to be immunoinhibitory by in vitro assay were chosen to be mutated (wherever easily possible) from the backbone of the DNA vaccine vector.

2. CpG-S ODN cannot be used as an Adjuvant for DNA Vaccines

It has previously been shown that CpG-S ODN is a potent vaccine adjuvant when given with HBsAg protein (Davis et al., 1998). Antibodies against HBsAg (anti-HBs) were augmented many times over those obtained with HBsAg alone or even HBsAg with alum as adjuvant. In addition, the humoral response was more strongly Th1, as indicated by a greater proportion of IgG2a than IgG1 isotypes of antibodies in immunized BALB/c mice. The strong TH1 effect of the CpG-S motifs was further demonstrated by the greatly enhanced cytotoxic T-cell activity. One of the most potent CpG-S ODN in mice was 1826, a 20-mer with 2 CpG-dinucleotides and made with a synthetic phosphorothioate backbone (see Table 6 for sequence).

Figure 6:
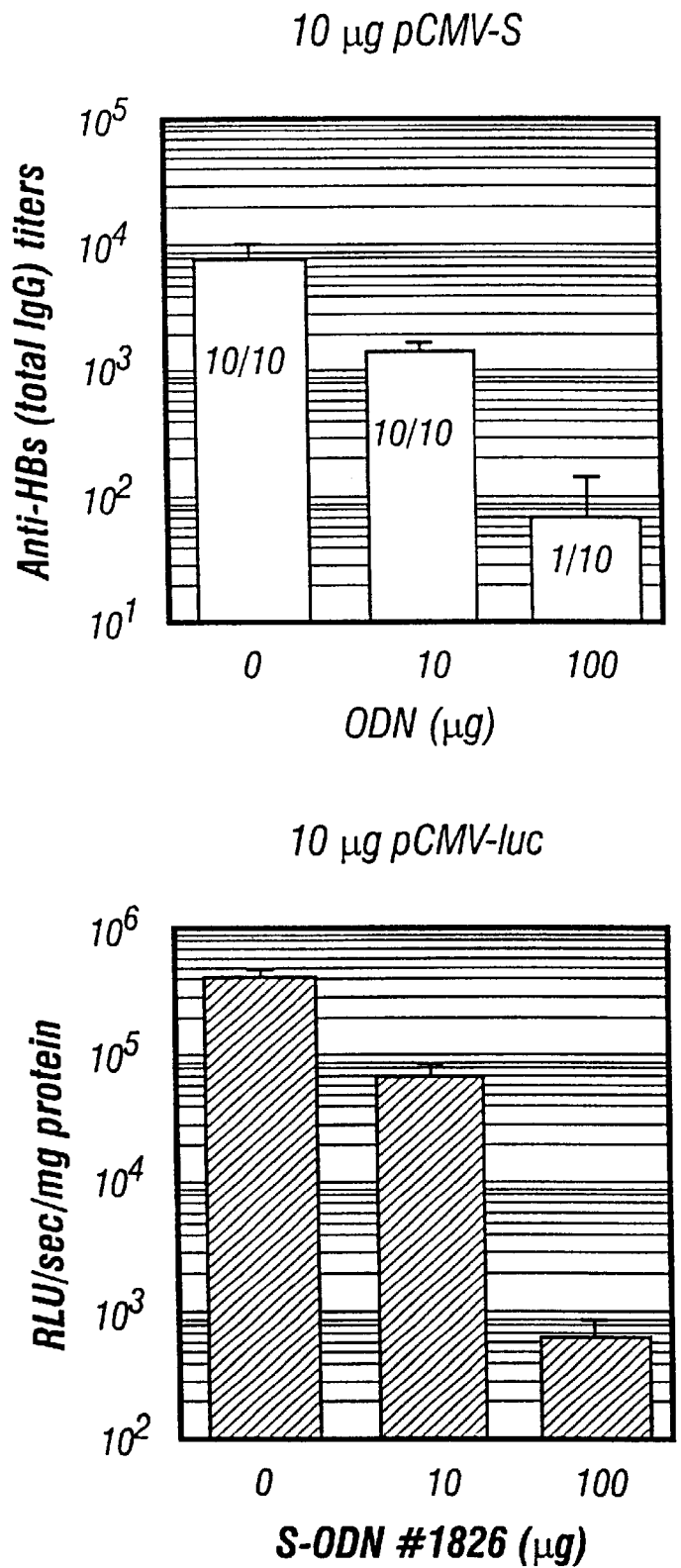
FIG. 6: Synthetic ODN cannot be mixed with DNA vaccine due to interference with expression from plasmid. The figure shows the effect of adding S-ODN to plasmid DNA expressing reporter gene or antigen. ODN 1826 (10 or 100 µg) was added to DNA constructs (10 µg) encoding hepatitis B surface antigen (HBsAg) (pCMV-S, top panel) or luciferase (pCMV-luc, bottom panel) DNA prior to intramuscular (IM) injection into mice. There was an ODN dose-dependent reduction in the induction of antibodies against HBsAg (anti-HBs, end-point dilution titers at 4 wk) by the pCMV-S DNA (top panel) and in the amount of luciferase expressed in relative light units per sec per mg protein (RLU/sec/mg protein at 3 days) from the pCMV-luc DNA (bottom panel). This suggests that the lower humoral response with DNA vaccine plus ODN was due to decreased antigen expression. Each bar represents the mean of values derived from 10 animals (top panel) or 10 muscles (bottom panel) ands vertical lines represent the SEM. Numbers below the bars indicate proportion of animals responding to the DNA vaccine (top panel); all muscles injected with pCMV-luc expressed luciferase (bottom panel).

In contrast to the success with protein antigens, attempts to augment immune responses induced by a HBsAg-expressing DNA vaccine by the addition of CpG-S ODN 1826 failed. Surprisingly, the immune responses decreased with the addition of CpG-S ODN in a dose-dependent manner (FIG. 6, top panel ). Addition of ODN #1826 to a luciferase reporter gene construct (pCMV-luc, Davis et al., 1993b) resulted in a dose-dependent decrease in luciferase expression (FIG. 6, bottom panel). This indicates that the negative effects of the CpG-S ODN on the DNA vaccine were due to reduced gene expression rather than an effect on the immune response against the gene product.

Figure 7:
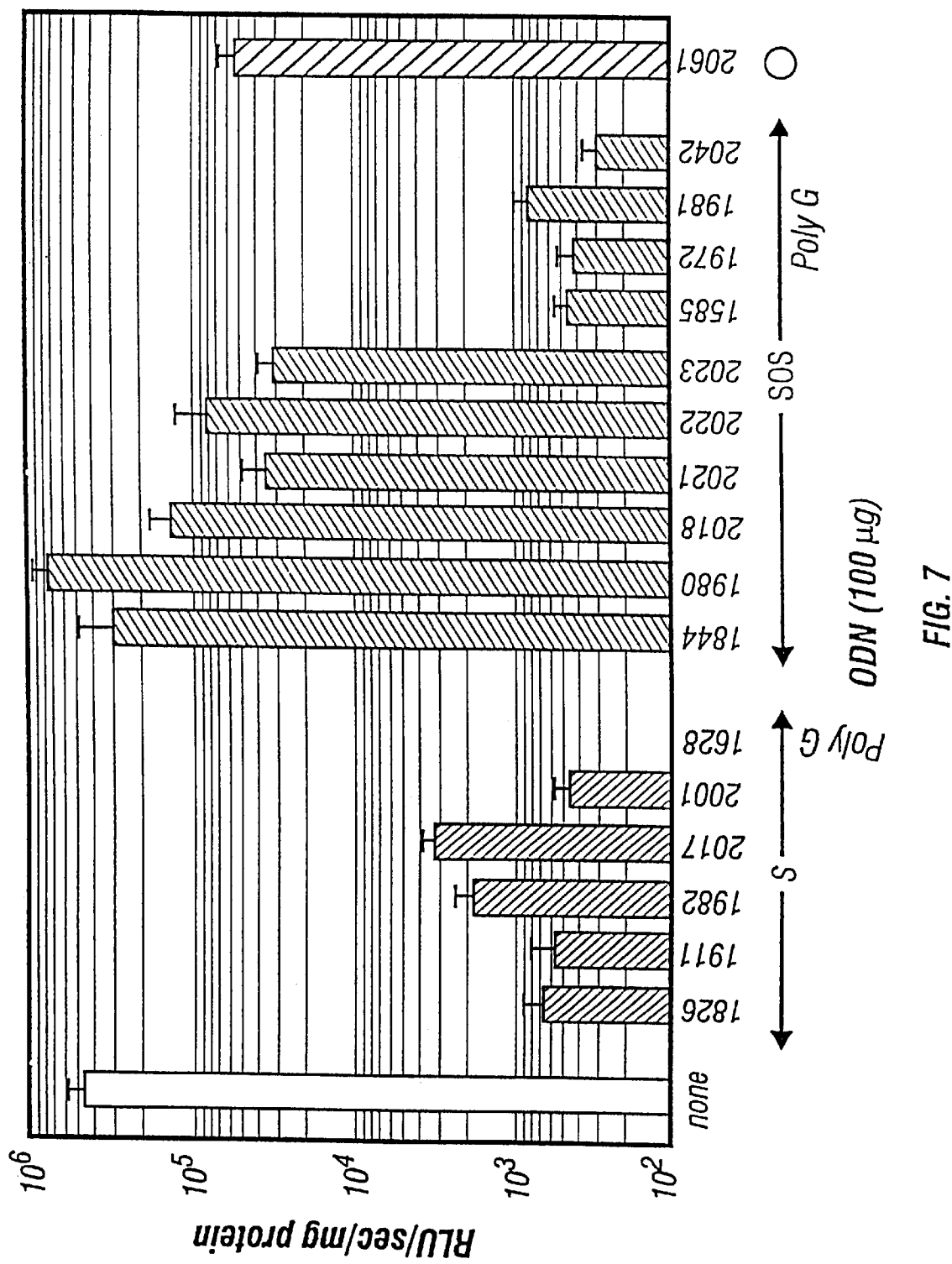
FIG. 7: Interference of ODN with pDNA due to backbone and sequence. The figure shows the interference of ODN with plasmid DNA depends on backbone and sequence. Luciferase activity (RLU/sec/mg protein) in mouse muscles 3 days after they were injected with 10 µg pCMV-luc DNA to which had been added no ODN (none=white bar) or 100 µg of an ODN, which had one of three backbones: phosphorothioate (S=left slanted bars: 1628, 1826, 1911, 1982, 2001 and 2017), phosphodiester (O=thick left slanted bar: 2061), or a phosphorothioate-phosphodiester chimera (SOS=right slanted bars: 1585, 1844, 1972, 1980, 1981, 2018, 2021, 2022, 2023 and 2042). Three S-ODN (1911, 1982 and 2017) and two SOS-ODN (1972 and 2042) did not contain any immunostimulatory CpG motifs. One S-ODN (1628) and three SOS-ODN (1585, 1972, 1981) had poly-G ends and one SOS-ODN (2042) had a poly-G center. The (*) indicates ODN of identical sequence but different backbone: 1826 (S-ODN), 1980 (SOS-ODN) and 2061 (O-ODN). All S-ODN (both CpG and non-CpG) resulted in decreased luciferase activity whereas SOS-ODN did not unless they had poly-G sequences.
Figure 8:
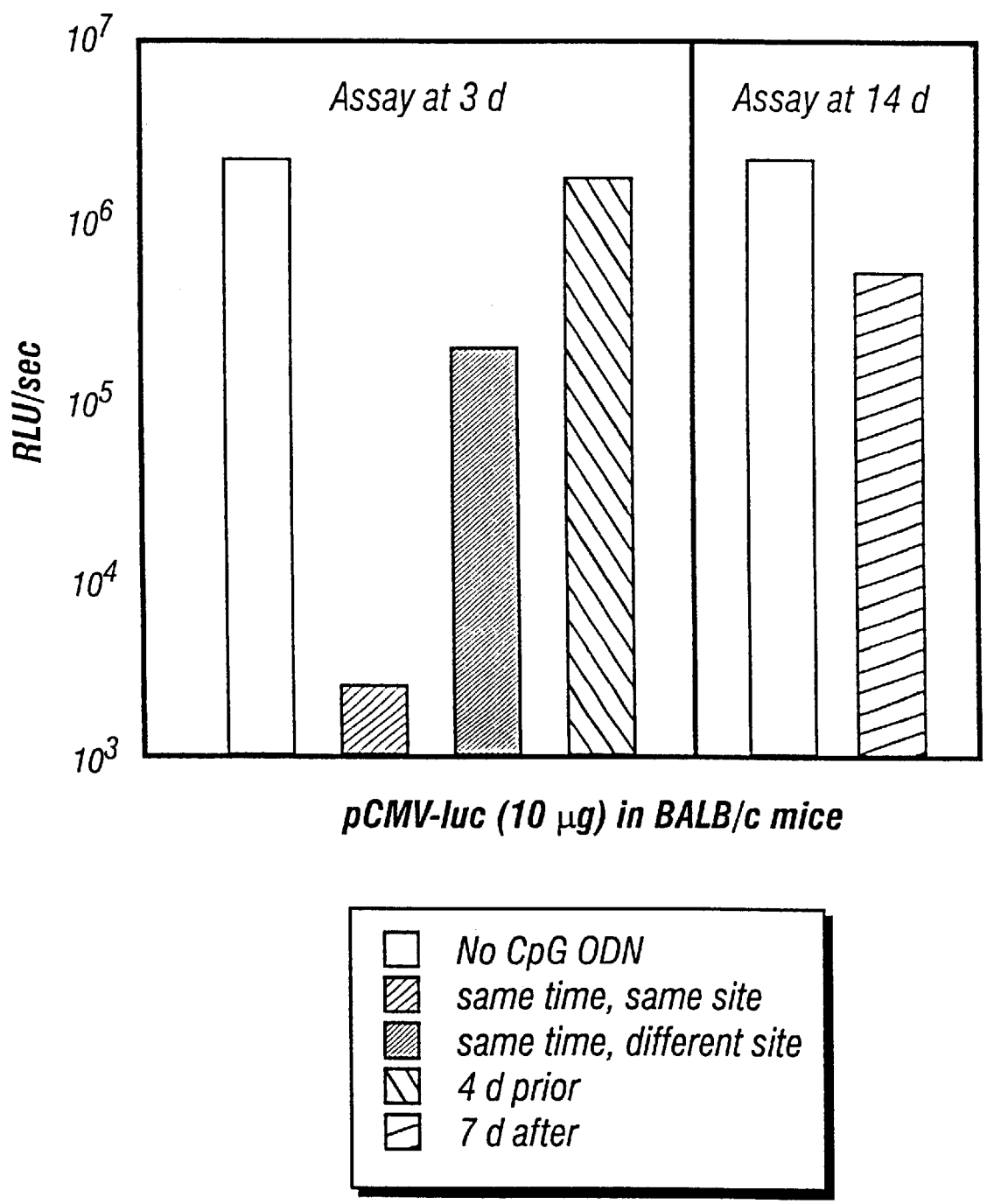
FIG. 8: Temporal and spatial separation of CpG ODN and plasmid DNA. The figure shows the effect of temporal or spatial separation of plasmid DNA and S-ODN on gene expression. Luciferase activity (RLU/sec/mg protein) in mouse muscles 3 or 14 days after they were injected with 10 µg pCMV-luc DNA. Some animals also received 10 jg CpG-S ODN which was mixed with the DNA vaccine or was given at the same time but at a different site, or was given 4 days prior to or 7 days after the DNA vaccine. Only when the ODN was mixed directly with the DNA vaccine did it interfere with gene expression.

ODN #1826 used in the above studies is an ODN with a phosphorothioate backbone (S-ODN) and it is possible that the synthetic sulfur-containing backbone interfered with the ability of the plasmid DNA to transfect target cells. Zhao et al. (1994) investigated the effect of the backbone on binding, uptake and degradation of ODN by mouse splenocytes and found that S-ODN had the highest affinity for ODN-binding sites on the cell membrane and could competitively inhibit binding of ODN made with a natural phosphodiester backbone (O-ODN). A similar blocking of binding might be taking place when S-ODN is mixed with plasmid DNA, which contains a natural phosphodiester backbone like O-ODN. Furthermore, it was shown that the affinity of ODN made with a phophorothioate-phosphodiester chimeric backbone (SOS-ODN) for ODN-binding sites was lower than that of S-ODN (Zhao et al., 1994). Thus, we evaluated the effect of adding SOS-ODN 1980, which has the identical sequence to S-ODN 1826, to pCMV-luc DNA and found that even at a 100 $\mu$g dose, this did not alter the expression of the luciferase reporter gene (FIG. 7). While ODN with a chimeric backbone (SOS-ODN) do not adversely affect the level of gene expression (except when certain sequences such as a poly G are present) (FIG. 7), this is not useful since SOS-ODN are apparently also not sufficiently nuclease-resistant to exert a strong CpG adjuvant effect (Table 12). Administering the CpG S-ODN at a different time or site than the plasmid DNA does not interfere with gene expression either (FIG. 8), however nor do these approaches augment responses to DNA vaccines by administering the CpG S-ODN at a different time or site than the plasmid DNA (Table 12). Thus it appears that the immune system must see the antigen and the CpG-S motif at the same time and the same place to augment antigen-specific responses. Thus, at least for the present, it appears necessary to clone CpG motifs into DNA vaccine vectors in order to take advantage of their adjuvant effect.

EXAMPLE 3

CpG-optimized DNA Vaccines

Figure 9:
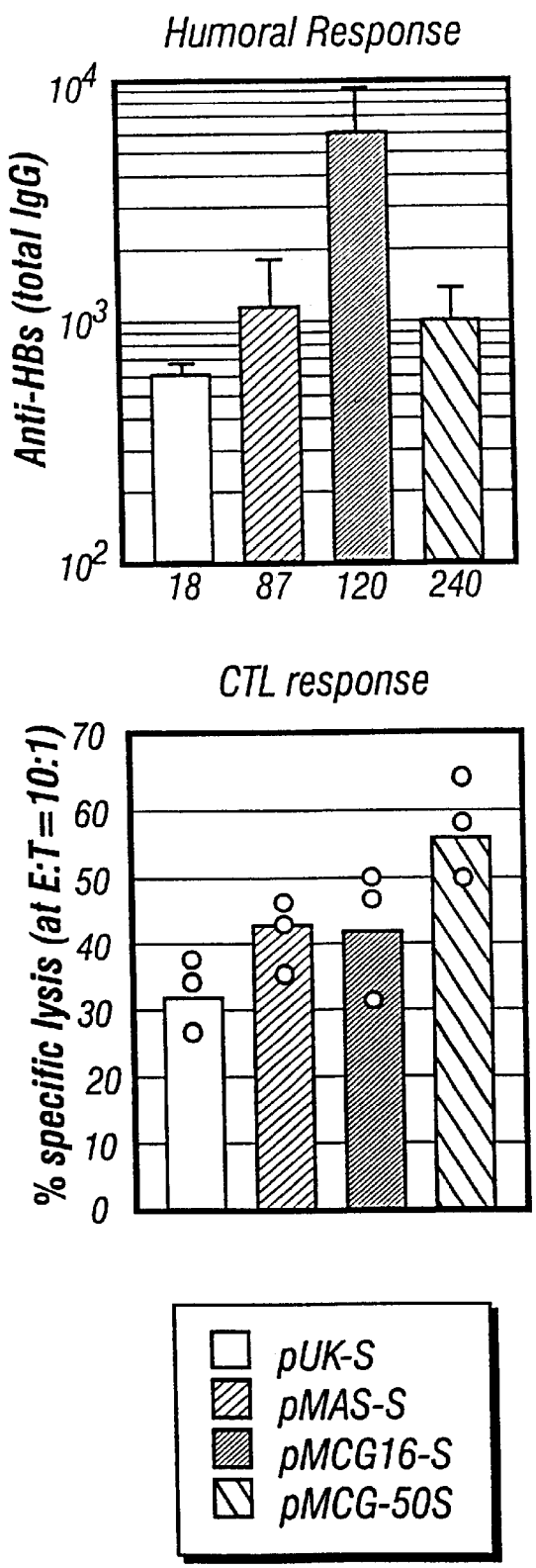
FIG. 9: Immunization of BALB/c mice with CpG-optimized DNA vaccines. The figure shows the enhancement of in vivo immune effects with optimized DNA vaccines. Mice were injected with 10 µg of pUK-S, pMAS-S, pMCG16-S or pMCG50-S plasmid DNA bilaterally (50 µl at 0.1 mg/ml in saline) into the TA muscle. The top panel shows the anti-HBs antibody response at 6 weeks (detected as described in methods). Bars represent the group means (n=5) for ELISA end-point dilution titers (performed in triplicate), and vertical lines represent the standard errors of the mean. The numbers on the bars indicate the ratio of IgG2a:IgG1 antibodies at 4 weeks, as determined in separate assays (also in triplicate) using pooled plasma. The bottom panel shows the cytotoxic T lymphocyte activity in specifically restimulated (5 d) splenocytes taken from mice 8 wk after DNA immunization. Bars represent the group means (n=3) for % specific lysis (performed in triplicate) at an effector:target (E:T) ratio of 10:1, dots represent the individual values. Non-specific lytic activity determined with non-antigen-presenting target cells, which never exceeds 10%, has been subtracted from values with HBsAg-expressing target cells to obtain % specific lysis values.
Figure 10:
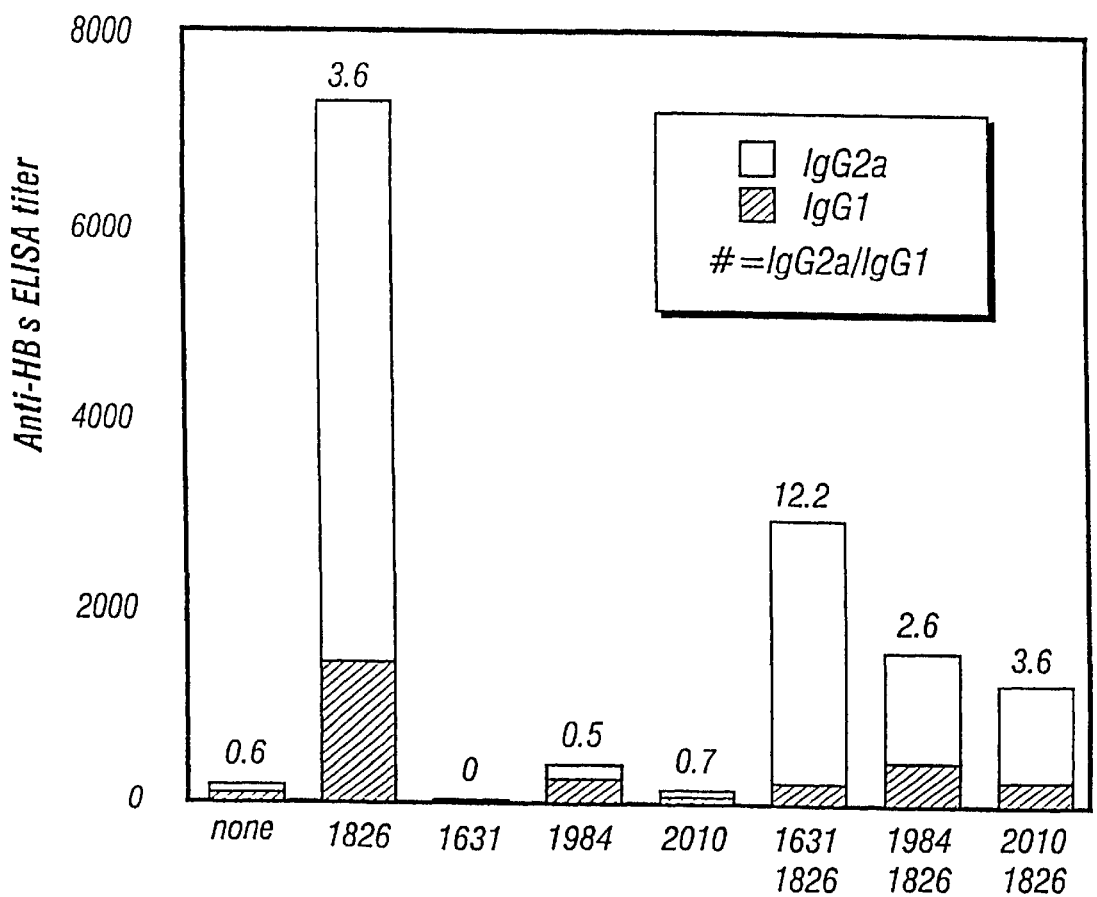
FIG. 10 shows induction of a Th2-like response by a CpG-N motif and inhibition of the Th1-like response induced by a CpG-S motif. Anti-HBs antibody titers (IgG1 and IgG2a subclasses) in BALB/c mice 12 weeks after IM immunization with recombinant HBsAg, which was given alone (none) or with 10 μg stimulatory ODN (1826), 10 μg of neutralizing ODN (1631, CGCGCGCGCGCGCGCGCGCG(SEQ. ID NO: 22); 1984, TCCATGCCGTTCCTGCCGTT(SEQ. ID NO: 7b); or 2010 GCGGCGGGCGGCGCGCGCCC(SEQ. ID NO: 75); CpG dinucleotides are underlined for clarity) or with 10 μg stimulatory ODN+10 μg neutralizing ODN. To improve nuclease resistance for these in vivo experiments, all ODN were phosphorothioate-modified. Each bar represents the group mean (n=10 for none; n=15 for #1826 and n=5 for all other groups) for anti-HBs antibody titers as determined by end-point dilution ELISA assay. Hatched portions of bars indicate antibodies of IgG1 subclass (Th2-like) and white portions indicate IgG2a subclass (Th1-like). The numbers above each bar indicate the IgG2a/IgG1 ratio where a ratio >1 indicates a predominantly Th1-like response and a ratio <1 indicates a predominantly Th2-like response (a value of 0 indicates a complete absence of IgG2a antibodies).

Eliminating 52 of 134 CpG-N motifs from a DNA vaccine markedly enhanced its ml -like function in vivo and immune responses were furter augmented by the addition of CpG-S motifs to the DNA vaccine vectors (FIG. 9).

Titers of antibodies were increased by the removal of CpG-N motifs. With the addition of 16 or 50 CpG-S motifs, humoral responses became increasingly more Thl, with an ever greater proportion of IgG2a antibodies. The anti-BBs titer was higher with 16 than 50 CpG-S motifs, perhaps because the strong cytokine response with the greater number of motifs inhibited antigen expression that was driven by the CMV promoter. Viral promoters such as that from CMV are known to be down-regulated by cytokines such as the IFNs (Gribaudo et al., 1993; Harms & Splitter, 1995; Xiang et al., 1997).

CTL responses were likewise improved by removal of CPG-N motifs, and then more so by the addition of CpG-S motifs to the DNA vaccines.

EXAMPLE 4

CpG-Optiniized Gene Therapy Vectors

Oligodeoxynucleotides (ODN) and DNA Phosphodiester ODN were purchased from Operon Technologies (Alameda, Calif.) and nuclease resistant phosphorothioate ODN were purchased from Oligos Etc. (Wilsonville, Oreg.) or Hybridon Specialty Products (Milford, Mass.). All ODN had undetectable endotoxin levels (less than 1 ng/mg) by Limulus assay (Whittaker Bioproducts, Walkersville, Md.). *E. coli* (strain B) DNA was purchased from Sigma (St. Louis, Mo.), purified by repeated extraction with phenol:chloroform:isoamyl alcohol (25:24:1) and/or Triton X114 extraction and ethanol precipitation and made single stranded by boiling for 10 min followed by cooling on ice for 5 min. Highly purified type 2, 5, and 12 adenoviral DNA was prepared from viral preparations using standard techniques and processed in the same manner as the *E. coli* DNA. Plasmids for DNA vaccination were purified using two rounds of passage over Endo-free columns (Qiagen, Hilden, Germany).

Cell Cultures and ELISA assays for cytokines. ELISA assays were performed using standard techniques and commercially available reagents as previously described (Klinman, D., et al., *Proc. Natl. Acad. Sci. USA*, 93, 2879–2883 (1996); Yi et al., *J. Immunol.*, 157, 5394–5402 (1996)). Standard deviations of the triplicate wells were <10%.

Construction of optimized DNA vectors. The starting material was pUK21-A2, an expression vector containing the immediate early promoter of human cytomegalovirus (CMV IE), the bovine growth hormone (BGH) polyadenylation signal, and the kanamycin resistance gene (Wu and Davis, unpublished). To avoid disrupting the plasmid origin of replication, mutagenesis designed to eliminate CpG-N motifs was restricted to the kanamycin resistance gene and non-essential DNA sequences following the gene. A total of 22 point mutations were introduced to alter 15 CpG-N motifs (a "motif" refers to a hexamer containing one or more CpG dinucleotides) containing 19 CpG dinucleotides, 12 of which were eliminated and 7 of which were transformed into CpG-S motifs. Site-directed mutagenesis was performed by overlap extension PCR as described by Ge et aL (Prosch, S., et al., Biol. Chem., 377, 195–201 (1996)). The 1.3 kb AlwN I-EcoO109I fragment of pUK21-A2, which contained all 22 nucleotides to be mutated, was used as the template for PCR. The 1.3 kb fragment was regenerated by four rounds of overlap extension PCR using appropriate mutagenic primers, and substituted for the original AlwN I-EcoO109I fragment, resulting in pUK21-B2. All the mutations were confirmed by sequencing.

Another 37 CpG-N motifs were removed by replacing the f1 origin with a multiple cloning site. Oligonucleotides 5' G C C C TAT T T T A A AT T C G A A A G TA C T G - GACCTGTTAACA 3' (SEQ ID NO:20) and its complementary strand 5' CGTGTTAACAGGTCCAGTACTTTC- GAATTTAAAATAG 3' (SEQ ID NO:21) were synthesized, and 5'-phosphorylated. Annealing of these two phosphorylated-oligos resulted in a 35 bp double-stranded DNA fragment containing four unique restriction enzyme sites (Dra I, Sca I, Ava II, Hpa I) and two sticky ends. Replacing the 0.6 kb Nar I-EcoO109I fragment of pUK21-

B2, which contained the entire fi ori, with this double-stranded DNA fragment resulted in the master vector pMAS.

Next, different numbers of CpG-S motifs were inserted into the vector by allowing self-ligation of a 20bp DNA fragment with the sequence 5' GACTCCATGAMTTCCT-GAMTTTCCATGACTTCCTGACUTTG 3' (SEQ ID NO:12) with a complementary strand and inserting different numbers of copies into the Ava II site of pMAS. Recombinant clones were screened and the two vectors were chosen for further testing with 16 and 50 CpG-S motifs, and named pMCG16 and pMCG50 respectively.

Figure 11:
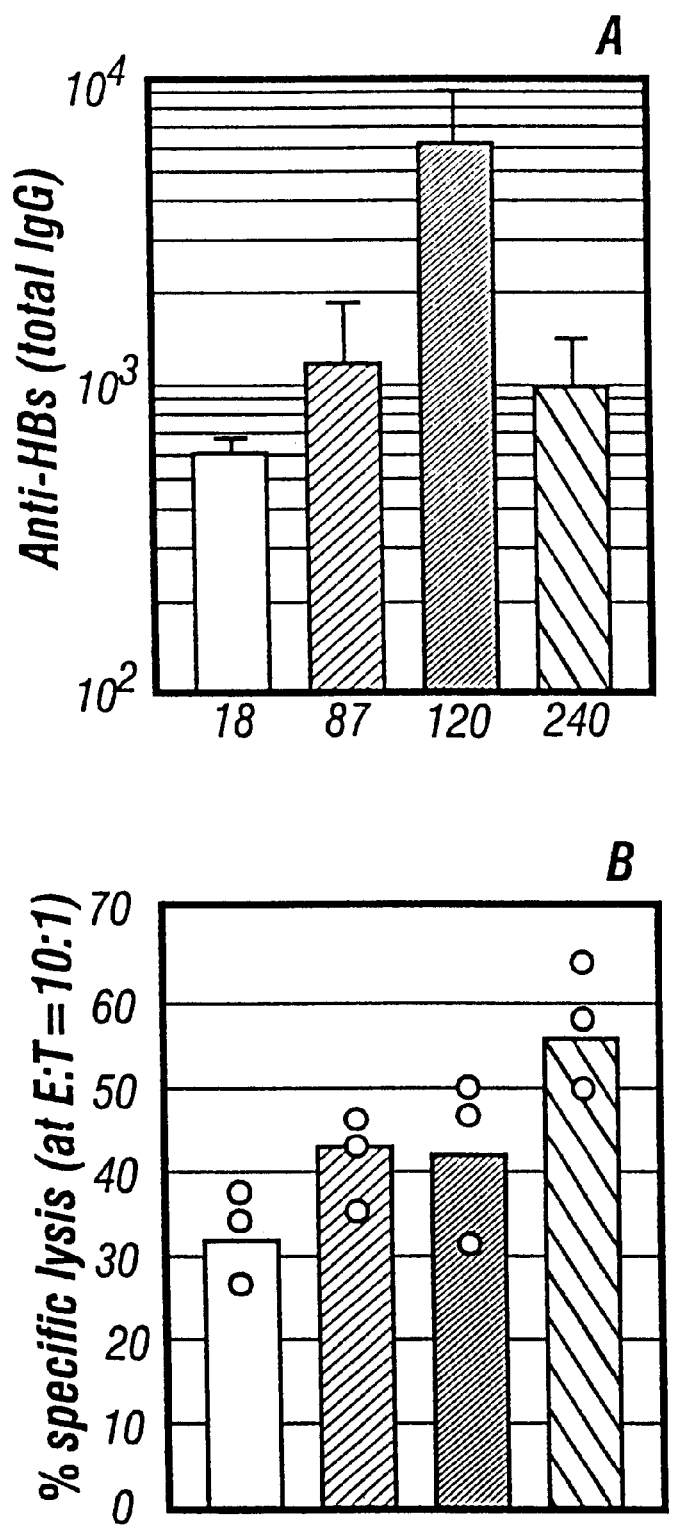
FIG. 11 shows enhancement of in vivo immune effects with optimized DNA vaccines. Mice were injected with 10 μg of pUK-S (white bars), pMAS-S (right slanted bars), pMCG16-S (thin right slanted bars) or pMCG50-S (left slanted bars) plasmid DNA bilaterally (50 μl at 0.1 mg/ml in saline) into the TA muscle. Panel A: The anti-HBs antibody response at 6 weeks (detected as described in methods). Bars represent the group means (n=5) for ELISA end-point dilution titers (performed in triplicate), and vertical lines represent the standard errors of the mean. The numbers on the bars indicate the ratio of IgG2a:IgG1 antibodies at 4 weeks, as determined in separate assays (also in triplicate) using pooled plasma. Panel B: Cytotoxic T lymphocyte activity in specifically restimulated (5 d) splenocytes taken from mice 8 wk after DNA immunization. Bars represent the group means (n=3) for % specific lysis (performed in triplicate) at an effector:target (E:T) ratio of 10:1, dots represent the individual values. Non-specific lytic activity determined with non-antigen-presenting target cells, which never exceeds 10%, has been subtracted from values with HBsAg-expressing target cells to obtain % specific lysis values.

To create a DNA vaccine, the S gene encoding ay subtype of hepatitis B surface antigen (liBsAg) was amplified by PCR and cloned into the EcoRV - PstI sites of the vectors, resulting in pUK-S, pMAS-S, pMCG16-S, and pMCG50-S respectively. Vector sequences were confirmed by sequencing and have been deposited in GenBank under accession numbers AFO53406 (pUK-S), AFO53407 (pMAS-S), AFO53408 (pMCG16-S), and AFO53409 (pMCG50-S).

Immunization of mice against HBsAg: Immunization of 6–8 wk old female BALB/c mice (Charles River, Montreal, QC) was by injection into the tibialis anterior muscle (TA) of 1 μg recombinant HBsAg or 10 μg HBsAg-expressing DNA vaccine (Chace, J. H., et al., Immunopath, In press (1997)). Assay for antibodies against HBsAg (anti-HBs) was by end point dilution and for cytotoxic T lymphocytes (CTL) was by chromium release assay as described previously[19]. Both the protein (±ODN) and DNA vaccines were resuspended in saline for injection.

EXAMPLE 5

Type 12 adenoviral DNA is immune stimulatory, but types 2 and 5 adenoviral DNA are immune neutralizing. To investigate possible functional differences in the immune effects of various prokaryotic DNAs, we determined their ability to induce cytokine secretion from human PBMC. In contrast to bacterial DNA and genomic DNA from type 12 adenovirus, DNA from types 2 and 5 adenovirus failed to induce cytokine production (Table 8). In fact, despite their similar frequency of CpG dinucleotides, type 2 or 5 adenoviral DNA severely reduced the cytokine expression induced by co-administered immunostimulatory *E. coli* genomic DNA (Table 9). This indicates that type 2 and 5 adenoviral DNA does not simply lack CpG-S motifs, but contains sequences that actively suppress those in *E. coli* DNA.

Identification of putative immune neutralizing CpG-N motifs in type 2 and 5 adenoviral genomes. To identify possible non-random skewing of the bases flanking the CpG dinucleotides in the various adenoviral genomes, we examined their frequency of all 4096 hexamers. The six most common hexamers in the type 2 adenoviral genome are shown in Table 7, along with their frequency in the Type 12 and *E. coli* genomes. Remarkably, all of these over-represented hexamers contain either direct repeats of CpG dinucleotides, or CpGs that are preceded by a C and/or followed by a G. These CpG-N motifs are approximately three to six fold more common in the inunune inhibitory type 2 and 5 adenoviral genomes than in those of immune-stimulatory type 12 adenoviral, *E. coli* or non-stimulatory human genomic DNAs (Table 7). This hexamer analysis further revealed that the frequency of hexarners containing CpG-S motifs (e.g., GACGTT or AACGTT) in the type 2 adenoviral genome is as low as that in the human genome: only ⅓ to ⅙ of that in *E. coli* and type 12 adenoviral DNA (Table 7).

Effect of CpG-N motifs on the immune stimulatory effects of CpG-S motifs. To determine whether these over-represented CpG-N motifs could explain the neutralizing properties of type 2 and 5 adenoviral DNA, we tested the in vitro immune effects of synthetic oligodeoxynucleotides bearing a CpG-S motif, one or more CpG-N motifs, or combinations of both. An ODN containing a single CpG-S motif induces spleen cell production of IL-6, IL-12, and IFN-γ (ODN 1619, Table 13). However, when the 3' end of this ODN was modified by substituting either repeating CpG dinucleotides or a CpG dinucleotide preceded by a C, the level of cytokine production was reduced by approximately 50% (ODN 1952 and 1953, Table 13). ODN consisting exclusively of these neutralizing CpG (CpG-N) motifs induced little or no cytokine production (Table 14). Indeed, addition of ODN containing one or more CpG-N motifs to spleen cells along with the CpG-S ODN 1619 caused a substantial decrease in the induction of IL-12 expression indicating that the neutralizing effects can be exerted in trans (Table 14).

To determine whether the in vivo immune activation by ODN containing CpG-S motifs would be reversed by CpG-N motifs, we immunized mice with recombinant hepatitis B surface antigen (IBsAg), with or without nuclease resistant phosphorothioate-modified ODN containing various types of CpG motifs. As expected, a CpG-S ODN promoted a high titer of antibodies against HBsAg (anti-HBs antibodies) which were predominantly of the IgG2a subclass, indicating a ThI-type immune response (FIG. 10; ODN 1826). The various CpG-N ODN induced either little or no production of anti-HBs antibodies (ODN 1631, 1984, and 2010) (FIG. 10). Mice immunized with combinations of CpG-S and CpG-N ODN had a reduced level of anti-HBs antibodies compared to mice immunized with CpG-S ODN alone, but these were still predominantly IgG2a (FIG. 10).

Enhanced DNA vaccination by deletion of plasmid CpIGN motifs. DNA vaccines can be highly effective inducers of Th1-like immune responses (Raz, E., et al., *Proc. Natl. Sci. Acad. USA*, 93, 5141–5145 (1996); Donnelly , J. J., et al., *Ann. Rev. Immunol.*, 15, 617–648 (1997)). Based on the in vivo and in vitro effects of CpG-N motifs, we hypothesized that their presence within a DNA vaccine would decrease its immunostimulatory effects. The starting vector, pUK21-A2, contained 254 CpG dinucleotides, of which 134 were within CpG-N motifs. In order to test the hypothesis that these CpG-N motifs adversely affected the efficacy of this vector for DNA-based vaccination, the number of CpG-N motifs was reduced, either by mutation or deletion. Since mutations in the plasmid origin of replication interfere with replication of the plasmid, we restricted our initial mutations to the kanainycin resistance gene and a nonessential flanking region. We were able to eliminate 19 CpG dinucleotides contained within 15 of the 20 CpG-N motifs in these regions without changing the protein sequence. The F1 origin of replication containing 37 CpG-N motifs and only 17 other CpG dinucleotides was then deleted, creating the vector pMAS. This vector was further modified by the introduction of 16 or 50 CpG-S motifs, yielding vectors pMCG16 and pMCG50 respectively. The S gene for HBsAg was then cloned into these vectors downstream from the CMV promoter, to make pUK-S, pMAS-S, pMCG16-S, and pMCG50-S respectively.

When tested for their ability to induce cytoline (IL-6 and IL-12) secretion from cultured spleen cells, we found that the pMAS-S, pMCGI 6-S and pMCG(50-S vectors had significantly enhanced immune stimulatory activity compared to pUK-S. When used as a DNA vaccine, the anti-HBs response at 4 and 6 weeks was substantially stronger with DNA vaccines from which CpG-N motifs had been deleted, and even more so when 16 CpG-S motifs had been inserted. The vector with 50 CpG-S motifs, however, was less effective at inducing antibody production than that with 16 motifs. (FIG. 11, panel A). Removal of CpG-N motifs and addition of CpG-S motifs resulted in a more than three-fold increase in the proportion of IgG2a relative to IgG1 anti-HBs antibodies, indicating an enhanced Th-1 response. This accentuated TH1 response also was demonstrated by the striking progressive increases in CTL responses induced by vectors from which CpG-N motifs were deleted and/or CpG-S motifs added (FIG. 11, panel B).

The discovery of immune activating CpG-S motifs in bacterial DNA has led to the realization that aside from encoding genetic information, DNA can also function as a signal transducing molecule. Our present results demonstrate that genomic DNA from type 12 adenovirus is immune stimulatory, compatible with its relatively high content of CpG-S motifs. In contrast, genomic DNA from type 2 and 5 adenoviruses is not stimulatory, but rather is immune neutralizing and blocks the cytokine induction of bacterial DNA (Tables 8 and 9). To identify possible differences in the CpG motifs present in these different adenoviral genomes, analyzed the genomic frequency of all hexamer sequences was analyzed. This analysis demonstrated that only the type 2 and 5 adenoviral genomes had a dramatic overrepresentation of CpG motifs containing direct repeats of CpG dinucleotides and/or CpGs preceded by a C and/or followed by a G (Table 7). Synthetic ODN containing such putative immune neutralizing (CpG-N) motifs not only did not induce cytokine production in vitro, but also inhibited the ability of an immune stimulatory CpG-S motif to induce cytokine expression (Tables 13, 14). These studies reveal that there are immune neutralizing CpG-N as well as stimulatory CpG-S motifs and that there is a surprisingly complex role for the bases flanking CpG dinucleotides in determining these immune effects. In general, CpG-N motifs oppose CpG-S motifs in cis or trans. The mechanism through which CpG-N motifs work is not yet clear, but does not appear to involve competition for cell uptake or binding to a CpG-S-specific binding protein. Further studies are underway to determine the molecular mechanisms through which CpG-N and CpG-S motifs exert their respective immune effects.

The hexamers that contain CpG-N motifs are from 15 to 30 times more common in type 2 and 5 adenoviral genomes than those that contain immune stimulatory CpG-S motifs. However, in type 12 adenoviral genomes the frequencies of hexamers containing CpG-N and CpG-S motifs do not differ substantially from chance. These data suggest that the immune neutralizing effects of types 2 and 5 adenoviral DNA are not merely a result of their propagation in eukaryotic cells, but rather are due to the overall excess of CpG-N compared to CpG-S motifs. It is tempting to speculate that the marked over-representation of CpG-N motifs in the genomes of types 2 and 5 adenovirus may contribute to the biologic properties, such as persistent infection of lymphocytes, which distinguish them from type 12 adenovirus. The presence of large numbers of CpG-N motifs within these adenoviral genomes may have played an important role in the evolution of this virus by enabling it to avoid triggering CpG-induced immune defenses. It will be interesting to determine the general distribution of CpG-N and CpG-S motifs in different families of microbial and viral genomes, and to explore their possible roles in disease pathogenesis.

CpG-N motifs are also over-represented in the human genome, where their hexamers are approximately two to five-fold more common than CPG-S motifs. While this skewing is far less marked than that in adenoviral DNA, it would still be expected to reduce or eliminate any immune stimulatory effect from the unmethylated CpGs present in CpG islands within vertebrate DNA. We and others have found that even when predominantly or completely unmethylated, vertebrate DNA is still not immune stimulatory (A. Krieg and P. Jones, unpublished data) (Sun, S., et al., *J. Immunol.*, 159:3119–3125 (1997)) which is in keeping with its predominance of CpG-N motifs (Table 7). Given the overall level of CpG suppression in the human genome, the molecular mechanisms responsible for the skewing of the frequency of CpG-N to CpG-S motifs are unclear. Such a distortion from the expected random patterns would seem to require the existence of pathways that preferentially mutate the flanking bases of CPG-S motifs in vertebrate genomes, but do not affect CPG-N motifs. Indeed, statistical analyses of vertebrate genomes have provided evidence that CpGs flanked by A or T (as in CpG-S motifs) mutate at a faster rate than CpGs flanked by C or G (Bains, W., et al., *Mutation Res.*, 267:43–54 (1992)).

Based on our in vitro experiments we hypothesized that the presence of CpG-N motifs in DNA vaccines interferes with the induction of the desired immune response. Indeed, the present study demonstrates that elimination of CpG-N motifs from a DNA vaccine leads to improved induction of antibodies. By removing 52 of the CPG-N motifs from a DNA vaccine (45 were deleted and 7 turned into CpG-S motifs) the serologic response was more than doubled; by then adding an additional 16 CpG-S motifs, the response was enhanced nearly 10 fold (FIG. 11, panel A). Likewise, CTL responses were improved by removing CpG-N motifs and even more so by adding 16 or 50 CpG-S motifs (FIG. 11, panel B). These increased responses are especially notable in view of the fact that the total number of CpG dinucleotides in the mutated vaccines is considerably below the original number.

The finding that the vector with 50 CpG-S motifs was inferior to that with 16 motifs for induction of humoral immunity was unexpected, and may be secondary to CpG-induced production of type I interferons, and subsequent reduction in the amount of antigen expressed. The decreased antibody response induced by pMCG50-S seems unlikely to be explained by vector instability since this vector gave the best CTL responses (FIG. 11, panel B). Although the pMCG50-S vector was slightly larger than pMCG16-S, the 10 μg dose still contained 93% as many plasmid copies as it did pMCG16-S, so lower copy number is unlikely to account for the reduced antibody levels The current generation of DNA vaccines are quite effective in mice, but much less effective in primates (Davis, H. L., et al., *Proc. Natl. Acad. Sci. USA*, 93:7213–7218 (1996); Letvin, N. L., et al., *Proc. Nati. Acad. Sci. USA*, 94:9378–9383 (1997); Fuller, D. H., et al., *J Med. Primatol.*, 25:236–241 (1996); Lu, S., et al., *J. Virol.*, 70:3978–3991 (1996); Liu, M. A., et al., *Vaccine*, 15:909–919 (1997); Prince, A. M., et al., *Vaccine*, 15:9196–919 (1997); Gramzinski, R. A., et al., *Molec. Med.*, 4:109–119 (1998)). Our present results indicate that attaining the full clinical potential of DNA vaccines will require using engineered vectors in which CpG-N motifs have been deleted, and CpG-S motifs added.

On the other hand, the field of gene therapy may benefit from the discovery of CpG-N motifs through their insertion into gene transfer vectors to prevent or reduce the induction of host immune responses. Most of the CpG-N motifs in the adenoviral genome are in the left hand (5') side, which is generally partially or totally deleted for the preparation of gene therapy vectors, especially with the "gutless" vectors (Kochanek, S., et al., *Proc. Natl. Acad. Sci. USA*, 93:5731–5736 (1996)). This could lead to an enhanced CpG-S effect. Since nucleic acids produced in viral vectors are unmethylated, they may produce inflammatory effects if they contain a relative excess of CpG-S over CpG-N motifs and are delivered at an effective concentration (about 1 µg/ml). Gene therapy studies with adenoviral vectors have used doses up to 10 infectious units (IU)/ml (which contains 0.4 µg of DNA/ml based on the genome size of 36 kb). Given that approximately 99% of adenoviral particles are noninfectious, this corresponds to a DNA dose of approximately 40 µg/ml, which is well within the range at which CpG DNA causes in vivo immune stimulatory effects; just 10 gg/mouse induces IFN-γ production acts as an adjuvant for immunization (D)avis, H. L., et al., *J. Immunol.*, 160:870–876 (1998); Chu, R. S., et al., *J. Exp.Med.*, 186:1623–1631 (1997); Lipford, G. B., et al., *Eur. J. Immunol.*, 27:2340–2344 (1997); Weiner, G. J., et al., *Proc. Natl. Acad. Sci. USA*, 94:10833 (1997); Moldoveanu, Z., et al., Vaccine, In press (1998)), and causes acute pulmonary inflammation when delivered into mouse airways (Schwartz, D., et al., *J. Clin. Invest.*, 100:68–73 (1997)). Multiple mechanisms besides the presence of CpG-S DNA are doubtless responsible for the inflammatory responses that have limited the therapeutic development of adenoviral vectors (Newman, K. D., et al., *J. Clin. Invest.*, 96:2955–2965 (1995); Zabner, J., et al., *J. Clin. Invest.*, 97:1504–1511 (1996)). Nonetheless, our present results suggest that consideration be given to the maintenance or insertion of CpG-N motifs in adenoviral vectors, and to the engineering of backbones and inserts so that CpG-S motifs are mutated in order to reduce immune activation.

In recent years, it has become clear that effective gene expression need not require a viral delivery system. The use of plasmids for gene delivery (with or without lipids or other formulations) avoids some of the problems of viral vectors. On the other hand, much larger doses of DNA are typically required, since delivery is far less efficient than with a targeted system such as a virus. For example, effective gene expression in mice typically may require 500–1000 µg DNA/mouse (Philip, R., et al., *J. Biol. Chem.*, 268:16087–16090 (1993); Wang, C., et al., *J. Clin. Invest.*, 95:1710–1715 (1995)). A recent human clinical trial using lipid/DNA complexes and naked DNA for delivery of CFTR to the nasal epithelium of patients with cystic fibrosis used doses of 1.25 mg of plasmid/nostril (Zabner, J., et al., *J Clin. Invest.*, 100:1529–1537 (1997)). The successful application of naked DNA expression vectors for gene therapy will depend on the safety of repeatedly delivering high doses of DNA. Since the plasmids used for gene therapy typically contain several hundred unmethylated CpG dinucleotides, many of which are in CpG-S motifs, some immune activation may be expected to occur. Indeed, mice given repeated doses of just 10 µg of plasmid DNA daily develop elevated lymphocyte levels and several humans who received intranasal plasmid DNA had elevated serum IL-6 levels (Philip, R., et al., *J. Biol Chem.*, 268:16087–16090 (1993)). Furthermore, delivery of 4 mg of a gene therapy plasmid to cystic fibrosis patients in a recent clinical trial caused acute onset of symptoms compatible with immune activation, including fever, chills, and pulmonary congestion. Another reason to avoid the presence of CpG-S motifs in gene therapy vectors is that the cytokines that are produced due to the immune stimulation may reduce plasmid vector expression, especially when this is driven by viral promoters (Raz, E., et al., *Proc. Natl. Acad. Sci. USA*, 93:5141–5145 (1996)).

It is, therefore, highly desirable to develop improved gene delivery systems with reduced immune activation. It is not possible to simply methylate tie CpG-S dinucleotides in gene therapy plasmids, since methylation of promoters abolishes or severely reduces their activity. The only promoter resistant to methylation-induced silencing is the MMTV promoter, which contains no essential CpGs, but is fairly weak. In any case, even when the promoter is unmethylated, expression is still greatly reduced if the coding sequences are methylated. In fact, even the strong CMV IE promoter is completely inactivated by CpG methylation. Deletion of all CpGs from an expression plasmid is not feasible since many of these are located in the origin of replication (approximately 1.2 Kb long) where even single base changes can dramatically reduce plasmid replication. For these reasons, we propose that addition of CpG-N motifs, and/or mutation or conversion of CpG-S to CpG-N motifs may lead to the generation of less immune stimulatory vectors for gene therapy. Studies to investigate this possibility are under way.

TABLE 1

Primers used for site-directed mutagenesis.
Mutated nucleotides are underlined. Restriction
enzyme sites for cloning are indicated in bold.

Forward primers:

| Name | Pos | Sequence | | |
|---|---|---|---|---|
| Mu-0F | | 5' GTCTCTAGACAGCCACTGGTAACAGGATT 3' (845) | | (SEQ ID NO: 23) |
| Mu-1F | (1144) | 5' GTCGTTGTGTCGTCAAGTCAGCGTAATGC 3' (1172) | | (SEQ ID NO: 24) |
| Mu-2F | (1285) | 5' TCGTTTCTGTAATGAAGGAG 3' (1304) | | (SEQ ID NO: 25) |
| Mu-3F | (1315) | 5' AAGGCAGTTCCATAGGATGG 3' (1334) | | (SEQ ID NO: 26) |
| Mu-(4 + 5)F | (1348) | 5' TCGATCTGCGATTCCAACTCGTCCAACATCAATAC 3' (1382) | | (SEQ ID NO: 27) |
| Mu-6F | (1453) | 5' TGGTGAGAATGGCAAAAGTT 3' (1472) | | (SEQ ID NO: 28) |
| Mu-7F | (1548) | 5' CATTATTCATTCGTGATTGCG 3' (1568) | | (SEQ ID NO: 29) |
| Mu-8F | (1633) | 5' ACGTCTCAGGAACACTGCCAGCGC 3' (1656) | | (SEQ ID NO: 30) |
| Mu-9F | (1717) | 5' AGGGATCGCAGTGGTGAGTA 3' (1736) | | (SEQ ID NO: 31) |

TABLE 1-continued

Primers used for site-directed mutagenesis.
Mutated nucleotides are underlined. Restriction
enzyme sites for cloning are indicated in bold.

| | | | |
|---|---|---|---|
| Mu-10F | (1759) | 5' TATAAAATGCTTGATGGTCGG 3' (1779) | (SEQ ID NO: 32) |
| Mu-(11 + 12)F | (1777) | 5' GGGAAGAGGCATAAATTCTTGTCAGCCAGTTTAGTC 3' (1811) | (SEQ ID NO: 33) |
| Mu-13F | (1882) | 5' TGGCTTCCCATACAAGCGAT 3' (1901) | (SEQ ID NO: 34) |
| Mu-14F | (1924) | 5' TACATTATCGCGAGCCCATT 3' (1943) | (SEQ ID NO: 35) |
| Mu-15F | (1984) | 5' TGGCCTCGACGTTTCCCGT 3' (2002) | (SEQ ID NO: 36) |

Reverse primers:

| | | | |
|---|---|---|---|
| Mu-0R | | 5' ATCGAATTCAGGGCCTCGTGATACGCCTA 3' (2160) | (SEQ ID NO: 37) |
| Mu-1R | (1163) | 5' TGACTTGACGACACAACGACAGCTCATGACCAAAATCCC 3' (1125) | (SEQ ID NO: 38) |
| Mu-2R | (1304) | 5' CTCCTTCATTACAGAAACGACTTTTTCAAAAATATGGTA 3' (1266) | (SEQ ID NO: 39) |
| Mu-3R | (1334) | 5' CCATCCTATGGAACTGCCTTGGTGAGTTTTCTCCTTC 3' (1298) | (SEQ ID NO: 40) |
| Mu-(4 + 5)R | (1367) | 5' GAGTTGGAATCGCAGATCGATACCAGGATCTTGC 3' (1334) | (SEQ ID NO: 41) |
| Mu-6R | (1472) | 5' AACTTTTGCCATTCTCACCAGATTCAGTCGTCACTCA 3' (1436) | (SEQ ID NO: 42) |
| Mu-7R | (1568) | 5' CGCAATCACGAATGAATAATGGTTTGGTTGATGCGAGTG 3' (1530) | (SEQ ID NO: 43) |
| Mu-8R | (1652) | 5' TGGCAGTGTTCCTGAGACGTTTGCATTCGATTCCTGTT 3' (1615) | (SEQ ID NO: 44) |
| Mu-9R | (1736) | 5' TACTCACCACTGCGATCCCTGGAAAAACAGCATTCCAG 3' (1736) | (SEQ ID NO: 45) |
| Mu-10R | (1779) | 5' CCGACCATCAAGCATTTTATACGTACTCCTGATGATGCA 3' (1741) | (SEQ ID NO: 46) |
| Mu-(11 + 12) | (1796) | 5' CAGAATTTATGCCTCTTCCCACCATCAAGCATTTTATAC 3' (1758) | (SEQ ID NO: 47) |
| Mu-13R | (1901) | 5' ATCGCTTGTATGGGAAGCCAGATGCGCCAGAGTTGTTT 3' (1882) | (SEQ ID NO: 48) |
| Mu-14R | (1943) | 5' AATGGGCTCGCGATAATGTAGGGCAATCAGGTGCGAC 3' (1907) | (SEQ ID NO: 49) |
| Mu-15R | (2002) | 5' ACGGGAAACGTCGAGGCCACGATTAAATTCCAACATGG 5' (1965) | (SEQ ID NO: 50) |

(SEQ ID NO:23–50, respectively)

TABLE 2

Nucleotide and amino acid sequences of the AlwNI-EcoO109I fragment (SEQ ID NO:80)

```
kan(wt)  2180  AAGGGCCTCG TGATACGCCT ATTTTTATAG GTTAATGTCA TGGGGGGGGG GGGGAAAGCC
kan(wt)  2120  ACGTTGTGTC TCAAAATCTC TGATGTTACA TTGCACAAGA TAAAAATATA TCATCATGAA
kan(wt)  2060  CAATAAAACT GTCTGCTTAC ATAAACAGTA ATACAAGGGG TGTTATGAGC CATATTCAAC
kan(mu)
ORF                                                                M  S  H  I  Q kan(wt)  2000  GGGAAACGTC GAGGCCGCGA TTAAATTCCA ACATGGATGC TGATTTATAT GGGTATAAAT
kan(mu)                            A
ORF            R  E  T  S  R  P  R      L  N  S  N  M  D  A  D  L  Y  G  Y  K kan(wt)  1940  GGGCTCGCGA TAATGTCGGG CAATCAGGTG CGACAATCTA TCGCTTGTAT GGGAAGCCCG
kan(mu)                         A                                              A
ORF            W  A  R  D  N  V  G  Q  S  G  A  T  I  Y  R  L  Y  G  K  P kan(wt)  1880  ATGCGCCAGA GTTGTTTCTG AAACATGGCA AAGGTAGCGT TGCCAATGAT GTTACAGATG
kan(mu)
ORF            D  A  P  E  L  F  L  K  H  G  K  G  S  V  A  N  D  V  T  D kan(wt)  1820  AGATGGTCAG ACTAAACTGG CTGACGGAAT TTATGCCTCT TCCGACCATC AAGCATTTTA
kan(mu)                                   A                    C
ORF            E  M  V  R  L  N  W  L  T  E  F  M  P  L  P  T  I  K  H  F kan(wt)  1760  TCCGTACTCC TGATGATGCA TGGTTACTCA CCACTGCGAT CCCCGGAAAA ACAGCATTCC
kan(mu)            A                                               T
ORF            I  R  T  P  D  D  A  W  L  L  T  A  I  P  G  K  T  A  F
```

TABLE 2-continued

Nucleotide and amino acid sequences of the AlwNI-EcoO1091 fragment (SEQ ID NO:80)

```
kan(wt)   1700  AGGTATTAGA AGAATATCCT GATTCAGGTG AAAATATTGT TGATGCGCTG GCAGTGTTCC
kan(mu)
ORF              Q  V  L  E  E  Y  P  D  S  G  E  N  I  V  D  A  L  A  V  F kan(wt)   1640  TGCCGCCGGTT GCATTCGATT CCTGTTTGTA ATTGTCCTTT TAACAGCGAT CGCGTATTTC
kan(mu)           A  A  A
ORF              L  R  R  L  H  S  I  P  V  C  N  C  P  F  N  S  D  R  V  F kan(wt)   1580  GTCTCGCTCA GGCGCAATCA CGAATGAATA ACGGTTTGGT TGATGCGAGT GATTTTGATG
kan(mu)                                              T
ORF              R  L  A  Q  A  Q  S  R  W  N  N  G  L  V  D  A  S  D  F  D kan(wt)   1520  ACGAGCGTAA TGGCTGGCCT GTTGAACAAG TCTGGAAAGA AATGCATAAA CTTTTGCCAT
kan(mu)
ORF              D  E  R  N  G  W  P  V  E  Q  V  W  K  E  M  H  K  L  L  P kan(wt)   1460  TCTCACCGGA TTCAGTCGTC ACTCATGGTG ATTTCTCACT TGATAACCTT ATTTTTGACG
kan(mu)               A
ORF              F  S  P  D  S  V  V  T  H  G  D  F  S  L  D  N  L  I  F  D kan(wt)   1400  AGGGGAAATT AATAGGTTGT ATTGATGTTG GACGAGTCGG AATCGCAGAC CGATACCAGG
kan(mu)                                                T              T
ORF              E  G  K  L  I  G  C  I  D  V  G  R  V  G  I  A  D  R  Y  Q kan(wt)   1340  ATCTTGCCAT CCTATGGAAC TGCCTCGGTG AGTTTTCTCC TTCATTACAG AAACGGCTTT
kan(mu)                                     T                              T
ORF              D  L  A  I  L  W  N  C  L  G  E  F  S  P  S  L  Q  K  R  L kan(wt)   1280  TTCAAAAATA TGGTATTGAT AATCCTGATA TGAATAAATT GCAGTTTCAT TTGATGCTCG
kan(mu)
ORF              F  Q  K  Y  G  I  D  N  P  D  M  N  K  L  Q  F  H  L  M  L kan(wt)   1220  ATGAGTTTTT CTAATCAGAA TTGGTTAATT GGTTGTAACA CTGGCAGAGC ATTACGCTGA
kan(mu)
ORF              D  E  F  F kan(wt)   1160  CTTGACGGGA CGGCGCAAGC TCATGACCAA AATCCCTTAA CGTGAGTTTT CGTTCCACTG
kan(nu)               AC    AA  AC kan(wt)   1100  AGCGTCAGAC CCCGTAGAAA AGATCAAAGG ATCTTCTTGA GATCCTTTTT TTCTGCGCGT kan(wt)   1040  AATCTGCTGC TTGCAAACAA AAAAACCACC GCTACCAGCG GTGGTTTGTT TGCCGGATCA kan(wt)    980  AGAGCTACCA ACTCTTTTTC CGAAGGTAAC TGGCTTCAGC AGAGCGCAGA TACCAAATAC kan(wt)    920  TGTTCTTCTA GTGTAGCCGT AGTTAGGCCA CCACTTCAAG AACTCTGTAG CACCGCCTAC kan(wt)    860  ATACCTCGCT CTGCTAATCC TGTTACCAGT GGCTGCTGCC
```

Note:
Mutated nucleotides are underlined. The *AlwN*i and *Eco*O1091 sites are indicated in bold type. The nucleotide numbering scheme is the same as the backbone vector pUK21.

TABLE 3

Plasmids containing immunostimulatory CpG motifs

| Plasmid | Backbone | No. CpG, Motifs | Species Specificity and ODN Equivalence of CpG-S Insert |
|---|---|---|---|
| pMCG-16 | pMAS | 16 | mouse-specific CpG motif #1826[1] |
| pMCG-50 | pMAS | 50 | |
| pMCG-100 | pMAS | 100 | |
| pMCG-200 | pMAS | 200 | |
| pHCG-30 | pMAS | 30 | human-specific CpG motif – no ODN equivalent[2] |
| pHCG-50 | pMAS | 50 | |
| pHCG-100 | pMAS | 100 | |
| pHCG-200 | pMAS | 200 | |
| pHIS-40 | pMAS | 40 | human-specific CpG motif #2006[3] |
| pHIS-64 | pMAS | 64 | |
| pHIS-128 | pMAS | 128 | |
| pHIS-192 | pMAS | 192 | |

[1] sequence of 1826 is TCCATGA<u>CG</u>TTCCTGA<u>CG</u>TT
[2] sequence used as a source of CpG motifs is GACTT<u>CG</u>TGT<u>CG</u>TTCTTCTGT<u>CG</u>TCTTTAG<u>CG</u>CTTCTCCTG<u>CG</u>TG<u>CG</u>TCCCTTG(SEQ ID NO:14)
[3] sequence of 2006 is T<u>CG</u>T<u>CG</u>TTTTGT<u>CG</u>TTTTGT<u>CG</u>TT(SEQ ID NO:3)

TABLE 4

Plasmids encoding hepatitis B surface antigen
(derived from ayw or adw subtypes of HBV)

| Plasmid | Backbone | Insert |
| --- | --- | --- |
| pUK-S | pUK21-A2 | HBV-S (ayw) |
| pUKAX-S | pUK21-AX* | HBV-S (ayw) |
| pMAS-S | pMAS | HBV-S (ayw) |
| pMCG16-S | pMCG-16 | HBV-S (ayw) |
| pMCG50-S | pMCG-50 | HBV-S (ayw) |
| pMCG100-S | pMCG-100 | HBV-S (ayw) |
| pMCG200-S | pMCG-200 | HBV-S (ayw) |
| pHCG30-S | pHCG-30 | HBV-S (ayw) |
| pHCG50-S | pHCG-50 | HBV-S (ayw) |
| pHCG100-S | pHCG-100 | HBV-S (ayw) |
| pHCG200-S | pHCG-200 | HBV-S (ayw) |
| pHIS40-S(ad) | pHIS-40 | HBV-S (adw2) |
| pHIS64-S(ad) | pHIS-64 | HBV-S (adw2) |
| pHIS128-S(ad) | pHIS-128 | HBV-S (adw2) |
| pHIS192-S(ad) | pHIS-192 | HBV-S (adw2) |

*pUK21-AX was created by deleting f1 origin from pUK21-A

TABLE 5

Sequence comparison of pUK21-A2 (SEQ ID NO:83) and pGT.
75 point-mutations (indicated with *) in pUK21-A2
results in the gene therapy vector (pGT)(SEQ ID NO:84)

```
pUK21-A2(1)    GAATTCGAGC TCCCGGGTAC CATGGCATGC ATCGATAGAT CTCGAGTCTA GACTAGAGCT
pGT            GAATTCGAGC TCCCGGGTAC CATGGCATGC ATCGATAGAT CTCGAGTCTA GACTAGAGCT
               ---------- ---------- ---------- ---------- ---------- ---------- pUK21-A2(61)   CGCTGATCAG CCTCGACTGT GCCTTCTAGT TGCCAGCCAT CTGTTGTTTG CCCCTCCCCC
PGT            CGCTGATCAG CCTCGACTGT GCCTTCTAGT TGCCAGCCAT CTGTTGTTTG CCCCTCCCCC
               ---------- ---------- ---------- ---------- ---------- ----------

PUK21-A2(121)  GTGCCTTCCT TGACCCTGGA AGGTGCCACT CCCACTGTCC TTTCCTAATA AAATGAGGAA
pGT            GTGCCTTCCT TGACCCTGGA AGGTGCCACT CCCACTGTCC TTTCCTAATA AAATGAGGAA
               ---------- ---------- ---------- ---------- ---------- ----------

PUK21-A2(181)  ATTGCATCGC ATTGTCTGAG TAGGTGTCAT TCTATTCTGG GGGGTGGGGT GGGGCAGGAC
pGT            ATTGCATCGC ATTGTCTGAG TAGGTGTCAT TCTATTCTGG GGGGTGGGGT GGGGCAGGAC
               ---------- ---------- ---------- ---------- ---------- ---------- pUK21-A2(241)  AGCAAGGGGG AGGATTGGGA AGACAATAGC AGGCATGCTG GGGAAGGCCT CGGACTAGTG
pGT            AGCAAGGGGG AGGATTGGGA AGACAATAGC AGGCATGCTG GGGAAGGCCT CGGACTAGTG
               ---------- ---------- ---------- ---------- ---------- ---------- pUK21-A2(301)  GCGTAATCAT GGTCATAGCT GTTTCCTGTG TGAAATTGTT ATCCGCTCAC AATTCCACAC
PGT            CCGGAATCAT GGTCATAGCT GTTTCCTGTG TGAAATTGTT ATCCGCTCAC AATTCCACAC
               *--*------ ---------- ---------- ---------- ---------- ---------- pUK21-A2(361)  AACATACGAG CCGCGAAGC ATAAAGTGTA AAGCCTGGGG TGCCTAATGA GTGAGCTAAC
pGT            AACATCCGGG CCGCGAAGC ATAAAGTGTA AAGCCTGGGG TGCCTAATGA GTGAGCTAAC
               -----*--*- ---------- ---------- ---------- ---------- ---------- pUK21-A2(421)  TCACATTAAT TGCGTTGCGC TCACTGCCCG CTTTCCAGTC GGGAAACCTG TCGTGCCAGC
pGT            TCACATTAAT TCCGTTCCGC TCACTGCCCG CTTTCCAGTC GGGAAACCTG CCGTGCCAGC
               ---------- -*----*--- ---------- ---------- ---------- *--------- pUK21-A2(481)  TGCATTAATG AATCGGCCAA CGCGCGGGGA GAGGCGGTTT GCGTATTGGG CGCTCTTCCG
PGT            TGCATTAATG AATCGGCCAA CGCGCGGGGA GAGCCGGTTT CCGTATTGGC CGCTCTTCCG
               ---------- ---------- ---------- ---*------ *--------* ---------- pUK21-A2(541)  CTTCCTCGCT CACTGACTCG CTGCGCTCGG TCGTTCGGCT GCGGCGAGCG GTATCAGCTC
pGT            CTTCCTCGCT CACTGACTCG CTGCGCTCGG TCGTTCGGCT GCGGCGAGCG GTATCAGCTC
               ---------- ---------- ---------- ---------- ---------- ----------

PUK21-A2(601)  ACTCAAAGGC GGTAATACGG TTATCCACAG AATCAGGGGA TAACGCAGGA AAGAACATGT
pGT            ACTCAAAGGC GGTAATACGG TTATCCACAG AATCAGGGGA TAACGCAGGA AAGAACATGT
               ---------- ---------- ---------- ---------- ---------- ---------- pUK21-A2(661)  GAGCAAAAGG CCAGCAAAAG GCCAGGAACC GTAAAAAGGC CGCGTTGCTG GCGTTTTTCC
pGT            GAGCAAAAGG CCAGCAAAAG GCCAGGAACC GTAAAAAGGC CGCGTTGCTG GCGTTTTTCC
               ---------- ---------- ---------- ---------- ---------- ---------- pUK21-A2(721)  ATAGGCTCCG CCCCCCTGAC GAGCATCACA AAAATCGACG CTCAAGTCAG AGGTGGCGAA
pGT            ATAGGCTCCG CCCCCCTGAC GAGCATCACA AAAATCGACG CTCAAGTCAG AGGTGGCGAA
               ---------- ---------- ---------- ---------- ---------- ----------
```

TABLE 5-continued

Sequence comparison of pUK21-A2 (SEQ ID NO:83) and pGT.
75 point-mutations (indicated with *) in pUK21-A2
results in the gene therapy vector (pGT)(SEQ ID NO:84)

```
pUK21-A2(781)  ACCCGACAGG ACTATAAAGA TACCAGGCGT TTCCCCCTGG AAGCTCCCTC GTGCGCTCTC
pGT            ACCCGACAGG ACTATAAAGA TACCAGGCGT TTCCCCCTGG AAGCTCCCTC GTGCGCTCTC
               ---------- ---------- ---------- ---------- ---------- ---------- pUK21-A2(841)  CTGTTCCGAC CCTGCCGCTT ACCGGATACC TGTCCGCCTT TCTCCCTTCG GGAAGCGTGG
pGT            CTGTTCCGAC CCTGCCGCTT ACCGGATACC TGTCCGCCTT TCTCCCTTCG GGAAGCGTGG
               ---------- ---------- ---------- ---------- ---------- ---------- pUK21-A2(901)  CGCTTTCTCA TAGCTCACGC TGTAGGTATC TCAGTTCGGT GTAGGTCGTT CGCTCCAAGC
pGT            CGCTTTCTCA TAGCTCACGC TGTAGGTATC TCAGTTCGGT GTAGGTCGTT CGCTCCAAGC
               ---------- ---------- ---------- ---------- ---------- ---------- pUK21-A2(961)  TGGGCTGTGT GCACGAACCC CCCGTTCAGC CCGACCGCTG CGCCTTATCC GGTAACTATC
pGT            TGGGCTGTGT GCACGAACCC CCCGTTCAGC CCGACCGCTG CGCCTTATCC GGTAACTATC
               ---------- ---------- ---------- ---------- ---------- ---------- pUK21-A2(1021) GTCTTGAGTC CAACCCGGTA AGACACGACT TATCGCCACT GGCAGCAGCC ACTGGTAACA
pGT            TGGGCTGTGT GCACGAACCC CCCGTTCAGC CCGACCGCTG CGCCTTATCC GGTAACTATC
               ---------- ---------- ---------- ---------- ---------- ---------- pUK21-A2(1081) GGATTAGCAG AGCGAGGTAT GTAGGCGGTG CTACAGAGTT CTTGAAGTGG TGGCCTAACT
PGT            GGATTAGCAG AGCGAGGTAT GTAGGCGGTG CTACAGAGTT CTTGAAGTGG TGGCCTAACT
               ---------- ---------- ---------- ---------- ---------- ---------- pUK21-A2(1141) ACGGCTACAC TAGAAGAACA GTATTTGGTA TCTGCGCTCT GCTGAAGCCA GTTACCTTCG
PGT            ACGGCTACAC TAGAAGAACA GTATTTGGTA TCTGCGCTCT GCTGAAGCCA GTTACCTTCG
               ---------- ---------- ---------- ---------- ---------- ---------- pUK21-A2(1201) GAAAAAGAGT TGGTAGCTCT TGATCCGGCA AACAAACCAC CGCTGGTAGC GGTGGTTTTT
pGT            GAAAAAGAGT TGGTAGCTCT TGATCCGGCA AACAAACCAC CGCTGGTAGC GGTGGTTTTT
               ---------- ---------- ---------- ---------- ---------- ---------- pUK21-A2(1261) GAAAAAGAGT TGGTAGCTCT TGATCCGGCA AACAAACCAC CGCTGGTAGC GGTGGTTTTT
pGT            GAAAAAGAGT TGGTAGCTCT TGATCCGGCA AACAAACCAC CGCTGGTAGC GGTGGTTTTT
               ---------- ---------- ---------- ---------- ---------- ---------- pUK21-A2(1321) TTTCTACGGG GTCTGACGCT CAGTGGAACG AAAACTCACG TTAAGGGATT TTGGTCATGA
pGT            TTTCTACGGG GTCTGACGCT CAGTGGAACG AAAACTCACG TTAAGGGATT TTGGTCATGA
               ---------- ---------- ---------- ---------- ---------- ---------- pUK21-A2(1381) GCTTGCGCCG TCCCGTCAAG TCAGCGTAAT GCTCTGCCAG TGTTACAACC AATTAACCAA
pGT            GCTTGCGCCG TCCCGTCAAG TCACCGGAAT GCTCTGCCAG TGTTACAACC AATTAACCAA
               ---------- ---------- ---*--*--- ---------- ---------- ---------- pUK21-A2(1441) TTCTGATTAG AAAAACTCAT CGAGCATCAA ATGAAACTGC AATTTATTCA TATCAGGATT
pGT            TTCTGATTAG AAAAACTCAT CCAGCATCAA ATGAAACTGC AATTTATTCA TATCAGGATT
               ---------- ---------- -*-------- ---------- ---------- ---------- pUK21-A2(1501) ATCAATACCA TATTTTTGAA AAAGCCGTTT CTGTAATGAA GGAGAAAACT CACCGAGGCA
pGT            ATCAATACCA TATTTTTGAA AAAGCCGTTT CTGTAATGAA GGAGAAAACT CACCGAGGCA
               ---------- ---------- ---------- ---------- ---------- ---------- pUK21-A2(1561) GTTCCATAGG ATGGCAAGAT CCTGGTATCG GTCTGCGATT CCGACTCGTC AACATCAAT
pGT            GTTCCATAGG ATGGCAAGAT CCTGGTATCG GTCTGCAATT CCGACTCGGC AACATCAAT
               ---------- ---------- ---------- ------*--- ---------*- ---------- pUK21-A2(1621) ACAACCTATT AATTTCCCCT CGTCAAAAAT AAGGTTATCA AGTGAGAAAT CACCATGAGT
pGT            ACAACCTATT AATTTCCCCT CATCAAAAAT AAGGTTATCA AGTGAGAAAT CACCATGAGT
               ---------- ---------- -*-------- ---------- ---------- ---------- pUK21-A2(1681) GACGACTGAA TCCGGTGAGA ATGGCAAAAG TTTATGCATT TCTTTCCAGA CTTGTTCAAC
pGT            AACTACTGAA TCCGGTGAGA ATGGCAAAAG TTTATGCATT TCTTTCCAGA CTTGTTCAAC
               *--*------ ---------- ---------- ---------- ---------- ---------- pUK21-A2(1741) AGGCCAGCCA TTACGCTCGT CATCAAAATC ACTCGCATCA ACCAAACCGT TATTCATTCG
pGT            AGGCCAGCCA TTACGCTCAT CATCAAAATC GGAAGCATCA ACCAAACCGT TATTCATTCG
               ---------- ---------*- ---------- ****------ ---------- ---------- pUK21-A2(1801) TGATTGCGCC TGAGCGAGAC GAAATACGCG ATCGCTGTTA AAAGGACAAT TACAAACAGG
pGT            GGATTGAGCC TGAGCCAGAC GGAATACGCG GTCGCTGTTA AAAGGACAAT TACAAACAGG
               *------*--- -----*---- -*-------- *--------- ---------- ---------- pUK21-A2(1861) AATCGAATGC AACCGGCGCA GGAACACTGC CAGCGCATCA ACAATATTTT CACCTGAATC
pGT            AATGGAATGC AACCGGCGGA GGAACACTGC CAGAGCATCA ACAATATTTT CACCTGAATC
               ---*------ ---------*- ---------- ---*------ ---------- ----------
```

TABLE 5-continued

Sequence comparison of pUK21-A2 (SEQ ID NO:83) and pGT.
75 point-mutations (indicated with *) in pUK21-A2
results in the gene therapy vector (pGT)(SEQ ID NO:84)

```
pUK21-A2(1921) AGGATATTCT TCTAATACCT GGAATGCTGT TTTTCCGGGG ATCGCAGTGG TGAGTAACCA
pGT            AGGATATTCT TCTAATACCT GGAATGCTGT TTTTCCGGGG ATAGCAGTGG TGAGTAACCA
               ---------- ---------- ---------- ---------- ---------- ---------- pUK21-A2(1981) TGCATCATCA GGAGTACGGA TAAAATGCTT GATGGTCGGA AGAGGCATAA ATTCCGTCAG
pGT            TGCATCATCA GGAGTACGGA TAAAATGCTT GATGGTCGGA AGAGGCATAA ATTCCGTCAG
               ---------- ---------- ---------- ---------- ---------- ---------- pUK21-A2(2041) CCAGTTTAGT CTGACCATCT CATCTGTAAC ATCATTGGCA ACGCTACCTT TGCCATGTTT
pGT            CCAGTTTAGT CTGACCATCT CATCTGTAAC ATCATTGGCA ACGCTACCTT TGCCATGTTT
               ---------- ---------- ---------- ---------- ---------- ---------- pUK21-A2(2101) CAGAAACAAC TCTGGCGCAT CGGGCTTCCC ATACAAGCGA TAGATTGTCG CACCTGATTG
pGT            CAGAAACAAC TCCGGCGCGT CGGGCTTCCC ATACAAGCGG TAGATTGTAG CACCTGATTG
               ---------- ---*-----*- ---------- ---------* ---------*- ---------- pUK21-A2(2161) CCCGACATTA TCGCGAGCCC ATTTATACCC ATATAAATCA GCATCCATGT TGGAATTTAA
pGT            CCCGACATTA TCGCGAGCCC ATTTATACCC ATATAAATCA GCATCCATGT TGGAATTTAA
               ---------- ---------- ---------- ---------- ---------- ---------- pUK21-A2(2221) TCGCGGCCTC GACGTTTCCC GTTGAATATG GCTCATAACA CCCCTTGTAT TACTGTTTAT
pGT            TCGCGGCCTG GAGGTTTCCC GTTGAATATG GCTCATAACA CCCCTTGTAT TACTGTTTAT
               ---------* --*------- ---------- ---------- ---------- ---------- pUK21-A2(2281) GTAAGCAGAC AGTTTTATTG TTCATGATGA TATATTTTTA TCTTGTGCAA TGTAACATCA
pGT            GTAAGCAGAC AGTTTTATTG TTCATGATGA TATATTTTTA TCTTGTGCAA TGTAACATCA
               ---------- ---------- ---------- ---------- ---------- ---------- pUK21-A2(2341) GAGATTTTGA GACACAACGT GGCTTTCCCC CCCCCCCCCA TGACATTAAC CTATAAAAAT
pGT            GAGATTTTGA GACACACCGG GGCTTTCCCC CCCCCCCCCA TGACATTAAC CTATAAAAAT
               ---------- ------*--* ---------- ---------- ---------- ---------- pUK21-A2(2401) AGGCGTATCA CGAGGCCCTT TCGTCTCGCG CGTTTCGGTG ATGACGGTGA AAACCTCTGA
pGT            AGCCGTATCC CGAGGCCCTT CCGTCTCGCG CGTTCCGGTG ATGCCGGTGA AAACCTCTGA
               --*------* ---------* *--------- ----*----- ---*------ ---------- pUK21-A2(2461) CACATGCAGC TCCCGGAGAC GGTCACAGCT TGTCTGTAAG CGGATGCCGG GAGCAGACAA
pGT            CACATGCAGC TCCCGGAGAC GGTCACAGCT TGTCTGTAAG CGGATGCCGG GAGCAGACAA
               ---------- ---------- ---------- ---------- ---------- ---------- pUK21-A2(2521) GCCCGTCAGG GCGCGTCAGC GGGTGTTGGC GGGTGTCGGG GCTGGCTTAA CTATGCGGCA
pGT            GCCCGTCAGG GCGCGTCAGC GGGTGTTGGC GGGTGTCGGG GCTGGCTTAA CTATGCGGCA
               ---------- ---------- ---------- ---------- ---------- ---------- pUK21-A2(2581) TCAGAGCAGA TTGTACTGAG AGTGCACCAT AAAATTGTAA ACGTTAATAT TTTGTTAAAA
pGT            TCAGAGCAGA TTGTACTGAG AGTGCACCAT AAAATTGTAA CCGTTAATAT TTTGTTAAAA
               ---------- ---------- ---------- ---------- *--------- ---------- pUK21-A2(2641) TTCGCGTTAA ATTTTTGTTA AATCAGCTCA TTTTTTAACC AATAGACCGA AATCGGCAAA
pGT            TTCGCGTTAA ATTTTTGTTA AATCAGCTCA TTTTTTAACC AATAGACCGA AATCGGCAAA
               ---------- ---------- ---------- ---------- ---------- ---------- pUK21-A2(2701) ATCCCTTATA AATCAAAAGA ATAGCCCGAG ATAGAGTTGA GTGTTGTTCC AGTTTGGAAC
pGT            ATCCCTTATA AATCAAAAGA ATAGCCCGAG ATAGAGTTGA GTGTTGTTCC AGTTTGGAAC
               ---------- ---------- ---------- ---------- ---------- ---------- pUK21-A2(2761) AAGAGTCCAC TATTAAAGAA CGTGGACTCC AACGTCAAAG GGCGAAAAAC CGTCTATCAG
pGT            AAGAGTCCAC TATTAAAGAC CGTGGACTCC ACCGTCAAAG GCGAAAAAC CGTCTATCAG
               ---------- ---------* ---------- -*-------- -*-------- ---------- pUK21-A2(2821) GGCGATGGCC CACCCCGATT TAGAGCTTGA CGGGGAAAGC CGGCGAACGT GGCGAGAAAG
pGT            GCCGATGGCC CACCCCGATT TAGAGCTTGA CGGGGAAAGC CGGCGCGCGT GGCGAGAAAG
               -*-------- ---------- ---------- ---------- -----**--- ---------- pUK21-A2(2881) GAAGGGAAGA AAGCGAAAGG AGCGGGCGCT AAGGCGCTGG CAAGTGTAGC GGTCACGCTG
pGT            GAAGGGAAGA AACCGAAAGG AGCGGCCGCT AAGCCGCTGG CAAGTGTAGC GGTCCCGCTG
               ---------- --*------- -----*---- ---*------ ---------- ----*----- pUK21-A2(2941) CGCGTAACCA CCACACCCGC CGCGCTTAAT GCGCCGCTAC AGGGCGCGTA CTATGGTTGC
pGT            CGCGTAACCA CCACACCCGC CGCGCTTAAT CCGCCGCTAC AGGGCGCGTA CTATGGTTGC
               ---------- ---------- ---------- *--------- ---------- ---------- pUK21-A2(3001) TTTGACGTAT GCGGTGTGAA ATACCGCACA GATGCGTAAG GAGAAAATAC CGCATCAGGC
pGT            TTTGCCGTAT GCGGTGTGAA ATACCGCACA GATCCGTAAG GAGAAAATAC CGCATCAGCC
```

TABLE 5-continued

Sequence comparison of pUK21-A2 (SEQ ID NO:83) and pGT.
75 point-mutations (indicated with *) in pUK21-A2
results in the gene therapy vector (pGT)(SEQ ID NO:84)

```
              ----*----- ---------- ---------- ---*------ ---------- ---------*-
pUK21-A2(3061) GCCATTCGCC ATTCAGGCTG CGCAACTGTT GGGAAGGGCG ATCGGTGCGG GCCTCTTCGC
pGT            GCCATCCGCC ATTCAGGCTC CGCAACTGTT GGGAAGGCCG ATCGGTGCGG GCCTCTCCGC
              -----*---- ---------* ---------- --------*-- ---------- ------*--- pUK21-A2(3121) TATTACGCCA GCTGGCGAAA GGGGGATGTG CTGCAAGGCG ATTAAGTTGG GTAACGCCAG
pGT            TATTCCGCCA GCTGCCGAAA GGGGGATGTG CTGCAAGCCG ATTAAGTTGG GTACCGCCAG
              ----*----- ----*----- ---------- --------*-- ---------- ---*------ pUK21-A2(3181) GGTTTTCCCA GTCACGACGT TGTAAAACGA CGGCCAGTGA ATTGTAATAC GACTCACTAT
pGT            GGTTTTCCCA GTCACGGCGG TGTAAACCGA CGGCCAGTGA ATTGTAATCC GACTCACTAT
              ---------- ------*--* ------*--- ---------- --------*- ---------- pUK21-A2(3241) AGGGCGAATT GGGGATCGAT CCACTAGTTC TAGATCCGAT GTACGGGCCA GATATACGCG
pGT            AGGCCGAATT GGGGACCGAT CCACTAGTTC TAGATCCGAT GTACGGGCCA GATATACGCG
              ---*------ -----*---- ---------- ---------- ---------- ---------- pUK21-A2(3301) TTGACATTGA TTATTGACTA GTTATTAATA GTAATCAATT ACGGGGTCAT TAGTTCATAG
pGT            TTGACATTGA TTATTGACTA GTTATTAATA GTAATCAATT ACGGGGTCAT TAGTTCATAG
              ---------- ---------- ---------- ---------- ---------- ---------- pUK21-A2(3361) TTGACATTGA TTATTGACTA GTTATTAATA GTAATCAATT ACGGGGTCAT TAGTTCATAG
pGT            TTGACATTGA TTATTGACTA GTTATTAATA GTAATCAATT ACGGGGTCAT TAGTTCATAG
              ---------- ---------- ---------- ---------- ---------- ---------- pUK21-A2(3421) CAACGACCCC CGCCCATTGA CGTCAATAAT GACGTATGTT CCCATAGTAA CGCCAATAGG
pGT            CAACGACCCC CGCCCATTGA CGTCAATAAT GACGTATGTT CCCATAGTAA CGCCAATAGG
              ---------- ---------- ---------- ---------- ---------- ---------- pUK21-A2(3481) GACTTTCCAT TGACGTCAAT GGGTGGAGTA TTTACGGTAA ACTGCCCACT TGGCAGTACA
pGT            GACTTTCCAT TGACGTCAAT GGGTGGAGTA TTTACGGTAA ACTGCCCACT TGGCAGTACA
              ---------- ---------- ---------- ---------- ---------- ---------- pUK21-A2(3541) TCAAGTGTAT CATATGCCAA GTACGCCCCC TATTGACGTC AATGACGGTA AATGGCCCGC
pGT            TCAAGTGTAT CATATGCCAA GTACGCCCCC TATTGACGTC AATGACGGTA AATGGCCCGC
              ---------- ---------- ---------- ---------- ---------- ---------- pUK21-A2(3601) CTGGCATTAT GCCCAGTACA TGACCTTATG GGACTTTCCT ACTTGGCAGT ACATCTACGT
pGT            CTGGCATTAT GCCCAGTACA TGACCTTATG GGACTTTCCT ACTTGGCAGT ACATCTACGT
              ---------- ---------- ---------- ---------- ---------- ---------- pUK21-A2(3661) ATTAGTCATC GCTATTACCA TGGTGATGCG GTTTTGGCAG TACATCAATG GGCGTGGATA
pGT            ATTAGTCATC GCTATTACCA TGGTGATGCG GTTTTGGCAG TACATCAATG GGCGTGGATA
              ---------- ---------- ---------- ---------- ---------- ---------- pUK21-A2(3721) GCGGTTTGAC TCACGGGGAT TTCCAAGTCT CCACCCCATT GACGTCAATG GGAGTTTGTT
pGT            GCGGTTTGAC TCACGGGGAT TTCCAAGTCT CCACCCCATT GACGTCAATG GGAGTTTGTT
              ---------- ---------- ---------- ---------- ---------- ---------- pUK21-A2(3781) TTGGCACCAA AATCAACGGG ACTTTCCAAA ATGTCGTAAC AACTCCGCCC CATTGACGCA
pGT            TTGGCACCAA AATCAACGGG ACTTTCCAAA ATGTCGTAAC AACTCCGCCC CATTGACGCA
              ---------- ---------- ---------- ---------- ---------- ---------- pUK21-A2(3841) AATGGGCGGT AGGCGTGTAC GGTGGGAGGT CTATATAAGC AGAGCTCTCT GGCTAACTAG
pGT            AATGGGCGGT AGGCGTGTAC GGTGGGAGGT CTATATAAGC AGAGCTCTCT GGCTAACTAG
              ---------- ---------- ---------- ---------- ---------- ---------- pUK21-A2(3901) AGAACCCACT GCTTACTGGC TTATCGAAAT TGCGGCCGCC ACGGCGATAT CGGATCCATA
pGT            AGAACCCACT GCTTACTGGC TTATCGAAAT TGCGGCCGCC ACGGCGATAT CGGATCCATA
              ---------- ---------- ---------- ---------- ---------- ---------- pUK21-A2(3961) TGACGTCGAC GCGTCTGCAG AAGCTTC
pGT            TGACGTCGAC GCGTCTGCAG AAGCTTC
              ---------- ---------- -------
```

TABLE 6

ODN used with plasmid DNA

| Backbone | ODN code number | Sequence | |
|---|---|---|---|
| S-ODN | 1826 | TCCATGACGTTCCTGACGTT | (SEQ ID NO:51) |
| | 1628 | GGGGTCAACGTTGAGGGGGG | (SEQ ID NO:52) |
| | 1911 | TCCAGGACTTTCCTCAGGTT | (SEQ ID NO:53) |
| | 1982 | TCCAGGACTTCTCTCAGGTT | (SEQ ID NO:54) |
| | 2017 | CCCCCCCCCCCCCCCCCCCC | (SEQ ID NO:55) |
| O-ODN | 2061 | TCCATGACGTTCCTGACGTT | (SEQ ID NO:56) |
| | 2001 | GGCGGCGGCGGCGGCGGCGG | (SEQ ID NO:57) |
| SOS-ODN | 1980 | TCCATGACGTTCCTGACGTT | (SEQ ID NO:58) |
| | 1585 | GGGTCAACGTTGAGGGGG | (SEQ ID NO:59) |
| | 1844 | TCTCCCAGCGTGCGCCATAT | (SEQ ID NO:60) |
| | 1972 | GGGGTCTGTGCTTTTGGGGGG | (SEQ ID NO:61) |
| | 2042 | TCAGGGGTGGGGGAACCTT | (SEQ ID NO:62) |
| | 1981 | GGGGTTGACGTTTTGGGGGG | (SEQ ID NO:63) |
| | 2018 | TCTAGCGTTTTTAGCGTTCC | (SEQ ID NO:64) |
| | 2021 | TCGTCGTTGTCGTTGTCGTT | (SEQ ID NO:65) |
| | 2022 | TCGTCGTTTTGTCGTTTTGTCGTT | (SEQ ID NO:66) |
| | 2023 | TCGTCGTTGTCGTTTTGTCGTT | (SEQ ID NO:67) |

Note: (SEQ ID NO: 51–67, respectively)

SOS-ODN had two S-linkages at the 5' end, five S-linkages at the 3' end, and O-linkages in between.

Three ODN used in this study were of the same murine-specific immunostimulatoxy sequence in three different backbones (1826, 2061 and 1980).

All ODN were synthesized by Hybridon (Milford, Mass.) or Operon (Alameda, Calif.). ODN were ethanol precipitated and resuspended in saline prior to use alone or as an additive to the plasmid DNA solution.

TABLE 7

Genomic frequencies of selected hexamers
Genomic frequency ($\times 10^{-3}$)

| hexamer: | Adenovirus Type 2 | Adenovirus Type 12 | E. coli | Human |
|---|---|---|---|---|
| GCGCGC | 1.614 | 0.498 | 0.462 | 0.153 |
| GCGGCG | 1.530 | 0.469 | 0.745 | 0.285 |
| GGCGGC | 1.419 | 0.440 | 0.674 | 0.388 |
| CGCGCG | 1.336 | 0.322 | 0.379 | 0.106 |
| GCCGCC | 1.280 | 0.410 | 0.466 | 0.377 |
| CGCCGC | 1.252 | 0.410 | 0.623 | 0.274 |
| GACGTT | 0.083 | 0.234 | 0.263 | 0.068 |
| AACGTT | 0.056 | 0.205 | 0.347 | 0.056 |
| (CpG-S) | | | | |

The frequencies of hexamers in adenoviral and E. coli genomes were kindly provided by J. Han (University of Alabama, Birmingham), who also determined those for the human genome[52]. The hexamer frequencies in type 5 adenovirus are essentially identical to those in type 2, and are therefore not shown. The last two hexamers are CpG-S motifs shown for comparison and are the most stimulatory of all tested CpG-S motifs.

Note that the expected frequency of a randomly selected hexamer is $1/4096 = 0.244 \times 10^{-3}$.

TABLE 8

Genomic DNA from type 12 but not type 2 adenovirus stimulates cytokine secretion from human PBMC

| | Experiment 1[1] | | Experiment 2[1] | |
|---|---|---|---|---|
| | TNF-α | IL-6 | TNF-α | IL-6 |
| Cells | 27 | 800 | 30 | 800 |
| EC 3 µg/ml | 235 | 26,500 | 563 | 34,000 |
| CT 10 µg/ml | 0 | 1,400 | 0 | 2,800 |
| Adv 2;3 µg/ml | 15.6 | 900 | 30 | 1,900 |
| Adv 12;3 µg/ml | 86 | 11,300 | 120 | 11,250 |

[1]PBMC were obtained from normal human donors and cultured at $1 \times 10^5$ cells/200 µl in RPMI with 10% autologous serum for 4 hr (TNF-α assay) or 24 hr (IL-6 assay). The level of cytokine present in culture supernatants was determined by ELISA (pg/ml).
Adv = adenovirus serotype

TABLE 9

Adenoviral type 5 DNA suppresses the cytokine response to EC DNA by human PBMC

| DNA Source | IL-6 (pg/ml)[1] | IFN-(pg/ml)[1] | TNF-(pg/ml)[1] |
|---|---|---|---|
| EC DNA(50 µg/ml) | >3000 | 700 | 700 |
| EC DNA(5 µg/ml) | >3000 | 400 | 675 |
| EC DNA(0.5 µg/ml) | >3000 | 200 | 350 |
| EC DNA(0.05 µg/ml) | 3000 | ND | 100 |
| Adenoviral DNA (50 µg/ml) | 2500 | 0 | 0 |
| Adenoviral DNA (5 µg/ml) | 1500 | 0 | 0 |
| EC:Adeno DNA(50:50 µg/ml) | 2000 | 35 | 675 |
| EC:Adeno DNA (5:5 µg/ml) | 1500 | 40 | ND |

[1]Represents the level of cytokine production above that in wells cultured with cells alone without any DNA. Levels of cytokines were determined by ELISA using Quantikine kits from R & D Systems.
ND = not done

TABLE 10

Inhibitory CpG motifs can block B cell proliferation induced by a stimulatory CpG motif

| Oligonucleotide added | cpm |
|---|---|
| medium | 194 |
| 1668 (TCCATGACGTTCCTGATGCT)(SEQ ID NO:68) | 34,669 |
| 1668 + 1735 (GCGTTTTTTTTTGCG)(SEQ ID NO:69) | 24,452 |
| 1720 (TCCATGAGCTTCCTGATGCT)(SEQ ID NO:70) | 601 |
| 1720 + 1735 | 1109 |

Splenic B cells from a DBA/2 mouse were cultured at $5 \times 10^4$ cells/100 µl well in 96 well microtiter plates in RPMI as previously described (Krieg, et al., 1995) with or without the indicated phosphorothioate modified oligonucleotides at a concentration of 60 ng/ml for 48 hr. The cells were then pulsed with $^3$H thymidine, harvested, and the cpm determined by scintillation counting. The stimulatory CpG oligo 1668 was slightly but significantly inhibited by the inhibitory motifs in oligo 1735. The non CpG oligo 1720 is included as a negative control. (SEQ ID NO:68–70, respectively).

TABLE 11

Inhibitory effects of "bad" CpG motifs on the "good" CpG Oligo 1619

| Oligonucleotide added | IL-12 in pg/ml |
|---|---|
| medium | 0 |
| 1619 alone | 6 |
| 1619 + 1949 (TCCATGTCGTTCCTGATGCG(SEQ ID NO:72)) | 16 |
| 1619 + 1952 (TCCATGTCGTTCCGCGCGCG(SEQ ID NO:73)) | 0 |
| 1619 + 1953 (TCCATGTCGTTCCTGCCGCT(SEQ ID NO:74)) | 0 |
| 1619 + 1955 (GCGGCGGGCGGCGCGCGCCC(SEQ ID NO:75)) | 0 |

Notes:
The sequence of oligo 1619 is TCCATGTCGTTCCTGATGCT (SEQ ID NO:71)
1949 has only 1 GCG at the 3' end, which has essentially no inhibitory activity Human PBMC were cultured in 96 well microtiter plates at $10^5/200$ µl for 24 hr in RPMI containing 10% autologous serum. Supernatants were collected at the end of the culture and tested for IL-12 by ELISA. All wells except the control (medium) contained 60 µg/ml of the stimulatory CpG oligodeoxynucleotide 1619; stimulatory (1949) and inhibitory (all other sequences have a strong inhibitory motif) oligos were added to the indicated wells at the same concentration at the beginning of culture. All oligos have unmodified backbones.

TABLE 12

Effect of CpG-S ODN adjuvant on anti-HBs response in mice immunized with HBsAg-expressing DNA vaccine (pCMV-S): comparison of mixed formulation with temporal or spatial separation of plasmid DNA and ODN

| CpG ODN (100 µg) | | Site and Time Relative DNA vaccine | Anti-HBs Titer |
|---|---|---|---|
| Sequence | Backbone | (pCMV-S, 10 µg) | at 12 wk |
| None | — | — | 6379 ± 2126 |
| 1826O | O-ODN | Mixed together (same time, same muscle) | 4395 ± 1390 |

TABLE 13

Identification of neutralizing CpG motifs which reduce the induction of cytokine secretion by a CpG-S motif in the same ODN (cis-neutralization)

| ODN | sequence 5'-3'[1] | | ODN-induced cytokine expression[2] | | |
|---|---|---|---|---|---|
| | | | IL-6[2] | IL-12 | IFN-γ |
| None | | | <5 | 206 | 898 |
| 1619 | TCCATGTCGTTCCTGATGCT | (SEQ ID NO:71) | 1405 | 3130 | 4628 |
| 1952 | ............GCGCGCG | (SEQ ID NO:73) | 559 | 1615 | 2135 |
| 1953 | ...............CC... | (SEQ ID NO:74) | 557 | 1854 | 2000 |

[1]Dots in the sequence of ODN 1952 and 1953 indicate identity to ODN 1619; CpG dinucleotides are underlined for clarity. ODN without CpG-N or CpG-S motifs had little or no effect on cytokine production. The data shown are representative of 4 experiments.
[2]All cytokines are given in pg/ml; measured by ELISA on supernatants from DBA/2 spleen cells cultured in 96 well plates at $2 \times 10^7$ cells/ml for 24 hr with the indicated ODN at 30 µg/ml. Std. dev. of the triplicate wells was <7%. None of the ODN induced significant amounts of IL-5.

TABLE 14

Inhibition of CpG-induced cytokine secretion by ODN containing CpG-N motifs

| ODN | sequence 5'-3' | IL-12 secretion[1] | CpG-S-induced IL-12 secretion[2] |
|---|---|---|---|
| none | | 268 | 5453 |
| 1895 | GCGCGCGCGCGCGCGCGCGC(SEQ ID NO:76) | 123 | 2719 |
| 1896 | CCGGCCGGCCGGCCGGCCGG(SEQ ID NO:77) | 292 | 2740 |
| 1955 | GCGGCGGGCGGCGCGCGCCC(SEQ ID NO:75) | 270 | 2539 |
| 2037 | TCCATGCCGTTCCTGCCGTT(SEQ ID NO:78) | 423 | 2847 |

[1]BALB/c spleen cells were cultured in 96 well plates at $2 \times 10^7$ cells/ml with the indicated ODN for 24 hr and then the supernatants were assayed for IL-12 by ELISA (pg/ml).
[2]Cells were set up the same as in [1] except that IL-12 secretion was induced by the addition of the CpG ODN 1619 (TCCATGTCGTTCCTGATGCT) at 30 µg/ml. The data shown are representative of 5 experiments.

All references cited herein are hereby incorporated by reference in their entirety. DNA vaccines given intramuscular:

Donnelly, J. J., Uhmer, J. B., & Liu, M. A. (1997). DNA vaccines. Life Sciences, 60, 163–172.

Donnelly, J. J., Ulimer, J. B., Shiver, J. W. & Liu, M. A. DNA vaccines. Ann. Rev. Immunol. 15, 617–648 (1997).

Davis, H. L. (1998). Gene-based vaccines. In: Advanced Gene Delivery: From Concepts to Pharmaceutical Products (Ed. A. Rolland), Harwood Academic Publishers (in press).

Davis, H. L. and Brazolot Millan C. L. (1998). DNA-based immunization. In: Blood Cell Biochemistry, Volume 8: "Hemopoiesis and Gene Therapy" Ed. L. J. Fairbairn and N. Testa, (in press).

Addition of CpG-S motifs to improve DNA vaccines Sato, Y., et al. Immuno-stimulatory DNA sequences necessary for effective intradermal gene immunization. Science 273, 352–354 (1996).

Klimnan, D. M., Yamshchikov, G. & Ishigatsubo, Y. Contribution of CpG motifs to the immunogenicity of DNA vaccines. J. Immunol. 158, 3635–3639 (1997).

Delivery of DNA vaccines as DNA coated onto gold particles and delivered by gene-gun:

Fuller, D. H., Murphey-Corb, M., Clements, J., Barnett, S., & Haynes, J. R. (1996). Induction of immunodeficiency virus-specific immune responses in rhesus monkeys following gene gun-mediated DNA vaccination. J. Med. Primatol., 25, 236241.

Fynan, E. F., Webster, R. G., Fuller, D. H., Haynes, J. R., Santoro, J. C., & Robinson, H. L. (1993). DNA vaccines: Protective immunizations by parental, mucosal, and gene-gun inoculations. Proc. Natl. Acad. Sci. USA, 90, 11478–11482.

Tang, D., DeVit, M., & Johnston, S. A. (1992). Genetic immunization is a simple method for eliciting an immune response. Nature, 356, 152–154.

Haynes, J. R., Fuller, D. H., McCabe, D., Swain, W. F., and Widera, G. (1996) Induction and characterization of humoral and cellular immune responses elicited via gene gun-mediated nucleic acid immunization. Advanced Drug Delivery Reviews, 21, 3–18.

Intramuscular delivery of DNA vaccines

Davis, H. L., Michel, M.-L., Whalen, R. G. (1993b) DNA based immunization for hepatitis B induces continuous secretion of antigen and high levels of circulating antibody. Human Molec. Genet., 2, 1847–1851.

Yankauckas, M. A., Morrow, J. E., Parker, S. E., Abai, A., Rhodes, G. H., Dwarki, V. J., Gromkowski, S. H. (1993) Long-term anti-nucleoprotein cellular and humoral immunity is induced by intramuscular injection of plasmid DNA containing NP gene. DNA Cell Biol., 12, 771–776.

Intradermal delivery of DNA vaccines (injection—not gene gun)

Sato, Y., Roman, M., Tighe, H., Lee, D., Corr, M., Nguyen, M.-D., Silverman, G. J., Lotz, M., Carson, D. A., & Raz, E. (1996). Immunostimulatory DNA sequences necessary for effective intradermal gene immunization. Science, 273, 352–354.

Raz, E., Carson, D. A., Parker, S. E., Parr, T. B., Abai, A. M., Aichinger, G., Gromkowski, S. H., Singh, M., Lew, D., Yankauckas, M. A., Baird, S. M., Rhodes, G. H. (1994) Intradermal gene immunization: the possible role of DNA uptake in the induction of cellular immunity to viruses. Proc. Natl. Acad. Sci. USA, 91, 9519–9523.

mucosal delivery of DNA vaccine: intravaginal

Bagarazzi, M. L., Boyer, J. D., Javadian, M. A., Chattergoon, M., Dang, K., Kim, G., Shah, J., Wang, B., & Weiner, D. B. (1997). Safety and immunogenicity of intramuscular and intravaginal delivery of HIV-1 DNA constructs to infant chimpanzees. J. Med. Primatol., 26, 27–33. intranasal Fynan, E. F., Webster, R. G., Fuller, D. H., Haynes, J. R., Santoro, J. C., & Robinson, H. L. (1993). DNA vaccines: Protective immunizations by parental, mucosal, and gene-gun inoculations. Proc. Natl. Acad. Sci. USA, 90, 11478–11482.

Gramzinski, R. A., Brazolot Millan, C. L., Obaldia, N., Hoffman, S. L., & Davis, H. L. (1998). Immune response to a hepatitis B DNA vaccine in Aotus monkeys: A comparison of vaccine formulation, route and method of administration. Molec. Med, 4:128–142.

oral—microencapsulated

Herrmami, J. E., Chen, S. C., Fynan, E. F., Santoro, J. C., Greenberg, H.B., Wang, S., Robinson, H. L. (1996) Protection against rotavirus infections by DNA vaccination. J. Infect. Dis., 174, S93–97.

oral mucosa with gene-gun

Keller, E. T., Burkholder, J. K., Shi, F., Pugh, T. D., McCabe, D., Malter, J. S., MacEwan, E. g., Yang, N. S., Ershler, W. B. (1996) In vivo particle-mediated cytoline gene transfer into canine oral mucosa and epidermis. Cancer Gene Ther., 3, 186–191.

improvement of DNA vaccines by coexpression of cytokines or costimulatory molecules Geissler, M., Gesien, A., Tokushige, K., Wands, J. R. (1997a) Enhancement of cellular and humoral immune responses to hepatitis C virus core protein using DNA-based vaccines augmented with cytokine-expressing plasmids. J. Immunol., 158, 1231–1237.

Iwasaki, A., Stiernholm, B. J., Chan, A. K., Berinstein, N. L., Barber, B. H. (1997) Enhanced CTL responses mediated by plasmid DNA immunogens encoding costimulatory molecules and cytokines. J. Immunol., 158, 4591–4601.

Kim, J. J., Ayyavoo, V., Bagarazzi, M. L., Chattergoon, M. A., Dang, K, Wang, B., Boyer, J. D., Weiner, D. B. (1997) In vivo engineering of a cellular immune response by coadministration of IL-12 expression vector with a DNA immunogen. J. Immunol., 158, 816–826.

APC can induce immune responses with DNA vaccine—transfected muscle cells cannot:

Corr, M., Lee, D. J., Carson, D. A., & Tighe, H. (1996). Gene vaccination with naked plasmid DNA: Mechanism of CTL priming. J. Exp. Med., 184, 1555–1560.

Doe, B., Selby, S., Barnett, J., Baenziger, J., & Walker, C. M. (1996). Induction of cytotoxic T lymphocytes by intramuscular immunization with plasmid DNA is facilitated by bone marrow-derived cells. Proc. Natl. Acad. Sci. USA, 93, 8578–8583.

Iwasaki, A., Torres, C. A. T., Ohashi, P., Robinson, H. L., & Barber, B. H. (1997). The dominant role of bone-marrow derived cells in CTL induction following plasmid DNA immunization at different sites. J. Immunol., 159, 11–14.

APC (dendritic cells) are transfected by DNA vaccine

Condon, C., Watkins, S. C., Celluzzi, C. M., Thompson, K., Falo, L. D., Jr. (1996) DNA-based immunization by in vivo transfection of dendritic cells. Nat. Med., 2, 1122–1128.

Nature of antigen expression

Davis, H. L., Brazolot Millan, C. L., Watkins, S. C. (1997) Immune-mediated destruction of transfected muscle fibers after direct gene transfer with antigen-expressing plasmid DNA. Gene Ther., 4, 181–188.

Inchauspé, G., Vitvitski, L., Major, M. E., Jung, G., Spengler, U., Maisonnas, M., Trepo, C. (1997) Plasmid DNA expressing a secreted or a nonsecreted form of hepatitis C virus nucleocapsid: comparative studies of antibody and T-helper responses following genetic immunization. DNA Cell Biol., 16, 185–195.

Michel, M. L., Davis, H. L., Schleet M., Mancini, M., Tiollais, P., & Whalen, R. G. (1995). DNA-mediated immunization to the hepatitis B surface antigen in mice: Aspects of the humoral response mimic hepatitis B viral infection in humans. Proc. Natl. Acad. Sci. USA, 92, 5307–5311.

indirect (ex vivo) gene transfer of dendritic cells

Manickan, E., Kanangat, S., Rouse, R. J., Yu, Z., & Rouse, B. T. (1997). Enhancement of immune response to naked DNA vaccine by immunization with transfected dendritic cells. J. Leukoc. Biol., 61, 125–132.

DNA vaccine for treatment of chronic viral infection (animal model) Mancini, M., Hadchouel, M., Davis, H. L., Whalen, R. G., Tiollais, P., & Michel, M. L. (1996). DNA-mediated immunization in a transgenic mouse model of the hepatitis B surface antigen chronic carrier state. Proc. Nati. Acad. Sci. USA, 93, 12496–12501.

DNA vaccines for cancer immunotherapy

Irvine, K. R., Rao, J. B. Rosenberg, S. A., Restifo, N. P. (1996) Cytokine enhancement of DNA immunization leads to effective treatment of established pulmonary metastases. J. Immunol., 156, 238–245.

Bueler, H., Mulligan, R. C. (1996) Induction of antigen-specific tumor immunity by genetic and cellular vaccines against MAGE: enhanced tumor protection by coexpression of granulocyte-macrophage colony-stimulating factor and B7-1. Mol. Med., 2, 545–555.

Ciernik, I. F., Berzofsky, J. A., Carbone, D. P.(1996) Induction of cytotoxic T lymphocytes and antitumor immunity with DNA vaccines expressing single T cell epitopes. J. Immunol., 156, 2369–2375.

Conry, R. M., LoBuglio, A. F., Loechel, F., Moore, S. E., Sumerel, L. A., Barlow, D. L., Curiel D. T., (1995) A carcinoembryonic antigen polynucleotide vaccine has in vivo antitumor activity. Gene Ther., 2, 59–65.

Conry, R. M., LoBuglio, A. F., Loechel, F., Moore, S. E., Sumerel, L. A., Barlow, D. L., Pike, J., Curiel D. T. (1995) A carcinoembryonic antigen polynucleotide vaccine for human clinical use. Cancer Gene Ther., 2, 33–38.

Conry, R. M., LoBuglio, A. F., Curiel, D. T. (1996) Polynucleotide-mediated immunization therapy of cancer. Semin. Oncol. ,23, 135–147.

Schirmbeck, R., Bohm, W., Reimann, J. (1996) DNA vaccination primes MHC class I-restricted, simian virus 40 large tumor antigen-specific CTL in H-2d mice that reject syngeneic tumors. J. Immunol., 157, 3550–3558.

Gene therapy

Mahvi, D. M., Burkholder, J. K., Tunier, J., Culp, J., Malter, J. S., Sondel, P. M., Yang, N. S. (1996) Particle-mediated gene transfer of granulocyte-macrophage colony-stimulating factor cDNA to tumor cells: implications for a clinically relevant tumor vaccine. Hum. Gene Ther., 7, 1535–1543.

Other References:

Ballas, Z. K., Rasmussen, W. L. and Krieg, A. M. Induction of natural killer activity in murine and human cells by CpG motifs in oligodeoxynucleotides and bacterial DNA. J. Immunol. 157: 1840–1845 (1996).

Bartlett, R. J., Secore, S. L., Singer, J. T., Bodo, M., Sharma, K. and Ricordi, C. Long-term expression of a fluorescent reporter gene via direct injection of plasmid vector into mouse skeletal muscle: comparison of human creatine kinase and CMV promoter expression levels in vivo. *Cell Transplantation.* 5: 411–419 (1996).

Bird, A. P. CpG islands as gene markers in the vertebrate nucleus. Trends in Genetics. 3: 342–347 (1987).

Chu, R. S., Targoni, O. S., Krieg, A. M., Lehmann, P. V. and Harding, C. V. CpG Oligodeoxynucleotides act as adjuvants that switch on TH1 immunity. *J. Exp. Med.* 186: 1623–1631 (1997).

Cowdery, J. S., Chace, J. H., Yi, A.-K. and Krieg, A. M. Bacterial DNA induces NK cells to produce interferon-γ in vivo and increases the toxicity of lipopolysaccharide.*J. Immunol.* 156: 4570–4575 (1996).

Davis, H. L., Michel, M. -L. and Whalen, R. G. DNA based immunization for hepatitis B induces continuous secretion of antigen and high levels of circulating antibody. *Human Molec. Genetics.* 2: 1847–1851 (1993a).

Davis H. L., Whalen R. G. and Demeneix B. A. Direct gene transfer into skeletal muscle in vivo: factors affecting efficiency of transfer and stability of expression. *Human Gene Ther.* 4: 151–159 (1 993b).

Davis, H. L. Plasmid DNA expression systems for the purpose of immunization. Current Opinions *Biotech.* 8: 635–640 (1997).

Davis, H. L., Weeratna, R., Waldschmidt, T. J., Schorr, J. and Krieg, A. M. CpG DNA is a potent adjuvant in mice immunized with recombinant hepatitis B surface antigen. *J. Immunol.* 160: 870–876 (1998).

Donnelly, J. J., Ulmer, J. B., Shiver, J. W. and Liu, M. A. DNA vaccines. *Ann. Rev. Immunol.* 15: 617–648 (1997).

Ge, L. and Rudolph, P. Simultaneous introduction of multiple mutations using overlap extension PCR. BioTechniques 22: 28–30 (1997).

Gramzinski, R. A., Brazolot Millan, C. L., Obaldia, N., Hoffman, S. L. & Davis, H. L. Immune response to a hepatitis B DNA vaccine in Aotus monkeys: A comparison of vaccine formulation, route and method of administration. *Molec. Med.* 4: 109–119 (1998).

Gribaudo, G., Ravaglia S., Caliendo A., Cavallo R., Gariglio M., Martinotti M. G. and Landolfo S.

Interferons inhibit onset of murine cytomegalovirus immediate-early gene transcription. *Virology.* 197: 303–311 (1993).

Guidotti, L. G., Ando K., Hobbs M. V., Ishikawa T., Runkel L., Schreiber R. D. and Chisari F. V.
Cytotoxic T lymphocytes inhibit hepatitis B virus gene expression by a noncytolytic mechanism in transgenic mice. *Proc. Natl. Acad. Sci. USA.* 91: 3764–3768 (1994).

Halpern, M. D., Kurlander, R. J. and Pisetsky, D. S. Bacterial DNA induces murine interferon-γ production by stimulation of interleukin-12 and tumor necrosis factor-α. *Cell Immunol.* 167: 72–78 (1996).

Harms, J. S. and Splitter G. A. Interferon-gamma inhibits transgene expression driven by SV40 or CMV promoters but augments expression driven by the mammalian MHC I promoter. *Human Gene Ther.* 6: 1291–1297 (1995).

Horvath, J., Palkonyay, L. and Weber, J. Group C adenovirus DNA sequences in human lymphoid cells. *J. Virol.* 59: 189–192 (1986).

Karlin, S., Doerfler, W. and Cardon, L. R. Why is CpG suppressed in the genomes of virtually all small eukaryotic viruses but not in those of large eukaryotic viruses? *J. Virol.* 68: 2889–2897 (1994).

Klinman, D., Yi, A. -K., Beaucage, S. L., Conover, J. and Krieg, A. M. CpG motifs expressed by bacterial DNA rapidly induce lymphocytes to secrete IL-6, IL-12 and IFN. *Proc. Natl. Acad. Sci. USA.* 93: 2879–2883 (1996).

Klinman, D. M., Yamshchikov G. and Ishigatsubo Y. Contribution of CpG motifs to the immunogenicity of DNA vaccines. *J. Immunol.* 158: 3635–3639 (1997).

Krieg, A. M., Yi, A.-K., Matson, S., Waldschmidt, T. J., Bishop, G. A., Teasdale, R., Koretzky, G. A. and Klinman, D. M. CpG motifs in bacterial DNA trigger direct B-cell activation. *Nature.* 374: 546–549 (1995).

Krieg, A. M., Yi, A.-K., Schorr, J. and Davis, H. L. The role of CpG dinucleotides in DNA vaccines. *Trends Microbiology.* 6: 23–27 (1998).

Lasic, D. D., and Templeton, N. S. Liposomes in gene therapy. *Advanced Drug Delivery Review.* 20: 221–266 (1996).

Leclerc, C., Deriaud, E., Rojas, M. and Whalen, R. G. The preferential induction of a TH1 immune response by DNA-based immunization is mediated by the immunostimulatory effect of plasmid DNA. *Cell Immunology.* 170: 97–106 (1998).

Lipford, G. B., Bauer, M., Blank, C., Reiter, R., Wagner, H. and Heeg, K. CpG-containing synthetic oligonucleotides promote B and cytotoxic T cell responses to protein antigen: a new class of vaccine adjuvants. *Eur. J. Immunol.* 27: 2340–2344 (1997).

Messina, J. P., Gilkeson, G. S. and Pisetsky, D. S. Stimulation of in vitro murine lymphocyte proliferation by bacterial DNA. *J. Immunol.* 147: 1759–1764 (1991).

Miller, A. D. Human gene therapy comes of age. *Nature.* 357: 455–460 (1992).

Moldoveanu, Z., Love-Homan, L., Huang, W. Q. and Krieg, A. M. CpG DNA, A Novel Adjuvant for Systemic and Mucosal Immunization with Influenza Virus. Vaccine (in press) (1998).

Newman, K. D., Dunn, P. F., Owens, J. W., Schulick, A. H., Virmani, R., Sukhova, G., Libby, P. and Dichek, D. A. Adenovirus-mediated gene transfer into normal rabbit arteries results in prolonged vascular cell activation, inflammation, and neointimal hyperplasia. *J. Clin. Invest.* 96: 2955–2965 (1995).

Niwa, H., Yamamura, K., and Miyazaki, 3. Efficient selection for high-expression transfectants with a novel eukaryotic vector. *Gene.* 108: 193–199 (1991).

Pisetsky, D. S. Immunologic consequences of nucleic acid therapy. *Antisense Res. Devel.* 5: 219–225 (1995).

Pisetsky, D. S. The immunologic properties of DNA. *J. Immunol.* 156: 421–423 (1996).

Raz, E., Tighe, E., Sato, Y., Corr, M., Dudler, J. A., Roman, M., Swain, S. L., Spiegeberg, H. L. and Carson, D. A. Preferential induction of a TH1 immune response and inhibition of specific IgE antibody formation by plasmid DNA immunization. *Proc. Natl. Acad. Sci. USA.* 93: 5141–5145 (1996).

Roman, M., Martinorozco, E., Goodman, S., Nguyen, M. D., Sato, Y., Ronaghy, A., Komnbluth, R. S., Richman, D. D., Carson, D. A. and Raz, E. Immunostimulatory DNA sequences function as T helper-1-promoting adjuvants. *Nature Med.* 3: 849–854 (1997).

Sambrook, J., Fritsh, E. F. and Maniatis, T. Molecular Cloning : A Laboratory Manual (2nd edition). Cold Spring Harbor Laboratory Press (1989).

Sato, Y., Roman M., Tighe H., Lee D., Corr M., Nguyen M.-D., Silverman G. J., Lotz M., Carson D. A. and Raz E. immunostimulatory DNA sequences necessary for effective intradennal gene immunization. *Science.* 273: 352–354 (1996).

Shpaer, E. G. & Mullins, J. I. Selection against CpG dinucleotides in lentiviral genes: a possible role of methylation in regulation of viral expression. *Nucl. Acids Res.* 18: 5793–5797 (1990).

Sun, S., Beard, C., Jaenisch, R., Jones, P. and Sprent, J. Mitogenicity of DNA from different organisms for murine B cells. *J. Immunol.* 159: 3119–3125 (1997).

Swain, S. L., Spiegeberg, H. L. and Carson, D. A Preferential induction of a TH1 immune response and inhibition of specific IgE antibody formation by plasmid DNA immunization. *Proc. Natl. Acad. Sci. USA.* 93: 5141–5145 (1996).

Tokunaga, T., Yamamoto, H., Shimada, S., Abe, H., Fukuda, T., Fujisawa, Y., Furutani, Y., Yano, O., Kataoka, T., Sudo, T., Makiguchi, N. and Suganuma, T. Antitumor activity of deoxyribonucleic a acid fraction from mycobacterium bovis GCG. 1. Isolation, physicochemical characterization, and antitumor activity. *JNCI.* 72: 955 (1984).

Tokunaga, T., Yamamoto, S. and Namba, K. A synthetic single-stranded DNA, poly(dG,dC), induces interferon-α/β and -γ, augments natural killer activity, and suppresses tumor growth. *Jpn. J. Cancer Res.* 79: 682–686 (1988).

Vogel, F. R. and Sarver N., Nucleic acid vaccines, *Clin. Microbiol. Rev.* 8: 406–410 (1995).

Weiner, G. J., Liu, H.-M., Wooldridge, J. E., Dahle, C. E. and Krieg, A. M. Immunostimulatory oligodeoxynucleotides containing the CpG motif are effective as immune adjuvants in tumor antigen inmunization. *Proc. Natl. Acad. Sci. USA.* 94:10833 (1997).

Xiang, Z. Q., He, Z., Wang, Y. and Ertl, H. C. J. The effect of interferon-γ on genetic immunization. Vaccine, 15: 896–898 (1997).

Yamamoto, S., Yamamoto Y., Kataoka T., Kuramoto E., Yano O. and Tokunaga T. Unique palindromic sequences in synthetic oligonucleotides are required to induce INF and augment INF-mediated natural killer activity. *J. Immunol.* 148: 4072–4076 (1992).

Yi, A.-K., Chace, J. H., Cowdery, J. S. and Krieg, A. M. IFN-γ promotes IL-6 and IgM secretion in response to CpG motifs in bacterial DNA and oligodeoxynucleotides. *J. Immunol.* 156: 558–564 (1996).

Zabner, J., Ramsey, B. W., Meeker, D. P., Aitken, A. L., Balfour, R. P., Gibson, R. L., Launspach, J., Moscicki, R.

A., Richards, S. M. and Standaert, T. A. Repeat administration of an adenovirus vector encoding cystic fibrosis transmembrane conductance regulator to the nasal epithelium of patients with cystic fibrosis. *J. Clin. Invest.* 97: 1504–1511 (1996).

Zhao, Q., Matson, S., Herrara, C. J., Fisher, E., YU, H., and Krieg, A. M. Comparison of cellular binding and uptake of antisense phosphodiester, phosphorothioate and mixed phosphorothioate and methylphosphonate oligonucleotides. *Antisense Res. Develop.* 3: 53–66. (1993). A number of embodiments of the present invention have been described. Nevertheless, it will be understood that various modifications may be made without departing from the spirit and scope of the invention. Accordingly, other embodiments are within the scope of the following claims.

What is claimed is:

1. A method for producing an immunostimulatory nucleic acid construct comprising at least one CpG-S motif and a nucleic acid encoding an antigen comprising:
   determining CpG-N and CpG-S motifs present in a nucleic acid construct comprising at least one CpG-S motif and a nucleic acid encoding an antigen;
   removing CpG-N motifs from the nucleic acid construct; and
   optionally inserting CpG-S motifs into the nucleic acid construct, thereby producing said immunostimulatory nucleic acid construct that stimulates an immune response against the antigen,
   wherein the CpG-N motifs comprise motifs selected from the group consisting of direct repeats of CpG dinucleotides, CCG trinuclectides, CGG trinucleotides, CCGG tetranucleotides, CGCG tetranucleotides, a combination thereof, and a poly-G motif, wherein the poly-G motif optionally contains at least four Gs in a row or two G trimers, and
   wherein the CpG-S motifs comprise motifs having the formula 5'X$_1$CGX$_2$3' wherein C is unmethylated, at least one nucleotide separates consecutive CG dinucleotides in the motif, X$_1$ is selected from the group consisting of adenine, guanine, and thymine and X$_2$ is selected from the group consisting of cytosine, thymine, and adenine, and
   wherein the CpG-N motifs are removed from non-essential regions of the nucleic acid construct and the CpG-S motifs are inserted into non-essential regions of the nucleic acid construct,
   wherein the antigen is selected from the group consisting of a manmmalian antigen, an avian antigen, an antigen from a pathogen that infects mammalian and avian subjects, wherein the pathogen is selected from the group consisting of a bacterium, a virus, a fungus and a parasite.

2. The method of claim 1, wherein the CpG-N motifs are removed by site-specific mutagenesis.

3. The method of claim 1, wherein the CpG-N motifs are selected from the group consisting of clusters of direct repeats of CpG dinucleotides, CCG trinucleotides, CGG trinucleotides, CCGG tetranucilcotides, CGCG tetranucleotides and a combination thereof.

4. The method of claim 1, wherein the nucleic acid construct is a plasmid.

5. The method of claim 1, wherein the nucleic acid construct is a viral vector.

6. The method of claim 1, wherein the CpG-S motifs in the immunostimulatory nucleic acid construct comprise a CpG motif having the formula:

5'X$_1$CGX$_2$3' wherein at least one nucleotide separates consecutive CpGs, X$_1$ is adenine, guanine, or thymine and X$_2$ is cytosine, thymine, or adenine.

7. The method of claim 6, wherein the CpG-S motif is selected from the group consisting of GACGTT, AGCGTT, AACGCT GTCGTT and AACGAT.

8. The method of claim 6, wherein the CpG-S motif comprises GTCGYT or TGACGTT.

9. The method of claim 6, wherein fie CpG-S motif comprises TGTCGYT.

10. The mdhod of claim 6, wherein the CpG-S motif comprises TCCATGTCGTTCCTGTCGTT (SEQ ID NO:1).

11. The method of claim 6, wherein the CpG-S motif comprises TCCTGACGTTCCTGACGTT (SEQ ID NO:2).

12. The method of claim 6, wherein the CpG-S motif comprises TCGTCGTTTTGTCGTTTGTCGTT (SEQ ID NO:3).

13. The method of claim 6, wherein the CpG-S motif comprises TCAACGTT.

14. The method of claim 1, wherein the antigen is a viral antigen.

15. The method of claim 14, wherein the viral antigen is from Hepatitis B virus (HBV).

16. The method of claim 15, wherein the viral antigen is HBV surface antigen.

17. The method of claim 1, wherein the nucleic acid construct further comprises regulatory sequences for expression of DNA in eukaryotic cells.

18. The method of claim 17, wherein the regulatory sequence is a promoter.

19. The method of claim 18, wherein the promoter is a viral promoter.

20. The method of claim 19, wherein the promoter is a CMV promoter.

21. The method of claim 18, wherein the promoter is insensitive to cytokine regulation.

22. The method of claim 18, wherein the promoter is cytokine sensitive.

23. The method of claim 18, wherein the promoter is a non-viral promoter.

24. The method of claim 18, wherein the promoter is a tissue- or cell-specific promoter.

25. The method of claim 24, wherein the cell specific promoter is operative in antigen-presenting cells.

26. The method of claim 25, wherein the promoter is a mammalian MHC I promoter.

27. A method for enhancing the iminunostimulatory effect of an antigen in a mammalian or avian subject, comprising
administering to the subject an effective amount of the immunostimulatory nucleic acid construct of claim 1 encoding the antigen,
wherein the antigen is selected from the group consisting of a mammalian antigen, an avian antigen, an antigen from a pathogen that infects mammalian and avian subjects, wherein the pathogen is selected from the group consisting of a bacterium, a virus, a fungus and a parasite.

28. The method of claim 1, wherein the antigen is a bacterial antigen.

29. The method of claim 1, wherein the antigen is derived from a parasite.

30. A method of eliciting an immune response against an antigen in a mammalian or avian subject comprising:
administering to the subject an effective amount of an antigen-encoding immunostimulatory nucleic acid construct comprising at least one CpG-S motif and produced by
determining CpGN and CpG-S motifs present in an antigen-encoding nucleic acid construct comprising at least one CpG-S motif; and
removing CpG-N motifs from the nucleic acid construct and
optionally inserting CpG-S motifs into the nucleic acid construct,
thereby eliciting an immune response against the antigen in the mammalian or avian subject,
wherein the CpG-N motifs comprise motifs selected from the group consisting of direct repeats of CpG dinucleotides, CCG trinucleotides, CGG trinucleotides, CCGG tetranucleotides, CGCG tetranucleotides, a combination thereof, and a poly-G motif, wherein the poly-G motif optionally contains at least four Gs in a row or two G trimers,
wherein the CpG-S motifs comprise motifs having the formula $5'X_1CGX_23'$ wherein C is unmethylated, at least one nucleotide separates consecutive CG dinucleotides in the motif $X_1$ is selected from the group consisting of adenine, guanine, and thymine and $X_2$ is selected from the group consisting of cytosine, thymine; and adenine,
wherein the CpG-N motifs are removed from non-essential regions of the nucleic acid construct and the CpG-S motifs are inserted into non-essential regions of the nucleic acid construct.

31. The method of claim 30, wherein the nucleic acid construct further comprises regulatory sequences for expression of DNA in eukaryotic cells.

32. The method of claim 31, wherein the regulatory sequence is a promoter.

33. The method of claim 32, wherein the promoter is a viral promoter.

34. The method of claim 33, wherein the promoter is a CMV promoter.

35. The method of claim 32, wherein the promoter is insensitive to cytokine regulation.

36. The method of claim 32, wherein the promoter is cytokine sensitive.

37. The method of claim 32, wherein the promoter is a non-viral promoter.

38. The method of claim 32, wherein the promoter is a tissue-specific promoter.

39. The method of claim 32, wherein the promoter is a cell-specific promoter.

40. The method of claim 39, wherein the cell-specific promoter is operative in antigen-presenting cells.

41. The method of claim 40, wherein the promoter is a mammalian MHC I promoter.

42. The method of claim 30, wherein the antigen is a viral antigen.

43. The method of claim 42, wherein the viral antigen is from Hepatitis B virus (HBV).

44. The method of claim 30, wherein the CpG-N motifs are selected from the group consisting of clusters of direct repeats of CpG dinucleotides, CCG trinucleotides, CGG trinucleotides, CCGG tetranucleotides, CGCG tetranucleotides and a combination thereof.

45. The method of claim 30, wherein the nucleic acid construct is a plasmid.

46. The method of claim 30, wherein the nucleic acid construct is a viral vector.

47. The method of claim 30, wherein the CpG-S motifs in the immunostimulatory nucleic acid construct comprise a CpG motif having the formula:

$$5'X_1CGX_23'$$

wherein at least one nucleotide separates consecutive CpGs, $X_1$ is adenine, guanine, or thymine and $X_2$ is cytosine, thymine, or adenine.

48. The method of claim 47, wherein the CpG-S motif is selected from the group consisting of GACGTT, AGCGTT, AACGCT, GTCGTT and AACGAT.

49. The method of claim 47, wherein the CpG-S motif comprises GTCGYT or TGACGTT.

50. The method of claim 47, wherein the CpG-S motif comprises TGTCGYT.

51. The method of claim 47, wherein the CpG-S motif comprises TCCATGTCGTTCCTGTCGTT (SEQ ID NO:1).

52. The method of claim 47, wherein the CpG-S motif comprises TCCTGACGTTCCTGACGTT (SEQ ID NO:2).

53. The method of claim 47, wherein the CpG-S motif comprises TCGTCGTTTTGTCGTTTTGTCGTT (SEQ ID NO:3).

54. The method of claim 47, wherein the CpG-S motif comprises TCAACGTT.

55. The method of claim 30, wherein the antigen is derived from a parasite.

56. The method of claim 30, further comprising administering an antigen to the subject.

57. The method of claim 56, wherein the antigen is administered to the subject essentially simultaneously with the immunostimulatory nucleic acid construct.

58. The method of claim 30, wherein the antigen is a bacterial antigen.

59. The method of claim 30, wherein the antigen is derived from a parasite.

60. A method for producing an immunostimulatory nucleic acid construct comprising at least one CpG-S motif and a nucleic acid encoding an antigen comprising:
   determining CpG-N and CpG-S motifs present in a nucleic acid construct comprising at least one CpG-S motif;
   removing CpG-N motifs from the nucleic acid construct; and
   optionally inserting CpG-S motifs into the nucleic acid construct,
   then inserting the nucleic acid encoding the antigen into the nucleic acid construct, thereby producing said immunostimulatory nucleic acid construct that stimulates an immune response against the antigen,
   wherein the CpG-N motifs comprise motifs selected from the group consisting of direct repeats of CpG dinucleotides, CCG trinucleotides, CGG trinucleotides, CCGG tetranucleotides, CGCG tetranucleotides, a combination thereof, and a poly-G motif, wherein the poly-G motif optionally contains at least four Gs in a row or two G trimers, and
   wherein the CpG-S motifs comprise motifs having the formula 5'$X_1CGX_2$3' wherein C is unmethylated, at least one nucleotide separates consecutive CG dinucleotides in the motif, $X_1$ is selected from the group consisting of adenine, guanine, and thymine and $X_2$ is selected from me group consisting of cytosine, thymine, and adenine, and
   wherein the CpG-N motifs are removed from non-essential regions of the nucleic acid construct and the CpG-S motifs arc inserted into non-essential regions of the nucleic acid construct,
   wherein the antigen is selected from the group consisting of a mammalian antigen, an avian antigen, an antigen from a pathogen that infects mammalian and avian subjects, wherein the pathogen is selected from the group consisting of a bacteriun, a virus, a fungus and a parasite.

61. The method of claim 60, wherein the CpG-N motifs are selected from the group consisting of clusters of direct repeats of CpG dinucleotides, CCG trinucleotides, CGG trinucleotides, CCGG tetmanucleotides, CGCG tetranucleotides and a combination thereof.

62. The method of claim 60, wherein the nucleic acid construct is a plasmid.

63. The method of claim 60, wherein the nucleic acid construct is a viral vector.

64. The method of claim 60, wherein tie CpG-S motifs in the immunostimulatory nucleic acid construct comprise a CpG motif having the formula:

$$5'X_1CGX_23'$$

wherein at least one nucleotide separates consecutive CpGs, $X_1$ is adenine, guanine, or thymine and $X_2$ is cytosine, thymine, or adenine.

65. The method of claim 64, wherein the CpG-S motif is selected from the group consisting of GACGTT, AGCGTT, AACGCT, GTCGTT and AACGAT.

66. the method of claim 64, wherein the CpG-S motif comprises GTCGYT or TGACGTT.

67. The method of claim 64, wherein the CpG-S motif comprises TGTCGYT.

68. The method of claim 64, wherein the CpG-S motif comprises TCCATGTCGTTCCTGTCGTT (SEQ ID: NO:1).

69. The method of claim 64, wherein the CpG-S motif comprises TCCTGACGTTCCTGACGTT (SEQ ID NO:2).

70. The method of claim 64, wherein the CpG-S motif comprises TCGTCGTTTTGTCGTTTTGTCGTT (SEQ ID NO:3).

71. The method of claim 64, wherein the CpG-S motif comprises TCAACGTT.

72. The method of claim 60, wherein the antigen is a viral antigen.

73. The method of claim 72, wherein the viral antigen is firom Hepatitis B virus (HBV).

74. The method of claim 73, wherein the viral antigen is HBV surface antigen.

75. The method of claim 65, further comprising inserting to the nucleic acid construct regulatory sequences for expression of DNA in eukaryotic cells.

76. The method of claim 75, wherein the regulatory sequence is a promoter.

77. The method of claim 76, wherein the promoter is a viral promoter.

78. The method of claim 77, wherein the promoter is a CMV promoter.

79. The method of claim 76, wherein the promoter is a tissue- or cell-specific promoter.

80. The method of claim 79, wherein the cell specific promoter is operative in antigen-presenting cells.

81. The method of claim 80, wherein the promoter is a mammalian MHC I promoter.

82. The method of claim 60, wherein the antigen is a bacterial antigen.

83. The method of claim 60, wherein the antigen is derived from a parasite.

84. A method for enhancing the immunostimulatory effect of an antigen in a mammalian or avian subject, comprising
   administering to the subject an effective amount of the immunostimulatory nucleic acid construct of claim 60 encoding the antigen,
   wherein the antigen is selected from the group consisting of a mammalian antigen, an avian antigen, an antigen from a pathogen that infects mamalian and avian subjects, wherein the pathogen is selected from the group consisting of a bacterium, a virus, a fungus and a parasite.

85. A method of eliciting an immune response against an antigen in a mammalian or avian subject comprising:

administering to the subject an effective amount of an antigen-encoding immunostimulatory nucleic acid construct comprising at least one CpG-S motif and produced by determining CpG-N and CpG-S motifs present in a nucleic acid construct comprising at least one CpG-S motif; and removing CpG-N motifs from the nucleic acid construct, optionally inserting CpG-S motifs into the nucleic acid construct, and then inserting a nucleic acid encoding an antigen into the nucleic acid construct, thereby eliciting an immune response against the antigen in the mammalian or avian subject, wherein the CpG-N motifs comprise motifs selected from the group consisting of direct repeats of CpG dinucleotides, CCG trinucleotides, CGG trinucleotides, CCGG tetranucleotides, CGCG tetranucleotides, a combination thereof, and a poly-G motif, wherein the poly-G motif optionally contains at least four Gs in a row or two G trimers, wherein the CpG-S motifs comprise motifs having the formula $5'X_1CGX_23'$ wherein C is unmethylated, at least one nucleotide separates consecutive CG dinucleotides in the motif, $X_1$ is selected from the group consisting of adenine, guanine, and thymine and $X_2$ is selected from the group consisting of cytosine, thymine, and adenine, wherein the CpG-N motifs are removed from non-essential regions of the nucleic acid construct and the CpG-S motifs are inserted into non-essential regions of the nucleic acid construct.

86. The method of claim 85, further comprising inserting into the nucleic acid construct regulatory sequences for expression of DNA in eukaryotic cells.

87. The method of claim 86, wherein the regulatory sequence is a promoter.

88. The method of claim 87, wherein the promoter is a viral promoter.

89. The method of claim 87, wherein the promoter is a CMV promoter.

90. The method of claim 87, wherein the promoter is a tissue-specific promoter.

91. The method of claim 87, wherein the promoter is a cell-specific promoter.

92. The method of claim 91, wherein the cell-specific promoter is operative in autigen-presenting cells.

93. The method of claim 92, wherein the promoter is a mammalian MHC I promoter.

94. The method of claim 85, wherein the antigen is a viral antigen.

95. The method of claim 94, wherein the viral antigen is from Hepatitis B virus (HBV).

96. The method of claim 85, wherein the CpG-N motifs are selected from the group consisting of clusters of direct repeats of CpG dinucieotides, CCG trinucleotides; CGG trinucleotides, CCGG tetranuclootides, CGCG tetranucleotides and a combination thereof.

97. The method of claim 85, wherein the nucleic acid construct is a plasmid.

98. The method of claim 85, wherein the nucleic acid construct is a viral vector.

99. The method of claim 85, wherein the CpG-S motifs in the itmmunostimulatory nucleic acid construct comprise a CpG motif having the formula:

$$5'X_1CGX_23'$$

wherein at least one nucleotide separates consecutive CpGs, $X_1$ is adenine, guanine, or thymine and $X_2$ is cytosine, thymine, or adenine.

100. The method of claim 99, wherein the CpG-S motif is selected from the group consisting of GACGTT, AGCGTT, AACGCT, GTCGTT and AACGAT.

101. The method of claim 99, wherein the CpG-S motif comprises GTCGYT or TGACGTT.

102. The method of claim 99, wherein the CpG-S motif comprises TGTCGYT.

103. The method of claim 99, wherein the CpG-S motif comprises TCCATGTCGTTCCTGTCGTT (SEQ ID NO:1).

104. The method of claim 99, wherein the CpG-S motif comprises TCCTGACGTTCCTGACGTT (SEQ ID NO:2).

105. The method of claim 99, wherein the CpG-S motif comprises TCGTCGTTTTGTCGTTTTGTCGTT (SEQ ID NO:3).

106. The method of claim 99, wherein the CpG-S motif comprises TCAACGTT.

107. The method of claim 85, wherein the antigen is a bacterial antigen.

108. The method of claim 85, wherein the antigen is derived from a parasite.

109. The method of claim 85, further comprising administering an antigen to the subject.

* * * * *

UNITED STATES PATENT AND TRADEMARK OFFICE
CERTIFICATE OF CORRECTION

PATENT NO. : 6,339,068 B1  Page 1 of 2
DATED : January 15, 2002
INVENTOR(S) : Arthur M. Krieg et al.

It is certified that error appears in the above-identified patent and that said Letters Patent is hereby corrected as shown below:

Delete claim 59.

Column 93,
Line 54, delete "trinuclectides" and insert -- trinucleotides --.

Column 94,
Line 42, delete "manmmalian" and insert -- mammalian --.
Line 52, delete "tetranucilcotides" and insert -- tetranucleotides --.
Line 66, delete "GACGTT ,AGCGTT," and insert -- GACGTT, AGCGTT, --
Line 67, insert -- , -- after "AACGCT".

Column 95,
Line 3, delete "fie" and insert -- the --.
Line 5, delete "mdhod" and insert -- method --.
Line 10, delete "TCGTCGTTTTGTCGTTTGTCGTT" and insert
-- TCGTCGTTTTGTCGTTTTGTCGTT --.
Line 25, delete "promoteris" and insert -- promoter is --.
Line 41, delete "iminunostimulatory" and insert -- immunostimulatory --.
Line 62, delete "CpGN" and insert -- CpG-N --.

Column 96,
Line 13, insert -- , -- after "motif".
Line 16, delete ";" and insert -- , --.

Column 97,
Line 51, delete "me" and insert -- the --.
Line 55, delete "arc" and insert -- are --.
Line 61, delete "bacteriun" and insert -- bacterium --.
Line 66, delete "tetmanucleotides" and insert -- tetranucleotides --.

Column 98,
Line 1, delete "methood" and insert -- method --.
Line 5, delete "tie" and insert -- the --.
Line 16, delete the first occurrence of "the" and insert -- The --.
Line 33, delete "firom" and insert -- from --.
Line 36, delete "65" and insert -- 60 --.
Line 37, delete "to" and insert -- into --.
Line 62, delete "mamalian" and insert -- mammalian --.

UNITED STATES PATENT AND TRADEMARK OFFICE
CERTIFICATE OF CORRECTION

PATENT NO.    : 6,339,068 B1
DATED         : January 15, 2002
INVENTOR(S)   : Arthur M. Krieg et al.

It is certified that error appears in the above-identified patent and that said Letters Patent is hereby corrected as shown below:

<u>Column 99,</u>
Line 49, delete "autigen" and insert -- antigen --.

<u>Column 100,</u>
Line 9, delete "dinucieotides" and insert -- dinucleotides --.
Line 10, delete "tetranuclootides" and insert -- tetranucleotides --.
Line 17, delete "itmmunostimulatory" and insert -- immunostimulatory --.

Signed and Sealed this

First Day of October, 2002

*Attest:*

*Attesting Officer*

JAMES E. ROGAN
*Director of the United States Patent and Trademark Office*